(12) United States Patent
Liew

(10) Patent No.: US 7,473,528 B2
(45) Date of Patent: Jan. 6, 2009

(54) METHOD FOR THE DETECTION OF CHAGAS DISEASE RELATED GENE TRANSCRIPTS IN BLOOD

(75) Inventor: Choong-Chin Liew, Toronto, Ontario (CA)

(73) Assignee: GeneNews Inc., Toronto (CA)

( * ) Notice: Subject to any disclaimer, the term of this patent is extended or adjusted under 35 U.S.C. 154(b) by 377 days.

(21) Appl. No.: 10/813,097

(22) Filed: Mar. 30, 2004

(65) Prior Publication Data

US 2004/0241729 A1    Dec. 2, 2004

Related U.S. Application Data

(63) Continuation-in-part of application No. 10/802,875, filed on Mar. 12, 2004, which is a continuation-in-part of application No. 10/601,518, filed on Jun. 20, 2003, which is a continuation-in-part of application No. 10/268,730, filed on Oct. 9, 2002, which is a continuation of application No. 09/477,148, filed on Jan. 4, 2000, now abandoned.

(60) Provisional application No. 60/115,125, filed on Jan. 6, 1999.

(51) Int. Cl.
*C12Q 1/68* (2006.01)
*C12P 19/34* (2006.01)

(52) U.S. Cl. .......................................... 435/6; 435/91.1
(58) Field of Classification Search ........................ None
See application file for complete search history.

(56) References Cited

U.S. PATENT DOCUMENTS

| | | | |
|---|---|---|---|
| 5,352,775 A | 10/1994 | Albertson et al. | |
| 5,739,432 A | 4/1998 | Sinha | |
| 5,837,449 A | 11/1998 | Monia et al. | |
| 5,853,996 A | 12/1998 | Mordechai et al. | |
| 5,882,864 A | 3/1999 | An et al. | |
| 5,942,385 A | 8/1999 | Hirth | |
| 5,994,076 A * | 11/1999 | Chenchik et al. ............... | 435/6 |
| 6,048,709 A | 4/2000 | Falb et al. | |
| 6,124,433 A | 9/2000 | Falb et al. | |
| 6,190,857 B1 | 2/2001 | Ralph et al. | |
| 6,218,529 B1 | 4/2001 | An et al. | |
| 6,251,590 B1 | 6/2001 | Schweighoffer et al. | |
| 6,277,574 B1 | 8/2001 | Walker et al. | |
| 6,479,263 B1 | 11/2002 | Slawin et al. | |
| 6,486,299 B1 | 11/2002 | Shimkets | |
| 6,521,420 B1 | 2/2003 | Herman et al. | |
| 6,525,185 B1 | 2/2003 | Fan et al. | |
| 6,607,898 B1 | 8/2003 | Kopreski et al. | |
| 6,617,170 B2 | 9/2003 | Augello et al. | |
| 6,630,301 B1 | 10/2003 | Gocke et al. | |
| 6,642,002 B2 | 11/2003 | Loyd et al. | |
| 6,692,916 B2 | 2/2004 | Bevilacqua et al. | |
| 2002/0142981 A1 | 10/2002 | Horne et al. | |
| 2003/0104393 A1 | 6/2003 | Sharp et al. | |
| 2003/0180743 A1 | 9/2003 | Nagasu et al. | |
| 2003/0224374 A1 | 12/2003 | Dai et al. | |
| 2004/0121390 A1 | 6/2004 | Sharma et al. | |
| 2006/0271309 A1 * | 11/2006 | Showe et al. ................... | 702/20 |

FOREIGN PATENT DOCUMENTS

| | | |
|---|---|---|
| DE | 44 35 919 C | 12/1995 |
| EP | 0 534 640 A | 3/1993 |
| JP | 09 187299 | 7/1997 |
| WO | WO 98/18906 | 5/1998 |
| WO | WO 98/24935 | 6/1998 |
| WO | WO 98/33942 | 8/1998 |
| WO | WO 98/49302 | * 10/1998 |
| WO | WO 98/49342 | 11/1998 |
| WO | WO/01/25473 | 4/2001 |
| WO | WO/02/14547 | 2/2002 |
| WO | WO/02/057414 A2 | 7/2002 |
| WO | WO/02/074986 | 9/2002 |
| WO | WO/02/103320 | 12/2002 |
| WO | WO/03/008647 | 1/2003 |
| WO | WO/03/040404 | 5/2003 |
| WO | WO/03/061564 | 7/2003 |
| WO | WO/03/072827 | 9/2003 |
| WO | WO/03/086445 | 10/2003 |
| WO | WO/03/090694 | 11/2003 |
| WO | WO/04/061410 | 7/2004 |

OTHER PUBLICATIONS

Wu et al. J. Pathol. 2001; 195:53-65.*

(Continued)

*Primary Examiner*—Juliet C Switzer
(74) *Attorney, Agent, or Firm*—Edwards Angell Palmer & Dodge LLP; Kathleen Williams; Amy DeCloux

(57) ABSTRACT

The present invention is directed to detection and measurement of gene transcripts and their equivalent nucleic acid products in blood. Specifically provided is analysis performed on a drop of blood for detecting, diagnosing and monitoring diseases using gene-specific and/or tissue-specific primers. The present invention also describes methods by which delineation of the sequence and/or quantitation of the expression levels of disease-specific genes allows for an immediate and accurate diagnostic/prognostic test for disease or to assess the effect of a particular treatment regimen.

41 Claims, 34 Drawing Sheets

OTHER PUBLICATIONS

Lee et al. Clinical Chemistry, 47(8):1350-1352, 2001.*
Tsuang et al. American Journal of Medical Genetics, Part B (Neuropsychiatric Genetics) 133B:1-5(2005).*
Newton et al. Journal of Computational Biology, vol. 8, No. 1, 2001, p. 37-52.*
Cheung et al. Nature Genetics, vol. 33, Mar. 2003, pp. 422-425.*
William Chittenden, dissertation entitled "Chronic Hypoxia and Cardiovascular Dysfunction in Sleep Apnea Syndrome" submitted to the faculty of Virginia Polytechnic Institute and State University, Aug. 2002.*
Expression Linked Polymorphism Database, Accessed at http://expoldb.igib.res.in/expol/aboutexpol.html on Apr. 9, 2008, including about database, profile for gene CDC14A, and CDC14A gene expression graphs. 2003.*
Dutra et al. (Scand. J. Immunol. 45, 74-80, 1997).*
Affymetrix GeneChip Human Genome U133 Set datasheet, 2001.*
Claudio, J.O. et al. (1998) Genomics 50:44-52.
Chelly J et al. (1989). Proc. Nat. Acad. Sci. USA. 86:2617-2621.
Chelly J. et al. (1988). Nature 333:858-860.
Drews J & Ryser S (1997). Nature Biotech. 15:1318-9.
Ferrie RM et al. (1992). Am. J. Hum. Genet. 51:251-62.
Fu D-J et al. (1998). Nat. Biotech 16: 381-4.
Gala JL et al. (1998). Clin. Chem. 44(3):472-81.
Geisterfer-Lowrance AAT et al. (1990). Cell 62:999-1006.
Groden J et al. (1991). Cell 66:589-600.
Jandreski MA & Liew CC (1987). Hum. Genet. 76:47-53.
Jin O et al. (1990). Circulation 82:8-16.
Kimoto Y (1998). Mol. Gen. Genet 258:233-239.
Koster M et al. (1996). Nat. Biotech 14: 1123-8.
Liew & Jandreski (1986). Proc. Nat. Acad. Sci. USA. 83:3175-3179.
Liew CC et al. (1990). Nucleic Acids Res. 18:3647-3651.
Liew CC (1993). J Mol. Cell. Cardiol. 25:891-894.
Liew CC et al. (1994). Proc. Natl. Acad. Sci. USA. 91:10645-10649.
Liew et al. (1997). Mol. and Cell Biochem. 172:81-87.
Niimura H et al. (1998). New Eng. J. Med. 338:1248-1257.
Ogawa M (1993). Blood 81:2844-2853.
Riccie et al. (1997) Neuroscience Letters 229:130-134.
Santoro IM & Groden J (1997). Cancer Res. 57:488-494.
Yuasa T et al. (1998). Japanese J. Cancer Res. 89:879-882.
Marshall KW (1996) Journal of Rheumatology 23(4):582-585.
Campbell, C.; Vernon, S.D; Karem, K.L. Nisenbaum, R. Unger, E.R. (2002) *Assessment of Normal Variability in Peripheral Blood Gene Expression*. Disease Markers, 18:201-206.
Yoshikai et al., "Genomic Organization of the Human Amyloid Beta-Precursor Gene" Gene 87:257-263 (1990).
Genbank AC:V00565, Mar. 1995; Bell et al.: "Sequence of the Human Insulin Gene" (XP002141055).
Genbank AJ:003147, Dec. 1998, Bernot et al., "A Transcriptional Map of the FMF Region" (XP002141057).
Genbank AC:M73548, Jan. 1995, Joslyn et al., "Identification of Deletion Mutations and Three New Genes at the Familial Polyposis Locus" (XP002141058).
Genbank AC: X52889, Sep. 1993, Liew, "Complete Sequence and Organization of the Human Cardiac Beta-Myosin Heavy Chain Gene" (XP002141056).
Genbank AC:M54947, Apr. 1993, Seidman et al., "Molecular Studies of the Atrial Natriuretic Factor Gene" (XP002141054).
Nagai et al. "Decrease of the D3 dopamine receptor mRNA expression in lymphocytes from patients with Parkinson's disease," *Neurology* 46:791-795 (1996).
Mattano et al. Sensitive Detection of rRare Circulating Neuroblastoma Cells by the Reverse Transcriptase-Polymerase Chain Reaction *Cancer Research* 52:4701-4705 (1992).
Katz et al. "Molecular Staging of Prostate Cancer with the Use of an Enhanced Reverse Transcriptase-PCR Assay" *Urology* 43(6):765-775 (1994).
Burchill et al. "Neuroblastoma cell detection by reverse transcriptase-polymerase chain reaction (RT-PCR) for tyrosine hydroxylase mRNA" *Int. J. Cancer* 57:671-675 (1994).
Johnson PWM et al. "The molecular detection of circulating tumor cells", *British Journal of Cancer* 72:268-275 (1995), pp. 268-276.

Seiden et al. Detection of Curculating Tumor Cells in Men with Localized Prostate Cancer *Journal of Clinical Oncology* 12(12):2634-2639 (1994).
Moreno J.G. et al. "Detection of Hematogenous Micrometastasis in Patients with Prostate Cancer" *Cancer Research* 52:6110-6112 (1992).
Hannon et al. NCCLS Blood Collection on Filter for Newborn Screening Programs;Approved Standard—Fourth Edition—NCCLS document LA4-A4 [ISBN 1-56238-503-8] NCCLS, 940 West Valley Road, Suite 1400, Wayne Pennsylvania 19087 USA (2003) vol. 23 No.21. pp. 1-31.
Ernst et al. NCCLS Procedures and Devices for the Collection of Diagnostic Capillary Blood Specimens; Approved Standard—Fifth Edition. NCCLS document H4-A5 [ISBN 1-56238-538-0] NCCLS, 940 West Valley Road, Suite 1400, Wayne Pennsylvania 19087 USA (2004) vol. 24 No.21. pp. 1-47.
Kopreski Michael, S. et al. Aug. 1999, "*Detection of Tumor Messenger RNA in the Serum of Patients with Malignant Melanoma*", Clinical Cancer Research vol. 5: 1961-1965.
Vernon, S.D. et al; (2002)*Utility of the Blood for Gene Expression and Profiling and Biomarker Discovery in Chronic Fatigue Syndrome*, Disease Markers, 18: 193-199.
Dasi, Francisco et al. (May 2001) *Real-Time quantification in plasma of human telomerase reverse transcriptase (hTERT) mRNA: A simple blood test to monitor disease in cancer patients.* Laboratory Investigation, vol. 81, No. 5, p. 767-769.
Fleischhacker, Michael et al. (Sep. 2001) *Detection of Amplifiable Messenger RNA in the Serum of Patients with Lung Cancer* Annals. N Y Acad Sciences 945:179-188.
Gal, Shira et al. (Sep. 2001) *Detection of Mammaglobin mRNA in the Plasma of Breast Cancer Patients* Annals, N Y Acad Sciences, 945:192-194.
Zhang, H.Q., Lu, H., Enosawa, S. Takahara, K. Sakamoto, T. Nakjima, H. S. and Suzuki, S. (2002) *Microarray analysis of Gene Expression in Peripheral Blood Mononuclear Cells Derived from Long-Surviving Renal Recipients*, Transplantation Proceedings 34 1757-1759.
Baechler, E.C., Batliwalla, F. M., Karypis, G. Gaffney, P.M.; Ortmann, W.A. Espe, K.J., Shark, K.B., Grande W. J. Hughes, K.M., Kapur, V., Gregersen, P.K and Behrens, T.W. (Mar. 4, 2003) *Interferon-inducible gene expression signature in Peripheral Blood Cells of Patients with Severe Lupus.* PNAS 100 (5):2610-5.
Lo, Y.M. Dennis (Sep. 2001) *Circulating Nucleic Acids in Plasma and Serum: An Overview*, Ann N Y Acad Scien 945: 1-7.
Ng, Enders K.O., Tsui, N.B.Y., Lam, NYL, Chiu, R.W.K., Yu, S.C.H., Wong, S.C.C., Lo, E.S.F., Rainer, T.H., Johnson, P.J., and Lo, Y.M.D. (Aug. 2002) *Presence of Filterable and Nonfilterable mRNA in the Plasma of Cancer Patients and Healthy Individuals.* Clin. Chem. 48(8):1212-1217.
Mengelle, C. Sandres-Saune, K. Pasquier, C. Rostaing, L. Mansuy, J-M, Marty, M. Da Silva, I., Attal, M., Massip, P. and Izopet, J. (Aug. 2003)*Automated Extraction and Quantification of Human Cytomegalovirus DNA in Whole Blood by Real-Time PCR Assay.* J. Clin. Microbiology, 41(8):3840-3845.
Samuel DePrimo et al. (2003) *Expression profiling of Blood Samples from an SU5416 Phase II Metastatic Colorectal Cancer Clinical Trial: A novel strategy for biomarker identification.* BMC Cancer, 3(3): 1-12.
Taback B. et al. (Dec. 15, 2001) *Detection of Occult Metastatic Breast Cancer Cells in Blood by a Multimolecular Marker Assay: Correlation with Clinical Stage of Disease.* Cancer Research, 61:8845-8850.
Schuster R. et al. (2003) *Quantitative Real-Time RT-PCR for Detection of Disseminated Tumor Cells in Periphral Blood of Patients with Colorectal Cancer Using Different mRNA Markers.* Int. J. Cancer. 108:219-227.
Twine et al. (Sep. 15, 2003) *Disease Associated Expression Profiles in Peripheral Blood Mononuclear Cells from Patients with Advanced Renal Cell Carcinoma.* Cancer Research, 63:6069-6075.

Vawter M. et al. (2004) *Microarry screening of lymphocyte gene expression differences in a multiplex schizophrenia pedigree*, Schizophrenia Research, 67 (2004):41-52.

Neumann et al. (Jan. 2002) *Identification of differentially expressed genes in rheumatoid arthritis by a combination of complementary DNA array and RNA arbitrarily primed-polymerase chain reaction*. Arthritis Rheum. 46(1):52-63.

Schwering, I. et al. (2003) *Profiling of Hodgkin's lymphoma cell line L1236 and germinal center B cells: identification of Hodgkin's lymphoma-specific genes*, Molecular Medicine, No. 3-4: 85-95.

Martin, K. et al. (2001) *High-sensitivity array analysis of gene expression for the early detection of disseminated breast tumor cells in peripheral blood* Proceedings of National Academy of Sciences, vol. 98, No. 5:2646-2651.

* cited by examiner

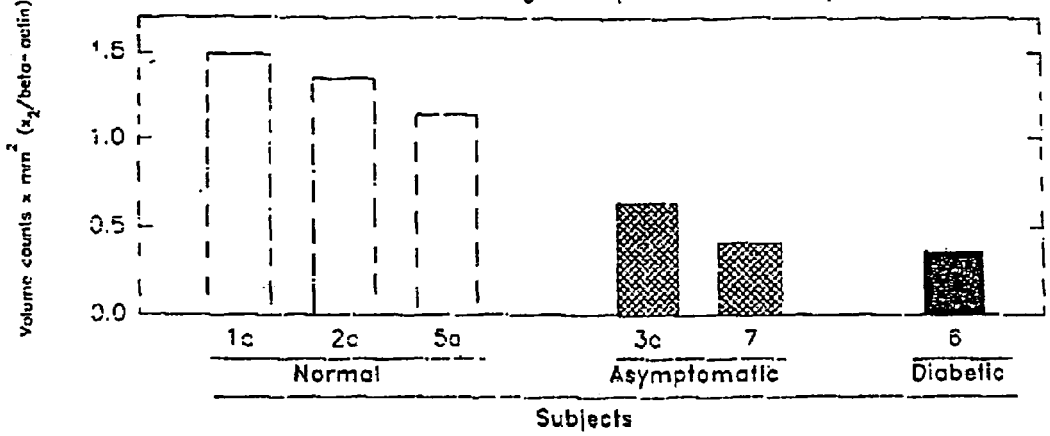
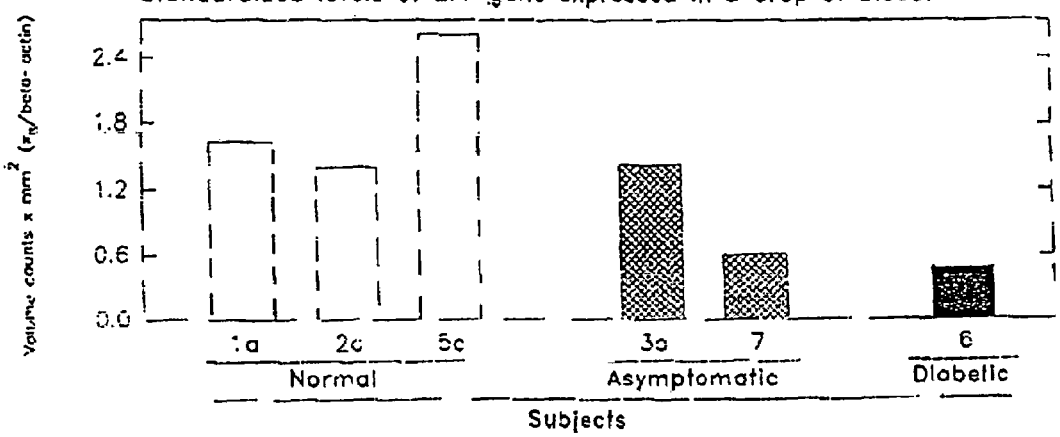
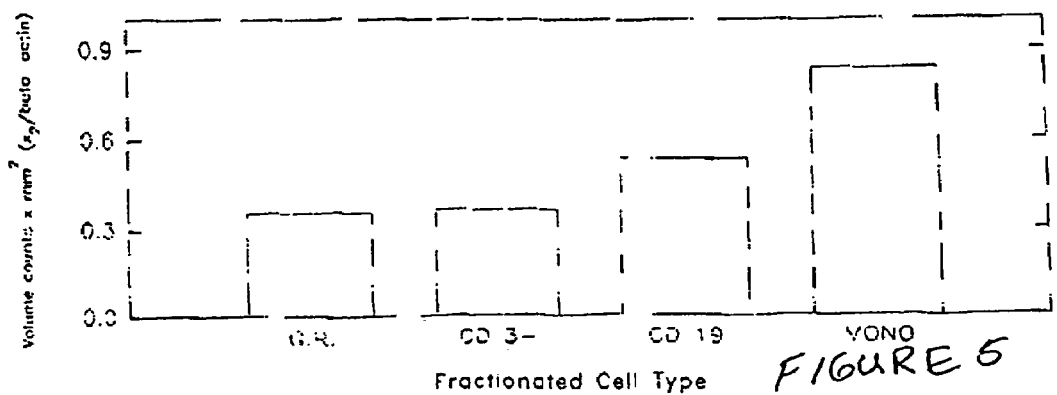
FIGURE 5

A
B
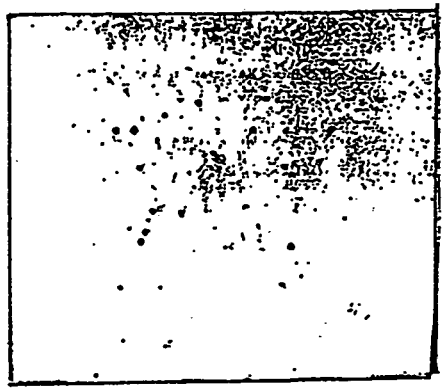
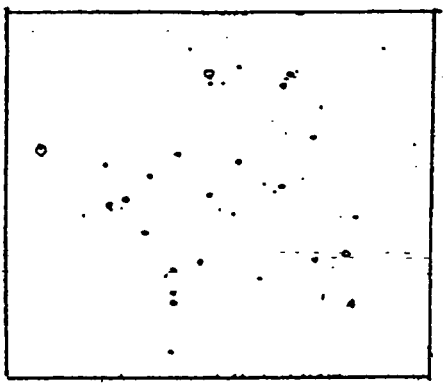
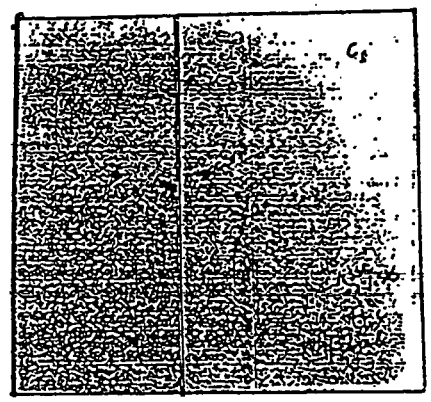
FIGURE 6

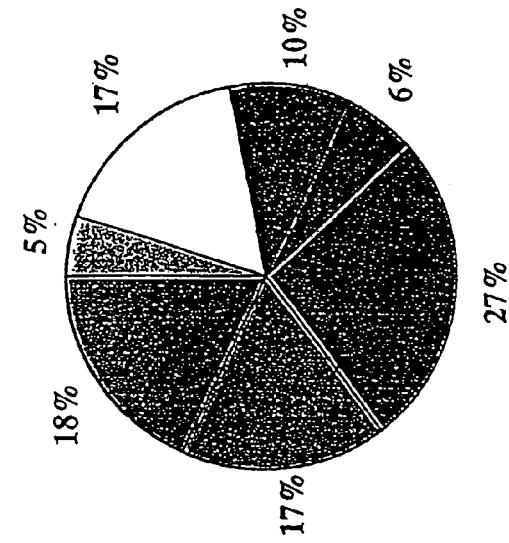
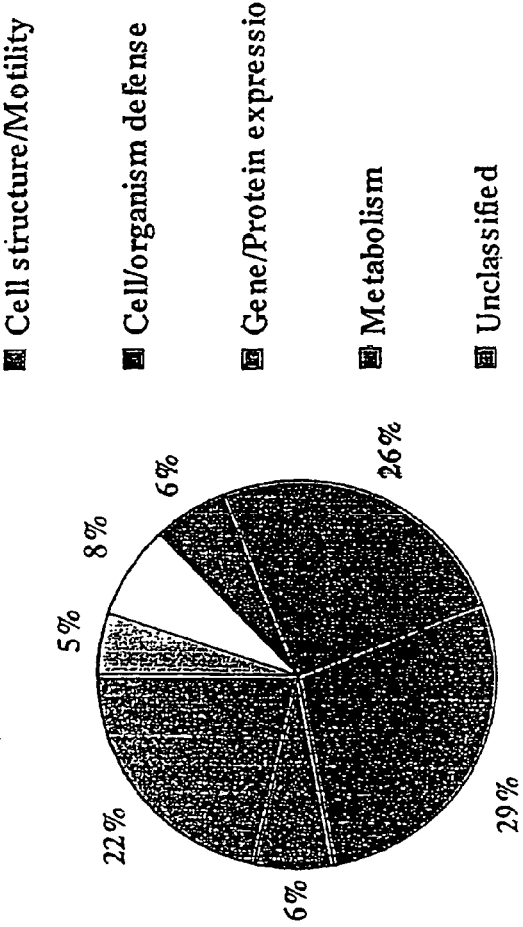
FIGURE 7

Figure 8 Hypertension

Hypertensive: 19
Normal: 22
Differentially Expressed Genes (p<0.05): 861

Obesity

Obese: 25
Normal: 22
Differentially Expressed Genes (p<0.05): 913

Allergies

Allergies: 6
Normal: 22
Differentially Expressed Genes (p<0.05): 633

Systemic Steroids

Systemic Steroids: 9
Normal: 22
Differentially Expressed Genes (p<0.05): 605

Hypertension

Hypertensive   Non-hypertensive   Normal

Hypertensive: 10
Non-hypertensive: 18
Normal: 24
Differentially Expressed Genes (p<0.05): 1,993

Obesity

Obese: 8
Non-obese: 20
Normal: 24
Differentially Expressed Genes (p<0.05): 1,147

Diabetes Type 2

Diabetes Type 2: 5
Non-diabetes Type 2: 23
Normal: 24
Differentially Expressed Genes (p<0.05): 915

Hyperlipidemia: 7
Non-hyperlipidemia: 21
Normal: 24
Differentially Expressed Genes (p<0.05): 1,022

Figure 16 Lung Disease

Lung Disease: 3
Non-lung Disease: 25
Normal: 24
Differentially Expressed Genes (p<0.05): 596

Bladder Cancer

Non-bladder Cancer | Bladder Cancer | Non-bladder Cancer

Bladder Cancer: 5
Non-bladder Cancer: 18
Differentially Expressed Genes (p<0.05): 4,228

Bladder Cancer

Bladder Cancer: 3 advanced stage, 2 early stage
Non-bladder Cancer: 18
Differentially Expressed Genes (p<0.05): 3,518

Coronary Artery Disease: 2
Non-coronary Artery Disease: 21
Differentially Expressed Genes (p<0.05): 967

Rheumatoid Arthritis

Rheumatoid Arthritis: 6
Non-rheumatoid Arthritis: 34
Normal: 12
Differentially Expressed Genes (p<0.05): 2,068

Depression

Normal — Non-depression — Depression

Depression: 3
Non-depression: 37
Normal: 12
Differentially Expressed Genes (p<0.05): 941

Osteoarthritis

Osteoarthritis: 9 mild, 8 moderate, 8 marked, 9 severe
Normal: 9
Differentially Expressed Genes ($p<0.05$): 300

Figure 23  RT-PCR of overexpressed genes in CAD peripheral blood cells identified using microarray experiments, including PBP, PF4 and F13A.

Liver Cancer

Control (red): n=3; Liver Cancer (orange): n=4

Schizophrenia

Control (red): n=6; Schizophrenia (orange): n=4 p<0.005
252 genes

Chagas Disease

Control (orange): n=4; Chagas' asympt. (red): n=4;
Chagas' sympt. (yellow): n=3 p<0.01
155 genes

Asthma

Asthma: n=9 Non-asthma: n=50 p<0.05
219 genes p<0.05
294 genes

Schizophrenia (yellow): n=16; MDS (blue): n=2

MDS = Manic Depression Syndrome

OA Blood Samples Co-morbidities Study: Systemic Steroid Groups
(n=59: mild OA blood-29, severe OA blood-30)

Systemic Steroids (n=9): 3 prednisone, 3 birth control, 3 hormone replacement therapy
Non-systemic steroids: 50
Differentially Expressed Genes (p<0.05): 396

HRT = hormone replacement therapy; BC = birth control

SEQUENCE LISTING

```
<160> NUMBER OF SEQ ID NOS: 112

<210> SEQ ID NO 1
<211> LENGTH: 110
<212> TYPE: DNA
<213> ORGANISM: Human

<400> SEQUENCE: 1
acacaacgta acaataacat atttagccaa tgtagtagac tgctatataa tacattagag        60
tgtcaattca ttccgtttac agccccattg ggtgtcaaat ttttttttgtt              110

<210> SEQ ID NO 2
<211> LENGTH: 530
<212> TYPE: DNA
<213> ORGANISM: Human
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (64)..(66)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (89)..(89)
```

```
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (209)..(210)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (251)..(254)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
```

```
<222> LOCATION: (272)..(272)
<223> OTHER INFORMATION: n is a, c, g, or t
<220> FEATURE:
<221> NAME/KEY: misc_feature
<222> LOCATION: (274)..(275)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (324)..(325)
<223> OTHER INFORMATION: n is a, c, g, or t
<220> FEATURE:
<221> NAME/KEY: misc_feature
<222> LOCATION: (328)..(329)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (412)..(413)
<223> OTHER INFORMATION: n is a, c, g, or t
<220> FEATURE:
```

```
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t

<400> SEQUENCE: 2
gcctgttcta tacagnttnt aaatntcatt tcagatcntn tntntgtgat aatgaatgct    60
gttnnntagn natcctatat natgtncgna cacatcctaa agcataggat gaaaaantga   120
nanccttagg atttngagca cantgccttt acctgaatat atacagcaca gttctgnant   180
ncctggcgtg tgnnactgga gatctctann aaaangnata nagtgggngg gcnctntggc   240
gcntgccggt nnnncctaaa ttttcccan gngnnggagg ccngtcacct gnnccatng   300 cgntctngac cngcctgtna acgnntanng gagccttagt cnctnctaaa aacacaaaat   360
tagccnggca tgggggntgg gnccctttgta ntctnagctn cttgggaggc tnngccagga   420
antncncttg aanccgggna gnggggtggcc tnaagtttgn ggaaggcca ntgatcaccg   480 cccccttcccc tccangcccn gggngaaggg atttgngact tccgttttgg   530

<210> SEQ ID NO 3
<211> LENGTH: 215
```

```
<212> TYPE: DNA
<213> ORGANISM: Human

<400> SEQUENCE: 3
cggcacgagg atcaatttgc cttggaagaa caaaaggaaa gtctggaaat gcagaaagta      60
tggatgctga accacataac agcagatggc attgctgtga agtatactgg atggaataca     120
ttcaagcgtt aatatttaat tcttttgtg gaaggtcaca caattaaaat ttaattgggc      180
atggaggctt aggacggggt aaaaaagtct ttaga                                 215

<210> SEQ ID NO 4
<211> LENGTH: 129
<212> TYPE: DNA
<213> ORGANISM: Human

<400> SEQUENCE: 4
gtttcttttt cctaaaacgg ttttatttaa ctcaatgtgt caaagttttt ttttaataat      60
cccaagaggg atgaagccgt gtccacaggg atatatacat cattatggtt cccatctttc     120
atacatgaa                                                              129

<210> SEQ ID NO 5
<211> LENGTH: 361
<212> TYPE: DNA
<213> ORGANISM: Human
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (25)..(28)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (68)..(68)
```

-continued

```
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (243)..(244)
<223> OTHER INFORMATION: n is a, c, g, or t
<220> FEATURE:
<221> NAME/KEY: misc_feature
<222> LOCATION: (248)..(249)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
```

<222> LOCATION: (334)..(334)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (359)..(360)
<223> OTHER INFORMATION: n is a, c, g, or t

<400> SEQUENCE: 5

```
gggggctttt ttnnancggn nccgnnnncc cttcctggga antttttgggc cnttntntna      60
aangnggnct tncnggnaaa tgggtttttt naggggggctg gncaaaggtt ttttctntaa     120
tgggatnngg ccggcatttt aaaaaaaccc gctttggcct ttttgctana tnggaaaaaa     180
ttttttttaaa angcctaaga canggttttc ccttcatatg ccaaactttc cctaacattt   240
ggnntttnng ggngggcagg gggggatttt taaaccggat ttngggtnaa aaaaaatcng    300
gggggaattt ttgggganaa aaccttnggg gggnccccct ttgaaaanaa agggtgggnn    360
g                                                                    361
```

<210> SEQ ID NO 6
<211> LENGTH: 839
<212> TYPE: DNA
<213> ORGANISM: Human
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (744)..(744)

```
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (808)..(808)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t

<400> SEQUENCE: 6
ctcgtgccga attcggcacg agcaaagtac ctggacttta tggaatcctt ctatacttca      60
ttgtcaatca tttattggtt ctaaaaagga tcggacaatg tgctatttca gggaagccaa     120
tgttttggag taaaatgcac aaataatttc tcttgccttg caaacacatt ttttttttctg    180 tcattgcaat gtgcacaaag ggccacgagg atctacaaga aagcctgcct tattctgacc     240
aggagtgggg agctgacaag aggcttcaca gagcaggtga tgtttagaga ggaatgtctc     300
ccatttccta gtagcctgtg aggctctcaa aaccgggaat caagtttccc ttctgaactc     360
agttctcaat cgtgtaggga tagggttccc aggtgtgcct ctatgtgtag aggctctatt     420
ataccctgga tacacattga tatgcatgtg caatgctgga atcaccagcc ccangtcct     480 cctcccaaat gtgcatgttt tttgacccat gtcacattta atttttttt tcaattgacg     540 ggttttagg gcaaanttnc caaaacatcc cccactttgc catantcccc tgtcattcca      600
tattgncttg cactgacatg attcactcat tgatattgcc tgtngcgttc ctatggcctt     660
tgagtttgca nactgggttt gggggaaacc cangnaaaaa aacctctttg aaangggaa      720 ccccccaat ggtgggggaa ananaactgg actttntttg ggagnccnga atttgctctt      780
gaccaggcag ggacctggga ccctgaangc ttttntaatc ttnggggccn gaaaatntg      839

<210> SEQ ID NO 7
<211> LENGTH: 118
<212> TYPE: DNA
<213> ORGANISM: Human

<400> SEQUENCE: 7
atgggaaagt gtgtaagatt tagaaaaagc attaactatt agtaaacttt atcttaagct      60
ctaacctttg attaggtccc acaaaaatta ggtgatatgc aatttctaat ttagggcc      118

<210> SEQ ID NO 8
<211> LENGTH: 197
```

```
<212> TYPE: DNA
<213> ORGANISM: Human

<400> SEQUENCE: 8
gttgcagtga gccgagatca taccactgca ctccagccta ggcaacagag cgagactcgg      60
tcaaaagaaa aaaaaaaagg ggagctgggc gtgggtacta atgccgtaat cccaggcctt     120
tgggaatccc aggcaaggtg gcctttaggg caaggagttc ggaacctccc tgctaacagg     180
taaaccccct ttccctt                                                    197

<210> SEQ ID NO 9
<211> LENGTH: 250
<212> TYPE: DNA
<213> ORGANISM: Human

<400> SEQUENCE: 9
gagaccaagg ccgccccgct ctggtctcag accagttgtg ctgctcttgc tctggctcag      60
ctggtgtggg gcgcaggcgg gaaacgagac ctctagcatc tggctgaagg ctctgccaag     120
ctcctcttca gggctgcagt ctgcctgcct gcatataccg acttggccag acactgctgc     180
taaattccag ggactctttc tcccctcctc tgctctccag ccaatccttg aggatttaat     240
aactggaagg                                                            250

<210> SEQ ID NO 10
<211> LENGTH: 680
<212> TYPE: DNA
<213> ORGANISM: Human
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t

<400> SEQUENCE: 10
caccaaagaa gcaagagggc tttcttttgt ttctggggac aataactaac tttaatttgc      60
tcttcaagaa gaaggaagct gggtatatag gggaatggca gaagtgctcg cagatgaacc     120
atgaggagca tggtctttaa gaacatgctg agaaggaagc aacacagact ccatcactgg     180
gggaagcacc tgaatagagc actggtaaag gccagtctgt ggacctgagg ccagaggaga     240
tgccaggggt ccagatttca tggcccacag aaacggaact gatcatattt ggttgctggc     300
cagtgttcca tagaccaaga aggctggtag caagtataga ttcctctaca tagcttgaca     360
ggagaagaga aagggaatg tagcacacag gatgcagcag gtgaataaga aaacctcctt     420
ttcccaggtt ggngacagtg agtgatctac agtgatactc aaaagattgt gattggtgtg     480
```

```
ggaattcctg tctcaatatg caatctgcca agaaaacact gtgatggttt cctgtaaagt      540
aaccctcttt tcttatctct aatttcacaa gactcttaaa tgagaggggg gggagaaagn      600
gttctttctc actcncctaa aactgngggt ctgcctggag aaaanctaca tctgcacaga      660
naatgctggt tagccaggaa                                                  680

<210> SEQ ID NO 11
<211> LENGTH: 318
<212> TYPE: DNA
<213> ORGANISM: Human

<400> SEQUENCE: 11
cctgcagagt actccatgga acaattgcc gagcacgtgc tcgcaatttg ccgagcacgg       60
tccggtttga actcctagac taagactagg taggtgatac ataccttctt cccaccaagt     120
actcacgatc caaactatga attttagatt cggatcaaac gaggattgat ccgagggacc     180
aacgttgtga taaatcttac gtcgtcttat atattaagtt tttgtggagg atcggataag     240
tctatagtgt ttgtcacaga tagtcccgta ccacacccca gaccatagga gtcgctctcc     300
ggaccgcggt ctaatggg                                                   318

<210> SEQ ID NO 12
<211> LENGTH: 155
<212> TYPE: DNA
<213> ORGANISM: Human

<400> SEQUENCE: 12
tctcacattg gacatactca aaattcactt ataatcttca caccaccaaa aacttaccca      60
tatcaaatta taaacccacc cacattactt aaaatttttt acatttccca ataaaaaacc     120
caaataaaca aaaacttcca atctccattt aaaat                                155

<210> SEQ ID NO 13
<211> LENGTH: 125
<212> TYPE: DNA
<213> ORGANISM: Human

<400> SEQUENCE: 13
aataaacaaa catgccctct aatatatgaa ttcatcacac aacacgcaca ctgtccccac      60
aaacaccttt ttggtgtcaa gaagaaaaag actagcttca ctgaacagag aaatgctgga     120
cagtg                                                                 125

<210> SEQ ID NO 14
<211> LENGTH: 168
<212> TYPE: DNA
<213> ORGANISM: Human
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
```

```
<222> LOCATION: (56)..(57)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t

<400> SEQUENCE: 14
ggcccntggg ggggnagggc cttttcgggg ccggggnngg gccccntttt ggcccnnggg      60
gggtttcccg gggaacccaa cccctttaagg ggtnggggg  aatttccccc caaaaaaagg    120
gaaaaanttt tccgggggc  ccacccggga agggntnccg gggaaggg                  168

<210> SEQ ID NO 15
<211> LENGTH: 438
<212> TYPE: DNA
<213> ORGANISM: Human

<400> SEQUENCE: 15
aaaaaacttc tttatagtcc ttatatattt ttaattgttt atgttagggg aagctataga     60
ggaacaaatt tgggatagaa atataaggct gggattacag gcatgagcca ccaagcccgg    120
cccacatttc cattttaat atatactgtg ctttacaaat attataatat gttttaaaat     180
atgttcacag aagcacctgg tctgtgaatg gcatgccagc attaaaaaaa ataagcattc    240
tttgaatata tatttagttt tttaatgtgg taggaaaatc aaagccagag ggagtagaaa    300
caaaatttgt gattttctaa atacttcttg gctgcaggga agaaaccacg tcccaggcga    360
agtcctacct aatttgatga taaaattaca tggaagggat tcttgttggc atgaggacct    420
accaagatgg tcaacaga                                                  438

<210> SEQ ID NO 16
<211> LENGTH: 235
<212> TYPE: DNA
<213> ORGANISM: Human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
```

<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t

<400> SEQUENCE: 16 aaggncttttt ccggnccggc ccggcccccc ttggcccang ggggttnccg gnaaaccacc    60
ctttaaggnt tggggggaatt ccccccaaaaa aggaaaaaat tttcccggggg gcccaccccgg  120 aaaggggggaa ggcccccaaa accggggggg gggnaaaaag gtgggtttcc cccttttttcc  180 aattcccaaa accaatttcc aaaaggnaaa ccaaccnttc ccaaaatggg aaagg         235

<210> SEQ ID NO 17
<211> LENGTH: 294
<212> TYPE: DNA
<213> ORGANISM: Human
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t

<400> SEQUENCE: 17

```
aaaccaaccc tttaaggnnt gggggnaat tcccccaaaa aaaaggnaaa aattttttcc      60
gggggnccaa accggnaaag gntttgggaa aaccaaattt ttttggncc caaccccccc     120 caaattgggg ggnaaaccaa atttaagggg ggaagggggg gnccccccg ggaaaggccc     180 aaggggggaa aattttttccg ggggtgggtn ggggggaacca atttaagggg ggggcccccg    240 gggggggttcc ccttgggccn tttttccttt tgggtnaaaa aaaaaaaccc cttg          294
```

<210> SEQ ID NO 18
<211> LENGTH: 453
<212> TYPE: DNA
<213> ORGANISM: Human

<400> SEQUENCE: 18

```
gtagaatata gggtgatact ggagatctac tgcgacctag accatgatac ataaccacac      60
aagtttaatc cctgggttct aactacccctt actgtcactt agcttaacct gcctccaatc   120
ctgtacttga actctaaaac tgttggagaa actcagtgct taccccaaca gattcatttc    180
aaatagctgt aaaaggtatg tttactccag aagaccagag ttgcttcttt tgaacttctc    240
attccttggg cctaggaacc ctcatcaccc tcatcccaac gtcaacccag atcttctctt    300
ccataaacag cactccctca ggcccctgcc tgacacaggc atagactgtc atgttggatt    360
cacagacagg ctgtgctaga ggaaacctct ggggctcacc aggggccgtg ggatgggctt   420
ctggggcttc ttggagccca acttcttcat ggc                                  453
```

<210> SEQ ID NO 19
<211> LENGTH: 242
<212> TYPE: DNA
<213> ORGANISM: Human
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (230)..(230)

<223> OTHER INFORMATION: n is a, c, g, or t

<400> SEQUENCE: 19
gagtcagact gtaaggnacg aaccctcggg gtccccacgn tgttcccccc ggggtaacnt    60
cggcccgggc ccgggnagcc cttcccggc ttttccccg gggggncc ggggggacc      120 tttaggcggc accccaacaa caccaggccc tactttttcc aaggncgggg aagcccatgg  180
gttctgggna acgggcaatg cgggcttgca acgggnggaa naaaaacagn cccaaaagaa  240
tg                                                                 242

<210> SEQ ID NO 20
<211> LENGTH: 181
<212> TYPE: DNA
<213> ORGANISM: Human

<400> SEQUENCE: 20
gtttgtttgt ttttgagatg aatctcactc tgtcgcccag gctggaatgc agtggtgtga   60
tctcagctca ctgcaacctc cacctctcag gagaattgct gaacctggga ggcggaggtt  120
gcagggagct gagattgcgc cactgccctc catcctgggc gacagagcaa gaacctgtct  180
c                                                                  181

<210> SEQ ID NO 21
<211> LENGTH: 100
<212> TYPE: DNA
<213> ORGANISM: Human
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t

```
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 21
gcacaaggaa gggtggncag atnttccngc actggnaaaa ngcngctatg gtngtgaant      60 tncccncen nttnanacna aanntngcac tcttggntgc                           100

<210> SEQ ID NO 22
<211> LENGTH: 100
<212> TYPE: DNA
<213> ORGANISM: Human
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t

<400> SEQUENCE: 22
cntgcgccat ttactgnagg tggacaagga tactatnaac aaagatgtgg cnnaangaga      60
ataatggaag atagctntga ggatnaacnc tggttnaggg                           100
```

<210> SEQ ID NO 23
<211> LENGTH: 100
<212> TYPE: DNA
<213> ORGANISM: Human
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (27)..(29)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 23
acaccttccc acttgcngna aaggggnnng gccccnnct tgggcnganc attaagcctt      60
tttgnggctg cngccctgt gcctggtgcc acaacaaatg                          100

<210> SEQ ID NO 24
<211> LENGTH: 227
<212> TYPE: DNA
<213> ORGANISM: Human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature

```
<222> LOCATION: (177)..(177)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t

<400> SEQUENCE: 24
ccggncacca ccnttaaggt tgggggattt ccccaaaaaa ggaaaatttt cggcggccaa      60
cgggaaggcc nttggggaaa aaaccaangg ncaaacccccc ccaaccacnc ggcccccccc    120 aagggggtg gggaagagcc aaatttcttt gggaaanaac gcccccttgg ggaaaanaag     180
gccaaccacc tttcaacanc ccccaangcg nggaagccat ttcttgg                  227

<210> SEQ ID NO 25
<211> LENGTH: 306
<212> TYPE: DNA
<213> ORGANISM: Human

<400> SEQUENCE: 25
tccaaaagta gagcagaggg atattttgtt ctactgagcc acgaaaaaca cctgaattgt     60
ttcgaccatg tgccttccca ggttgatgaa gacattgcta cacagtctgc agatcaggaa   120
ggaagaattg tatgtgggag tttttaatgg tctcatttca ttggctataa ctcagttaca   180
aggagaaata taactgcaga ggagctttga aaatttagtt cagctgaggg taaaggaaga   240
agagacaaat tttgtcatca gctagtgatc tgccatacaa ggtgttccct taatatgtgt   300
agaatg                                                              306

<210> SEQ ID NO 26
<211> LENGTH: 492
<212> TYPE: DNA
<213> ORGANISM: Human
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (410)..(411)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
```

```
<400> SEQUENCE: 26
cggcttcggg ccaagcgttt ccagagtttg ccgaactgct gagcaagttc gctattctcc      60
agatcgccta gcccctttgcg ggcgaccacc acgatgtccc agcctgtcag gttgtcctga    120
ttgaggcgaa aggactcgcg gatttgacgc ttgatgcggt tgcgctcgac ggcgagcttg    180
acgctctttt tgccgatcac caaacctagg cggggatgat caagctggtt atcgcgcgct    240
agcagcagga cacttttgcc cgggagcttt accgcttggg gagtcgaaga ctgccttgna    300
ttgccgggga gtcagcagtc gcttttttccc ggncgaagcc tcgaactcac canccctgtct    360 ggattaatta gacagcaaga cgcttgcggc ccctttggcg cgaacgaacn ncgaaaagga    420
cttgcgcggc ccgtttcttt gggggggccaa taccggggcn cggggaaaac ccgnggggng    480
gccaaacccc cc                                                         492

<210> SEQ ID NO 27
<211> LENGTH: 500
<212> TYPE: DNA
<213> ORGANISM: Human
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t

<400> SEQUENCE: 27
cgaagcgatg gaagcgcaag cttggtaggg gagcattccc acggcagaga aggtcgggcg      60
acgagccggg ctggagcggt gggaaaagca aatgtaggca taagtaacga caatgcgggc    120
gagaaccccg cacaccgaaa ggctaaggat tcctccgcta tgtcaatcaa cggagggtta    180
gtcgggtact aaggcgttag cgaaggcgaa gcgccgatgt gaaggggggtt aatattcctc    240 cacttgccat gcgtgtgaat ccatgacgga gacgaagccg ggggtgcgtc ctgacggaag    300
tgggcgccag caggggcggc cttcgggcca aaccgaacct caggtcanac ttccaagaaa    360
agtgggtgaa acgccagcgc atggcaaccc gtaccgcaaa ccgacacagg tagccggggg    420
anaacatcct aaggngctcg agagtacttt ctagagcggc cgcgggcccc atcganttt    480 ccacccgggn ggggtaccag                                                 500

<210> SEQ ID NO 28
<211> LENGTH: 231
<212> TYPE: DNA
<213> ORGANISM: Human
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
```

```
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t

<400> SEQUENCE: 28
aagaaattcc gggcacgnag gcacgcccct ggtaattccc caggcgnact tctggggang    60
gctggaaggc ttgnagggca gaaaagggat ccgcctttgg gaggaaccca ggtaaggttt   120
aagaaggaac ccaccctngg ggccaaacaa aaacttaaaa accccccccat ttcntncccc   180 ccaaaaaaaa aattttttaaa aaaaattttt ngccccgggg ggcattgggg g           231

<210> SEQ ID NO 29
<211> LENGTH: 109
<212> TYPE: DNA
<213> ORGANISM: Human
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 29
nncgaacaat angtctggag ctcgtgcgnc ctgnaggtgc gacactagtg gatccaaaga    60
attcggcacg agggattaca gtcgtgagcc actgcacctg gctgcaatt              109

<210> SEQ ID NO 30
<211> LENGTH: 100
<212> TYPE: DNA
<213> ORGANISM: Human
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(13)
```

<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t

<400> SEQUENCE: 30
tcnnnntntg gtntnggctn tccgagnggc anngagtgan tgcccgttnn tattgancac    60
cantcantng ttgccntntg atacccnana caaaattgaa    100

<210> SEQ ID NO 31
<211> LENGTH: 100
<212> TYPE: DNA
<213> ORGANISM: Human
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature

```
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t

<400> SEQUENCE: 31
tcgggcgggg anccctttac ctgtcnttac gatgcgcaag tagatnccng atttngtccn    60
ganggtcgnn aanttaggnt tccagcctgc gncacngcca                        100

<210> SEQ ID NO 32
<211> LENGTH: 104
<212> TYPE: DNA
<213> ORGANISM: Human
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
```

```
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (75)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(98)
<223> OTHER INFORMATION: n is a, c, g, or t

<400> SEQUENCE: 32
cntgctntta cgatgcgcaa ggtagtnccg tgantttagt ccgtgatgtg tcgaaanatt      60
agnnttncag ccngnnnnan tgccattttn gctctnnnga gaaa                     104

<210> SEQ ID NO 33
<211> LENGTH: 102
<212> TYPE: DNA
<213> ORGANISM: Human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 33
tgggntggcc cngcttaact tttgcccncg anctcggngt tcgnacaggg gcgaagnaaa      60
```
ccgccaantt ttttcnaacc cnacttgttt tnggttttag tt            102

<210> SEQ ID NO 34
<211> LENGTH: 100
<212> TYPE: DNA
<213> ORGANISM: Human
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 34
agnacgcctt tacagcttta ngatgcnnga gagagtancg gatttgnccn tgntggtgga      60
naaattaggg ttncagcntg tgnantgcca ttttcgntaa                          100

<210> SEQ ID NO 35
<211> LENGTH: 100
<212> TYPE: DNA
<213> ORGANISM: Human
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (28)..(28)

<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 35
cacgatagca tcagacggcg nncttggngc cnttttgccc gctggtcaca ggacaacgca        60
tttcncnntn tggtgtncgg ctntcacgca tnggcgcgag                             100

<210> SEQ ID NO 36
<211> LENGTH: 153
<212> TYPE: DNA
<213> ORGANISM: Human
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature

```
<222> LOCATION: (115)..(115)
<223> OTHER INFORMATION: n is a, c, g, or t
<220> FEATURE:
<221> NAME/KEY: misc_feature
<222> LOCATION: (117)..(118)
<223> OTHER INFORMATION: n is a, c, g, or t

<400> SEQUENCE: 36
tggngccntt ttgcccgctg gtcacaggna aacgcatttc acnntntggt gttcggntnt      60
cacgcacggc agcgagtgca atgnccgatt cattcttnaa cgacgcacac acccngnngc     120
cctgtgaaac ccataaacag tgggaaatgg tgc                                  153

<210> SEQ ID NO 37
<211> LENGTH: 151
<212> TYPE: DNA
<213> ORGANISM: Human
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t

<400> SEQUENCE: 37
gcgcgcntgn aggccccgac actagtggat ccaaagtatt ttggcacgag ctnagttcga      60
ngatnnagac cncnnatcac ctaatacanc catnactcan atgactnttt gtgcgccttt     120
```

```
tatcanatgc atagcctatc naaaacatca c                              151
```

```
<210> SEQ ID NO 38
<211> LENGTH: 100
<212> TYPE: DNA
<213> ORGANISM: Human
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 38
gngcgcttgn aggccgacac taggggatcc aaagaattcg gcacgagctc gtgccgaatt    60
ngncacgagt tnggctgcnt ctttatacaa cttttcttca                          100

<210> SEQ ID NO 39
<211> LENGTH: 100
<212> TYPE: DNA
<213> ORGANISM: Human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t

<400> SEQUENCE: 39
aaagngnntn ctggnnttan gcanttaacc caggcactgg ggcgctgaac agctactcag    60
ctgcttaagt ngtcccactg gtccagacca gcgacccagc                          100
```

```
<210> SEQ ID NO 40
<211> LENGTH: 102
<212> TYPE: DNA
<213> ORGANISM: Human
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t

<400> SEQUENCE: 40
ttcccccagg atctttctta tatctatcag atctaggtga aaggattact gtcttgtagg      60
tgtcctgaag acaagccgn ttcgtttgaa nctgtgaaat ac                         102

<210> SEQ ID NO 41
<211> LENGTH: 325
<212> TYPE: DNA
<213> ORGANISM: Human

<400> SEQUENCE: 41
ttcggcacga ggagaagaga ggagccgtca gaacatatgg gggatgtgtt caagaagcag      60
atttgtggtc ggaagctttg caaagagggg acctgggtct gagtgacatg cgtggccact     120
ggtgctcctg cgtttggact gtgcaggcct ctcctatgct gatgcgtctc cccactcctg     180
agctaatttc tgctctgctc cttctgtgac atgtggcagc gtgggaaata gccactgtcc     240
cctgtccctg ctgttcctgg tgtcacccag caccaggcca ctctgggagc cagggcagat     300
ggtcctccct gtggtcctgg cctct                                          325

<210> SEQ ID NO 42
<211> LENGTH: 103
<212> TYPE: DNA
<213> ORGANISM: Human
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t

<400> SEQUENCE: 42
gtggcccaag gggnactgaa ggggccctcc ntaagnggag gggttgggga gtaaggcctg      60
ggnaggaccc tgntgactcg gggggcggga gcngggancc agg                      103
```

<210> SEQ ID NO 43
<211> LENGTH: 221
<212> TYPE: DNA
<213> ORGANISM: Human

<400> SEQUENCE: 43 catatttga aatacttttc tcccaaactg ggtttattag cgtgtaccct gcttttccac      60
tttaaaaatt tatgccatat gtccagcttc cagtcagtgc ttctggttag catgaggata    120
actagatttt actgtagatg gtagataaaa gtccagtgaa aagcaaagat gtgtaatgtt   180
ttggtagcct cagtgctctt atcccaagta aaagcaaagt t                       221

<210> SEQ ID NO 44
<211> LENGTH: 100
<212> TYPE: DNA
<213> ORGANISM: Human
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t

<400> SEQUENCE: 44

```
anagagatca ntgatttatt gctgggnncc tgtntganng ntctaaggnn tgaagattat    60
nncattnngc aagcgnacnn gcgcngccna gcngaccagg                         100
```

<210> SEQ ID NO 45
<211> LENGTH: 106
<212> TYPE: DNA
<213> ORGANISM: Human
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t

<400> SEQUENCE: 45

```
atatttcngg agcttgcagc ggcnacacta ggnnactaaa agaattnnag aaagaggnct    60
atnggacnag nanacangaa acctgcanac ttggnngctt ggaagt                  106
```

<210> SEQ ID NO 46
<211> LENGTH: 100
<212> TYPE: DNA
<213> ORGANISM: Human
<220> FEATURE:
<221> NAME/KEY: misc_feature
<222> LOCATION: (74)..(74)
<223> OTHER INFORMATION: n is a, c, g, or t

<400> SEQUENCE: 46

```
gatgtggaga tgcttgatag gttactgggc ggcaatccag gagttgatga agcgcatatg    60
```
cgaacatttc acgngcatat tgcggtgcaa gggcttactg                                    100

<210> SEQ ID NO 47
<211> LENGTH: 101
<212> TYPE: DNA
<213> ORGANISM: Human
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(100)
<223> OTHER INFORMATION: n is a, c, g, or t

<400> SEQUENCE: 47 cccccccnncc cttcttntcc ccnaaagaat aanataagaa tngctannga gnaancgacn         60
anggtnttan nagntatatg tatntnncaa accaantann a        101

<210> SEQ ID NO 48
<211> LENGTH: 100
<212> TYPE: DNA
<213> ORGANISM: Human
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 48
aaggnnaggc tcgttggggg aaaaaacccg ccntnncggg cncccngnaa acccncacna        60
ggggacccna aaaccggaa naaaccnccc nagnaancca        100

<210> SEQ ID NO 49
<211> LENGTH: 473
<212> TYPE: DNA
<213> ORGANISM: Human
<220> FEATURE:
<221> NAME/KEY: misc_feature
<222> LOCATION: (20)..(20)

```
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (386)..(387)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 49
atgagtatga aatgaaaggn tgagatgaaa tgatgatntg agatgagatg aaatgagatg      60
aaaccgagat gaaatgatga aatgatgaga tgagaccgag acgaaatgat gagatgaaat     120
gagatgagat aaaatgagat gaaatgaagt gaaatgaaat gaantcctga aattgacntg     180
agatgaactg agataaaatg ntgagatgaa ntgatgagaa gaaatgagat gaaatgagat     240
gagatgatga gatgaaaaat gctgagatga aacntgatga gatgaaatga tgagatgaat     300
tgaantgaaa tgaaataatg aaataatgac ctgagatgan atgaantgat gaactgatga     360
actaatgaaa tgaaaatgaa atgganntga tgagatgaga agaantgctg agatgagata     420
aaatgagatg aantgatgag atgaantgaa atgctgagat gagatgagat gaa            473

<210> SEQ ID NO 50
<211> LENGTH: 453
<212> TYPE: DNA
<213> ORGANISM: Human
<220> FEATURE:
<221> NAME/KEY: misc_feature
```

```
<222> LOCATION: (5)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
```

```
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (174)..(175)
<223> OTHER INFORMATION: n is a, c, g, or t
<220> FEATURE:
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (223)..(224)
<223> OTHER INFORMATION: n is a, c, g, or t
<220> FEATURE:
<221> NAME/KEY: misc_feature
<222> LOCATION: (233)..(234)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
```

```
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (334)..(335)
<223> OTHER INFORMATION: n is a, c, g, or t
<220> FEATURE:
<221> NAME/KEY: misc_feature
<222> LOCATION: (338)..(339)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (361)..(361)
```

```
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (413)..(414)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t

<400> SEQUENCE: 50
ttccnnagct gtnacganac antcttgaat tgaaattgna cacanctngt gtgnagccct      60
gatanggccn gnaagcaatn tanaggatan ccgnangnta tngnaacaca ttncncnagc     120
ntntncanca gctgatgcag gncncctatg atgcgattan ggactacgac tatnnctcan    180
ngtctnaaca gncgcgangg ctgantacta aaagnacaca aanntgtgca ccnncatnac    240
tcncgttgac tgnacantgt agacctgnaa tacctggctn aaagggtct nactgncatn     300 agagntgnag ntgcccctnc antagngnga gctnnaanng gcctgtnttt gntttacntc    360
ntcgganagg cgatgccatt anagacccna gaacncattg gtgatatacn ctnnaccngg    420
agggnttaca ttgggnaatg atnattatgg ggg                                 453

<210> SEQ ID NO 51
<211> LENGTH: 542
<212> TYPE: DNA
<213> ORGANISM: Human
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
```

<222> LOCATION: (119)..(119)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (425)..(427)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t

<400> SEQUENCE: 51

```
caactgtgag caaggaatnc cattaaatgc cattgtatat tcattgatca gtgaaatcnc    60
atctgggtca cagtggcatc tatgttnaca gtataaatcc ctgtggctat gaatgaaang   120
cttgtttaga cttgcatctg cacatagaag tagggatttc atgctgttat cagcctaatt   180
ttagcctata gaatttcaag ttngctagag gtttngctct ccatggtata agtttagcaa   240
gaaaagtcat ttgtctgctg ctctagcagg ttanaatgtg gaagtatagt gtgcanagtt   300
ttaatccgna tatgttatta aaacatatac atcattttat atcatacatc tgnaataaat   360
attcaaaatt aaatagtgat ttgggattga ttacatctta ttactagctg taataaatga   420
cctcnnngat ngtttaaaat tgttttcctc ncatataata aaaatacctn angcatanat   480
cgattgtcca aaaattgaat atatatacac acctcttcca ttagaactaa atatgtggaa   540
tg                                                                  542
```

<210> SEQ ID NO 52
<211> LENGTH: 733
<212> TYPE: DNA
<213> ORGANISM: Human
<220> FEATURE:

-continued

```
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (90)..(92)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
```

```
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (115)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (154)..(156)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (169)..(172)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (185)..(187)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (200)..(203)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (246)..(247)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (303)..(303)
```

```
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (335)..(336)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
```

-continued

```
<222> LOCATION: (475)..(475)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (505)..(507)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (534)..(535)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (551)..(553)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
```

```
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t

<400> SEQUENCE: 52
atatgacctg cgnncanacn cnctaanang ngactngtta aanacnttcc gtggaatnna    60
ctcagactgc aaantgtnat nctgncnnan nntgnngact gtccngncng atttnnngcn   120
tgnaatacta ttgcctctta tatacacnac caannntgcg aagggcnann nnacctttnc   180
cantnnnctg gggncccacn nnngngaact gagagtggat cttgtgtacc tgacnnacca   240
gntntnnagn agggcgctca ctctgattgg tgcaccatgg ttacacagtg tgtgcaaaga   300
ccngnctatc tcactganga tgattgncag ngccnntggg tggcacnang ggnactgatg   360
ancancactg accctgccga cgccagange cgcanatccg gagantncat gngacnatat   420
aggttaccnc cttcnaccgg gcancaatct gcttctatgg tgaatgcaga ccatntagaa   480
ntctntcnct ataggcatga ttttnnncag tgcgtcagcc ttganaanga ancnnacttt   540
tgntagatga nnngntgctc ncccttgngg ctnacaaatt ccancaccnt tggtggcngc   600
agccnttaag ancacttntt ttgggttgcg ctnttggatg aattacnaat agnntgtttt   660
gttncaaggc ccttctgcna aatatgaana aaagngcnct tagcttttg ngggaactgn   720
actggaaatt ttg                                                      733

<210> SEQ ID NO 53
<211> LENGTH: 100
<212> TYPE: DNA
<213> ORGANISM: Human
<220> FEATURE:
<221> NAME/KEY: misc_feature
```

```
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 53
gatcagacaa gancntggtc cacagcggga cgagagntct cnannctgcn ggggagnnnc      60
caagtacgcn agcnctgaan ctaaagcaag caagaaaaag                           100

<210> SEQ ID NO 54
<211> LENGTH: 515
<212> TYPE: DNA
<213> ORGANISM: Human

<400> SEQUENCE: 54
atatggcaag gataacccct atacttctgc ataatgaatt aactaaaata acttgcaagg      60
agagccaagc taaaccccg ataccgacga gtaccagaac aggtaagcac cccgtctatg     120
tagatatggg aagattatag gaggcgacaa ctaccgagcc tggtgatagc tggtgtccaa    180
gaagagtctt agttcattta tttggcccag aaccctctaa tccccttgta atttatgtca    240
agaggaacag ctctttggac actggaaaac cgtgagagag taagatttac acccttaggg    300
gcctaatagc agccaccatt aagaaagcgt tcgctccaca cccactacct aaaaatcgaa    360
tataactgac tcctcacacc caattggcca atcattcccc tataaaagaa ctatgttagt    420
ataagtaacc tgaaaacatt ctcctctgca taagccctgc gttggattat atcctgcact    480
gacaattaac tgccccaata tctacaatcc aaccc                               515

<210> SEQ ID NO 55
<211> LENGTH: 176
<212> TYPE: DNA
<213> ORGANISM: Human
<220> FEATURE:
<221> NAME/KEY: misc_feature
<222> LOCATION: (5)..(5)
```

<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t

<400> SEQUENCE: 55
tgttnaggat caaattataa tattgaaata anaacagctn acatttatat agcatgtttn      60
cntatctcaa ctaatnataa atgggaaaat gggcaactgg gcaggcngaa cccagaggga     120
agcctgccct cattagacca agacagcaag gtttnccctg gtcactagat gaaatt        176

<210> SEQ ID NO 56
<211> LENGTH: 317
<212> TYPE: DNA
<213> ORGANISM: Human
<220> FEATURE:
<221> NAME/KEY: misc_feature
<222> LOCATION: (4)..(4)
<223> OTHER INFORMATION: n is a, c, g, or t

<400> SEQUENCE: 56
cagnagtgat gttgcaatat ctggaactag caaaggatac tgatgagaaa acgtggaatc      60
atgtgggatg tgacctccta ggactcacct tgcacagctg ggtgcagcag ggataggtaa     120
ggatttgggg tttagaggta caattgcctt tttatggtta gagaaaggtc ctggggctgg     180
agggagcctg acgatctgct ctgtgtgcaa ggggagagtt aactctgcac gcaagagcct     240
gcttaaaggg ctgtgtcagt tctattgtaa acaccaactt aaagtggtgg atgctggcag     300
acattgttat tgccatt                                                    317

<210> SEQ ID NO 57
<211> LENGTH: 209
<212> TYPE: DNA
<213> ORGANISM: Human

<400> SEQUENCE: 57
ctcatacacc tgtggctact gttttctaca gagtgccaaa actattcgag agaataggct      60
ctggactgga cactgtatac ccacatgcaa gatgaagttg gccccttaca tcctatacgc     120
aggagaattg cgtcatttaa agcctgttga cgcttttctc ccgcagacga atggaaagat     180
taattgggag tgggggctga aacaattcg                                       209

<210> SEQ ID NO 58
<211> LENGTH: 262
<212> TYPE: DNA
<213> ORGANISM: Human

<400> SEQUENCE: 58

| aattttgctg ttacatggtg gctcaactga gtcccatact ttgaaggccg ggagttaatc | 60 |
| acctggtcac cgagttgcga accagcctcc aatatgtgga accctgtact ctctaaaaat | 120 |
| caaatcaccg gcatggagat tgcgcctgtg gtcccaaaat actcgggctg ggacacgatg | 180 |
| agttgcttgg cccaaggaag gagggttgta tggctgatca cactggtccg cctgggtgac | 240 |
| agagcgagac tccatctcta at | 262 |

<210> SEQ ID NO 59
<211> LENGTH: 430
<212> TYPE: DNA
<213> ORGANISM: Human

<400> SEQUENCE: 59

| gtcagtttat ttctgactag ggatatttc tttccattta gaaagaaga aaaaaaaaaa | 60 |
| aaacctttat tgtcttacag gggggaacta gcgcggggct gaataaaacc tttggcccct | 120 |
| cccggggggag gggtatccgg tttataaacc ccaagggtat tttcttagca aaatacttaa | 180 |
| aaccggccgg ggttttata caaactggga acccactttt gaaaaatttt ggccttttga | 240 |
| tctgggatgg gaatatgagt ttttatacat ttcattttct ttttgggcaa aggcccggtt | 300 |
| aagtattccc ccccgggggg cctttacaaa aagggcggtt ttaaaagctt ttgggccccc | 360 |
| ctagggaatt gttttaacac ctaaaaaccc ctgcttccct taagggggcg ttctttaatt | 420 |
| tgggggcggc | 430 |

<210> SEQ ID NO 60
<211> LENGTH: 350
<212> TYPE: DNA
<213> ORGANISM: Human

<400> SEQUENCE: 60

| aaacctctct aactatatat cacaataacc tgcgcataag atttacgctc cgatcttttc | 60 |
| atcctactag cttggaggat ttgaaccgat tatgaatacg caatactccc ggtcctcatg | 120 |
| tatcatgtgt aagcccatct cctgggaggg ctaacatact accatctcca aggagaggca | 180 |
| tgattccgaa tcacccacag acagctcgat caccatacgt atcacccaac atatatacct | 240 |
| tctaagactt gctagaaaca accaccacat ttgatgctta atcaccactc tgacgcgcat | 300 |
| taaagtgagg ggactctcct aatttctgta agttgatttt tgcattctga | 350 |

<210> SEQ ID NO 61
<211> LENGTH: 515
<212> TYPE: DNA
<213> ORGANISM: Human

<400> SEQUENCE: 61

| cacataaatt ctccataagt taattagtga ttttaacatg atctcaatat aaacatagca | 60 |
| cactttcttt gagaattcaa catattgcaa gttaaaattt tcatagacta cacaagaaag | 120 |
| aataatcagg caaatcctta agaataaggg caattaagga tgactagccc tacaagattt | 180 |
| taaaaaggat tcattagttt aaaaaatgtg atgtagatac atgaataaaa taaaatcttg | 240 |
| aagtagatcc aaatatacat ggtcagattg aatacaataa agatggcatc gtagcagtgg | 300 |

```
agaaaagaag aattatttca taaaccttgt tggaatggct aggcaatcat ctggaaaaaa      360
atgaagttga ataataaaaa tatattctac actagcacaa attataaata aagcagtgat      420
ttaaatgaga aaaattaaat cataatgatt tcaaagataa cataggataa tttctttata      480
gtcttctaaa atatatgact ttatgaattc tgact                                 515

<210> SEQ ID NO 62
<211> LENGTH: 611
<212> TYPE: DNA
<213> ORGANISM: Human

<400> SEQUENCE: 62
caagtacttt accaactaag ccaatcttgt ccccagccag gcatttctat acaaagggcc       60
aagactttgg ttttataaat aaggaggtat atataaatta tatatatttc tgagctgagt      120
aataatccac cagatacaag tttgcatcaa cttctgtgaa atattttttt tccttttgt       180 tgggcatttt tatggtctaa atatagaatg accaatgcct ctagaacaaa cttgacctgg      240
tcagtgttat caagaagcag actgtttctt actttctttg tatttcctta cttatttaaa      300
tttgttaaaa ttgatatatt gatatataaa acttcttttg ccagtgttgg tggcacacgc      360
ctttaatccc agcacttagg aggcagaggc agggtggatt tctgaatttg agggcaggct      420
agtctacaga gcaagttcca ggtcagccaa ggctatatat agaaactctg gcatgaaaaa      480
ccaaccaaac caaaccaaac caaaccagac cagaccagac cagaccagac caaaccaaac      540
caaaccagac taaaccaaac caaaccagac cagaccagac cagaccagac cagaccagac      600
cagaccaaac t                                                            611

<210> SEQ ID NO 63
<211> LENGTH: 291
<212> TYPE: DNA
<213> ORGANISM: Human

<400> SEQUENCE: 63
ccgagagatt ggccactgct taaactcatg cagctcctac tgttcttcaa ttaatgcctt       60
taatgcgaat atacttcctc ttcttttgc atggtcttgc ccagcctctg caatactgat      120
gaacacatgc tgaagatcat ctaactcaat atggcgcata tttctatgtc ttgctgccca      180
ggacatagga caacttcgtc gctcactagt tctaacatat taatgctggc gtaggtggag      240
aactactgca catatactct tactcggagg ctgaggcacg aggatcactt g                291

<210> SEQ ID NO 64
<211> LENGTH: 309
<212> TYPE: DNA
<213> ORGANISM: Human

<400> SEQUENCE: 64
gccagatgcc gtgtttcctc gatgaactct ttacatcatt ggctattcag tggagtgttt       60
cattatcacc tctcactctc gcgtgttacc taactctccc tcgcagggga aatcactcca      120
tatatttcaa atgtcttgct aacagtggtt actttgctct atccttagct atacgtctcg      180
aggcacattg ttcctctatg ccccgctacg ctttgcccta gagctcggcg gtatctatat      240
cttaactgcc ctcttgatcc ttacgtgccg gagaaggtgg aggcagaaat tttgtcaaat      300
ctgattaga                                                              309

<210> SEQ ID NO 65
<211> LENGTH: 278
```

<212> TYPE: DNA
<213> ORGANISM: Human

<400> SEQUENCE: 65

```
tagaatggaa tggagtcgaa tgtgatggaa tggacgcgaa tggaatggaa tggactcgaa    60
tggaataaag tggaatagac tcgaatggaa tggaatgcaa tggaatggac tcgaatggaa   120
agggatggaa tggactcgaa gggaatggaa tggaatggat tcgaatggaa aggaatggaa   180
tggactcaaa aggaatggaa tggaatggac tcaaatggaa tggactcgaa ttgaatgaaa   240
tgtaatggaa tagactcgaa tggaatggaa cgaaattt                           278
```

<210> SEQ ID NO 66
<211> LENGTH: 142
<212> TYPE: DNA
<213> ORGANISM: Human

<400> SEQUENCE: 66

```
agttctcctt aggttaatta atggaatgca atcccaatga aaatgtcacc aaagttgttt    60
ttttttaac tgtaggaggt ttataataat gctcatatgg aaaaataaaa catgtaaaaa   120
atagctagta aactcccccct gt                                           142
```

<210> SEQ ID NO 67
<211> LENGTH: 286
<212> TYPE: DNA
<213> ORGANISM: Human

<400> SEQUENCE: 67

```
atatctgcca tcctcatcgg ccaatcgtgt tattttgatg acgaatgctt cggagattgg    60
aaagatgatc tcctcatgct tccatgcact gcgagtagaa gacatactga gcatagtgtg   120
attatttttcc caacaaattg gcattcatag atagaataag ctgactaaga ctacttagcc   180
ccacatttt ttctacttgc tccaatagca ctaacaaata ggaagctctt gcttgctccc    240
caaagctcca tttccttgaa agcagaagtg taatattact tcttag                   286
```

<210> SEQ ID NO 68
<211> LENGTH: 179
<212> TYPE: DNA
<213> ORGANISM: Human

<400> SEQUENCE: 68

```
atctactttt tattcttttg ataaatgttt atgaaatata aatactgaa aattagaaag     60
tagaagtcat tattttatta taaacatgt ggattagata ttttcattta tgtgattaaa   120
ctttctaaac aaagattata tgaattatct taaagattta aaaagtaatt aagttaaat    179
```

<210> SEQ ID NO 69
<211> LENGTH: 390
<212> TYPE: DNA
<213> ORGANISM: Human
<220> FEATURE:
<221> NAME/KEY: misc_feature
<222> LOCATION: (356)..(356)
<223> OTHER INFORMATION: n is a, c, g, or t

<400> SEQUENCE: 69

```
cagataagac tattaagaca gataagagcc aaatcatgta gagcctcaga ggttttttgat    60
cttcagtcta agaacgtaaa tccatggaag aattttaagc aggggtgtgc cttgaccaca   120
ttttgaattc taaactgtct ctgggtgggt gtgggtgcca ccaagagcat gtgttcatgt   180
```
agggagactg gttttttaca gttgtctatg agagagatga cagttgcctg gattatggtg    240
gtgacattgg agataagcag gtagacagat tctcagtgta ttaggagaga aaaatcaata    300
ggaaatttaa ataaataat taactgtggc cataggagga aggagtcttt gggttnggtt    360
ctcaatttct gcatgagaaa aaaggtggac    390

<210> SEQ ID NO 70
<211> LENGTH: 481
<212> TYPE: DNA
<213> ORGANISM: Human
<220> FEATURE:
<221> NAME/KEY: misc_feature
<222> LOCATION: (26)..(26)
<223> OTHER INFORMATION: n is a, c, g, or t

<400> SEQUENCE: 70
atgatgaaat gatgagatga aatgcntgag atgagatgtg atgaaatgat gatatgaaat     60
gatgacataa aatgagatga aatgagatgt aatgatggaa tgagatgaga tgaaatgaga    120
tgaaatgata gatgagataa aatgatgata tgaaatgatg agatgaatga tgagatgatg    180
agatgaatga tgaaatgaaa tgatgagatg agatgatgaa atgaaatggt gagatgaaat    240
gatgagatga aatgaaatag tgaaatgaaa ttgaaataaa atcgaaatga gagatgaaat    300
gatgagatga tgaaattgat gaaatgatga gatgtgatga gatgaaatga tgagatgaga    360
tgagatgaca tgaaataatg aaatgaaatt gaaatgagat aagatacgag ctgagatgca    420
atgagatgaa atgatgagat gaaatgaaat agtgaaatga aattgaaata aaatcgaaat    480
g                                                                    481

<210> SEQ ID NO 71
<211> LENGTH: 125
<212> TYPE: DNA
<213> ORGANISM: Human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t

```
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t

<400> SEQUENCE: 71
cggtngcaat tgggggccnc atacgcgcng acgagtantg gncangctnc ttgactacac      60
ngacgcgccg tacaggntna attatggnan cttacatggn aaaggggcan ctcaatgtcc     120
cacag                                                                 125

<210> SEQ ID NO 72
<211> LENGTH: 473
<212> TYPE: DNA
<213> ORGANISM: Human
<220> FEATURE:
<221> NAME/KEY: misc_feature
<222> LOCATION: (151)..(151)
<223> OTHER INFORMATION: n is a, c, g, or t

<400> SEQUENCE: 72
gaaatgaaat aatgaaatga gatgaaataa cgaaataaaa ttgaaatgag atgagaggaa      60
atgagatgaa atgttgaaaa gaaggagga aatgatgagg tgagatgaaa tgatgagatg     120
aaatgaatct gagatgaaat gagatgaaaa ntgatacgaa aaatgatata aaaaatatga    180
cctgagatga atgagatga aaatgatac gaaaatgat ataaaaaata tgacatgaaa      240
tgaaatgaga tgatatgaaa tgacataatg aaatgatgaa ttgatgatat tgaaatgaaa    300
ttgaaagatg agatgaaatg atgagatgaa atgaaatgtt gaaatgatga agagatgtga    360
catgaaatga gctgaaatga gatgaaatga aatgagatta aatgatgaga tgaaaaatga    420
tgagatgaaa aatgagatga gatgatgaga tgagatgaga tgaattgaga tga          473

<210> SEQ ID NO 73
<211> LENGTH: 500
<212> TYPE: DNA
<213> ORGANISM: Human
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t

<400> SEQUENCE: 73
aatgagnatg aaaagnatga aatgatgaga tgaaatgaaa tgatgagatg aaatgaggtg      60
```

```
aaatgaaatt agatgaaatg taatgagatg aaatgaaatg acctaatgaa atgaaataat    120
gaaatgagat gaaataaaat aatgaaatga tgaaataatg aaatgaaaat gagatggaaa    180
tgatgagatg agaagaaatg atgagatgaa atgatgaaat gatgagatga ganaaaatga    240
gatgaaatga tgagatgaga tgaaatatga tgagttgaaa tgacataatg aatgaaatga    300
tgaaatggaa taatgaaatg gaatgatgga gctgagatgc aatgagttga aatgagatga    360
aatgatgaaa tgatgagatg aaatgatgaa atgaaataat gaaatgagat gaaataaaat    420
aatgaaatga tgaaataatg aatgaaaatg gaaatggaaa tgatgagatg agaagaaatg    480
atgagatgaa atgatgaaat                                                500
```

```
<210> SEQ ID NO 74
<211> LENGTH: 299
<212> TYPE: DNA
<213> ORGANISM: Human
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 74
ggaaatcctg aagtggaaat gatgagctga nntgcaatga gttgaaatga gatgaancga    60
tgaaatgatg agatgaaatg atgagatgag atgtgatgaa atgatgatat gaaatgatga    120
cataaaatga gatgaaatga gatgtaatga tggaatgaga tgagatgaaa tgagatgaaa    180
tgatagatga gataaaatga tgatatgaaa tgatgagatg aatgatgaga tgatgagatg    240
aatgatgaaa tgaatgatg agatgagatg atgaaatgaa atggtgagat gaaatgatg    299
```

```
<210> SEQ ID NO 75
<211> LENGTH: 155
<212> TYPE: DNA
<213> ORGANISM: Human

<400> SEQUENCE: 75
agtgaaatga aattgaaata aaatcgaaat gagatgagat gaaatgatga gatgatgaaa    60
taaaatgatg aaatgatgag gtgatgagat gaaatgatga gatgaaatga tgagatgaga    120
tgagatgaca tgaaataatg aaacgaaatt gaaat                              155
```

```
<210> SEQ ID NO 76
<211> LENGTH: 367
<212> TYPE: DNA
<213> ORGANISM: Human
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
```

<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t

<400> SEQUENCE: 76
atagcaaaag ngggtaaaac ccctgagttt gcganannag tantcttgta ggggcnaact    60
ctacttnaga ngaantcctc gcaaaatcct tgaatcaccg cttcagtgca gtgatatcac   120
cgccatgaaa tttctgctcg attagcttac gttgtttgga tagaggccaa acaaggctgt   180
tatcggtacg aggaatggat gttcgatttc gtagaatacg cctgagagac ggcgaatact   240
ctcacgagag gcagcaggcg cgtaaattac ccaattacaa caagtagagg tagcgaagga   300
aaatatgagg ggtggcaagg ttttgcctgt tacattctca aatggaagca aattagatat   360
gtcattg                                                            367

<210> SEQ ID NO 77
<211> LENGTH: 257
<212> TYPE: DNA
<213> ORGANISM: Human
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 77
actagnacag naattttagc taagtggagt ttgagttaag tggagatgtg agaccatctc    60
atagaaatca ttatttctgt gggatggata attgggccaa attgtaaaat attttaacta   120
tcagtgtttg gggtttattt ttaaaagaat agggtgccac cagatgttct ttagtggagg   180
agaaatgagg ccagagtgac tgcctagaaa attaagttgg taaattaatc acttttttct   240
aggtcctttc ttagtct                                                 257

<210> SEQ ID NO 78
<211> LENGTH: 373
<212> TYPE: DNA
<213> ORGANISM: Human
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:

<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t

<400> SEQUENCE: 78

```
ctttaaaaac ntgttagacn aacnttaaaa nttaccentt ttcctgaact gantcctggg      60
nntaantaaa aagggtgaag aannttactt cncttggtcc taaaaaacnt tttcntcagt     120
tattaccaaa atatttggac cattantaaa gantagggcc aacccnaatt tttcttgaaa     180
tttccgttaa atagccgtta aatgttttta cccatttcat attggatacc ttaaattata    240
ataatggatt ttattgttaa attgtgtgtg tgtggtgtgt atgccctgtc ttttctcctc     300
taccattatt gtcactttat gtttggaacc ccctttaccc ttccttaaag gaaaaaagg      360
gcccggggtt ttt                                                        373
```

<210> SEQ ID NO 79
<211> LENGTH: 128
<212> TYPE: DNA
<213> ORGANISM: Human
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature

```
<222> LOCATION: (35)..(35)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 79
tcctagtaan ctggtttacn ctgaaagann aagangcctc ccctgttcnc tgaaatacca      60
ccttgatgtt caagtattta agaccctatg cnaatatttt ttacctttc taataaacca     120 tgtttgtt                                                             128

<210> SEQ ID NO 80
<211> LENGTH: 213
<212> TYPE: DNA
<213> ORGANISM: Human
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (166)..(167)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (206)..(206)
```

<223> OTHER INFORMATION: n is a, c, g, or t

<400> SEQUENCE: 80

```
cccattggna cagaccccca aaatgggtac attttttagg aaaccaggac ctttccaagg      60
ggccaggcct tccctttaaa aaaaaatnac cgtttttngg gggangnaac ctttaaaagg     120
ggaaaanaaa tccttttaa anggaantcc aagggaagga ncctgnncaa nacttccccn     180
ccaataaaaa aaaccntttt ggaaangggg aaa                                  213
```

<210> SEQ ID NO 81
<211> LENGTH: 443
<212> TYPE: DNA
<213> ORGANISM: Human
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 81

```
gaaatgagat gaaaccatga gnatgaaatg aannaatgnc atgcaaatga tgagatgaaa      60
tgatgaaatg agatgagatg agaagaaatg acttgatgag atgagataaa atgatgaaat    120
gaaatgaagt gaaatgaaat tgaaatgaga tgagatgaaa tgagataaaa tgatgagatg    180
aaatgagaag aaatgagatg aaatgatgaa atgatgagat gagatgaaaa atgatgggat    240
gagaaatgag atgaaatgat gggatgaaat gaaatgaaat aatgaaataa tgaaatgaaa    300
tgaattgata atattgaagt gaaattgaaa gatgagattg gatgaaatga tgagatgaaa    360
tgaaatgttg aaatgaaatg aagagatgta acatgaaatg agctgaaatg atgagatgaa    420
atgaaatgaa atgagattaa atg                                             443
```

<210> SEQ ID NO 82
<211> LENGTH: 442
<212> TYPE: DNA
<213> ORGANISM: Human
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature

```
<222> LOCATION: (121)..(121)
<223> OTHER INFORMATION: n is a, c, g, or t

<400> SEQUENCE: 82
tggcccggga acntcnaact gcccatcctg ganttttggg ggggannctt taaaaaacct    60
gacctctgaa tgtattantg anncaagtga tagccaagat attttgaaga aaaatagata   120
ntagggacct gctctataag cccatcataa tttattatga agttataaca agtaaaacag   180
taaggtattt ggcatggaat agagaaccca gaaacagacc caatgcatgg gtacaggata   240
taacacaggg aaatgaggga caatatatgg ttctgggata attatttata tggggaaaat   300
aaagaaattg gatccctacc tcacacatac aaaaaaaatc ataattgaat taaaaacttg   360
catgtgaaag gaaagacttt aaaacattta gaaaaagtat tggaggctat gatcttgggg   420
taggaaagca tttcttttttt tt                                          442

<210> SEQ ID NO 83
<211> LENGTH: 135
<212> TYPE: DNA
<213> ORGANISM: Human
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 83
gtctaacnta aaaagtaaag aaagtaaagt aaaggnttga aggaaggaag gaaggaagga    60
aggagggaaa agaaagaaag gaaggaagga aggaaaagaa agaaagaaag gaaggaagga   120
aggaaggaag gaagg                                                   135

<210> SEQ ID NO 84
<211> LENGTH: 346
<212> TYPE: DNA
<213> ORGANISM: Human
<220> FEATURE:
<221> NAME/KEY: misc_feature
<222> LOCATION: (30)..(30)
<223> OTHER INFORMATION: n is a, c, g, or t

<400> SEQUENCE: 84
ggaggaggaa gagtgatgag ttctctaatn acttggttgg attagcctta gagttatcgg    60
gagttgcctt ctgtaagtgc ccctactatc aaggtttcat ggaaaatcta ggcaaggcag   120
aacttcctca gaaggacaag agacaaagaa gtggggagg ccctcctatc catagctgag   180
agggtttatt ctttgtggtt ctgctgtcag agcctttgga tgtctgatct gagatggagc   240
aaccccagct agacagaact ttgtagattt tgggggttt aaaaggcctc aagcaaattc   300
taaaactttc tttgaaccc ctggcatagg ctcagttttcc ctgact                 346

<210> SEQ ID NO 85
<211> LENGTH: 100
<212> TYPE: DNA
<213> ORGANISM: Human

<400> SEQUENCE: 85
acaaaaagcc cctttaaact tgggcccgct cgaggtcgtt tcgactgggc cgagacttcc    60
gaaaagaaaa tggttttttt tgccgaaatc aaccgggtaa                        100
```

```
<210> SEQ ID NO 86
<211> LENGTH: 201
<212> TYPE: DNA
<213> ORGANISM: Human

<400> SEQUENCE: 86
ttcataacat cgtcattttg ggttatgcga aatacaaatt taaatctttg tgaaatgaaa      60
gaaaagagga agaaacgctt tttaggagtt aaggattaaa gtaaaaatta ttttgacata     120
attacctctt tttgtgacca ctcttaaagg ccaggaacat atttggagaa gcctagttgt    180
atgtaacagt gtgggtttc a                                                 201

<210> SEQ ID NO 87
<211> LENGTH: 531
<212> TYPE: DNA
<213> ORGANISM: Human

<400> SEQUENCE: 87
tatagcgggc gttataaaca taccacttcc cggtacaacg gatttcaagg ttaggggtgc      60
aacccagaac gaacgcgtta agtgcgcgtt atcttcctag gatagagtcg gtgacgggaa    120
tcttttaccc cggcactcgg gtccaccctc gcggcaccag aggtattctc cggcgagtcg    180
ttaaccatcg caatcgccga ccgagtttaa ggaccactcc ccacctttct cattagttaa    240
ggagaacgct actttacccc atagacggag aaatcgctac tcaactacca ggcgcgcgcc    300
gtcgagtccc tcttcctctc tttatgcatt tagagcgctt tcgtaagagt tttccctaga    360
ttcttctaag cgtagcgcgt ctactccaat gttttcgtta atccagcccg aactaacgcc    420
gcggaggagt cgatccgtct actcctatcc cgtcggctcg gatttactac aggagctaag    480
aaaacaaaaa gtaccagccc taaggaaag tcaaggacg cccgtaaaaa a                531

<210> SEQ ID NO 88
<211> LENGTH: 530
<212> TYPE: DNA
<213> ORGANISM: Human

<400> SEQUENCE: 88
aatctcgatc gcaaacatac ggcactctcc ctcttgccgc ggttttcgtc cagcgctttc      60
cattcggtcc agtgcctcgc cctattagcc cttaagccca ccgtttctaa aactcccaga    120
acagccaaac cggtccgccc aaggcctccg tcgttttata atatattccg tttacgtata    180
aggaacgaac cccccttcat taccacggtc ccgcgtccgc ctccttctcc attcgcaaca    240
gttctattcc tttcagcctc ccgtacctgc ttccagaaca tcgcaccgcc atagtcgaaa    300
gatagcaaag attacccagc ttctattcct cgccccagag ccgagtaaat cgaagtttat    360
agaggcggaa tccaaccatt caagagttat aacaagttat cggcactcgg gggatcagaa    420
tataaactta atgtccccctt tattctcccg gacgccctt ttaaccactt cttcctatct    480
ttcgctaaca agccattgac ggcgctttgc cgcgcgggcc catctcgcgt               530

<210> SEQ ID NO 89
<211> LENGTH: 332
<212> TYPE: DNA
<213> ORGANISM: Human
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
```

```
<222> LOCATION: (47)..(47)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t

<400> SEQUENCE: 89
ccatttatgg gccggggata tacccacatg gtacagnaca ttacatnttt atggcaccat      60
ttccaccggc ctggttttgg tttttccata attaattaac caggggnncc anttaaaaaa     120
aattaaggna aggnttaaaa aatttaaccca anggggggtt taaagggntt tttttttta     180 aaaaaaagg ttaaanccccc ccctttttttt ttggttggg gtgggaaaat tttgggaanc     240
cttaaccccc gggttttgg gtttttttgg ccaaaacccc ccggaaaaaa attaaaaaaa     300
ggaccggttt ccattttaat gggtattggg aa                                  332

<210> SEQ ID NO 90
<211> LENGTH: 185
<212> TYPE: DNA
<213> ORGANISM: Human

<400> SEQUENCE: 90
actgctataa tgcaggggaa catgttctca gggtcatcct gaggggttgt gtcatggggc      60
cggtggtaac tattaaaaca taagtttaat cggtatttaa aatttaaaa tcaaaaaaaa     120 taaaatatat gcaaccctcc attccaagga agtatgatgt tactagatta tctgaaaatt     180
ctcct                                                                185

<210> SEQ ID NO 91
<211> LENGTH: 365
<212> TYPE: DNA
<213> ORGANISM: Human
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (338)..(339)
<223> OTHER INFORMATION: n is a, c, g, or t
<220> FEATURE:
```

<221> NAME/KEY: misc_feature
<222> LOCATION: (344)..(344)
<223> OTHER INFORMATION: n is a, c, g, or t

<400> SEQUENCE: 91

```
ccagagagcc acaaatgacc aaaatatttt gagatgaaca tgctcgtaga aggtagctga      60 ctaggggta cttgaaaatg ctagaccagg ataactccta agtgtatatc cttggcagac      120
tcgttatgct ttccaatcct gcttgcaata taagacacaa agtcagaata aagctcaaga     180
aaacagaacg tgcaggccat caagcgcaga gcctgctcat tggacaaccg caaagagtag     240
taagtgctgc cgctattcac acttagaaaa ggagaaccac gggaaaaac caaattaatg     300 gggctgcttt ttgtcactct ggcatnagag aattgtgnng aaantttaac ttttgtaagc     360
ttgta                                                                 365
```

<210> SEQ ID NO 92
<211> LENGTH: 113
<212> TYPE: DNA
<213> ORGANISM: Human
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 92

```
acttgacctt atggatgatg ctgcggagtg cntngtaagt gtttcatgat attccttaag      60
aagtcaggat agtagttttc attccttaga tggtacaagt gttgagacaa atg            113
```

<210> SEQ ID NO 93
<211> LENGTH: 210
<212> TYPE: DNA
<213> ORGANISM: Human

<400> SEQUENCE: 93

```
gttttaggga aatttgccag ttttatgttt taatattttt ggaaggaaaa ctgaaaggta      60
atgaaaatgt tactgttgga ttaaaaaaca aattaagtcc aaatagtgat taggcaagtt     120
ggtgaggtag ggggttgctg caagagcgga agttgaaaga tcttggaaaa attaaagaaa     180
cttcatagaa ccccatctct acaccaaaaa                                      210
```

<210> SEQ ID NO 94
<211> LENGTH: 506
<212> TYPE: DNA
<213> ORGANISM: Human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature

```
<222> LOCATION: (46)..(46)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (82)..(84)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (90)..(92)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (133)..(136)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
```

-continued

```
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (185)..(187)
<223> OTHER INFORMATION: n is a, c, g, or t
<220> FEATURE:
<221> NAME/KEY: misc_feature
<222> LOCATION: (190)..(191)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (260)..(261)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(276)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (291)..(292)
<223> OTHER INFORMATION: n is a, c, g, or t
```

```
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (305)..(306)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (318)..(319)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(329)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (348)..(349)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(367)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (376)..(377)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (405)..(405)
```

```
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (442)..(443)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (473)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (487)..(488)
<223> OTHER INFORMATION: n is a, c, g, or t
<220> FEATURE:
<221> NAME/KEY: misc_feature
<222> LOCATION: (495)..(497)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t

<400> SEQUENCE: 94
ttggnggggg ggcgagatcc tactngagac ccttgatnnt gggnanggac cgaagatcna      60
ttaganaccn atgngatggn cnnncnaaan nnttaaagtg agagtccatc tnngaanaaa     120
atgggnaant ttnnnngggg gggggaaaa ancccnnggg tnannggggg cccngggntt     180
naaannnggn nctngggggg ggaaantttt ggcccccccc cgggggnttt ncctnaaaaa     240
aaanccnttt naaanacngn nanaattttn ccnnnncggg gaggngngga nntttttttt     300
tnaannagcc nttttngnna naaaaannnt ggnccccccc ctattccnng gnttttngga     360
ccnttnnanc ntgggnnttt ttagnccttn aaaaaaangc naatnttaag gtaaaaattn     420
ggggggggng gggggnggn gnnttttttt ttntnnggag gggttttttt ccnncgnggg     480
```
ngaaagnntg gggcnnnctn cngccn                                          506

<210> SEQ ID NO 95
<211> LENGTH: 400
<212> TYPE: DNA
<213> ORGANISM: Human
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (123)..(124)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)

```
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(196)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (211)..(212)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
```

-continued

```
<222> LOCATION: (243)..(244)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (354)..(355)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (383)..(384)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
```

<400> SEQUENCE: 95

```
catgaaggaa naagcctgta ctanctgccg gtatccatgn taatctgngg ngatgtcagc      60
agacccagct nagcagatan ctncatttct ntctnaagnc ctttggtctg naggnngnca     120
ntnnanctnc ngntnaacat cacagctnct ccnagcatca ccctgctagn tancngnggg     180
ttttctctta tntgnngncn naacatctgc nngctctgnt annaanaatt ncataccgcn     240
canngtctnt gacgntgtga tgcatacgnt tgggcagagn gancaatang tgngcatatg     300
cgtgccttac ncaaggatac ggangngctt gaaattgatg ngaccaanan tttnngtacg     360
gtaagtnacc caaccacttc tgnnttcact ntaagagncn                           400
```

<210> SEQ ID NO 96
<211> LENGTH: 800
<212> TYPE: DNA
<213> ORGANISM: Human
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (709)..(710)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature

```
<222> LOCATION: (788)..(788)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t

<400> SEQUENCE: 96
gagatgaatg atgaaatgat gagatgagat gatgaaatga aatggtgaga tgaactgatg    60
aaatgaaatg aaataatgaa atgaaattga aataaaattg aaatgagatg agatgaaatg   120
atgagatgat gaaataaaat gatgaaatga gatgtgatga gatgaaatga ngagatgaaa   180
tgatgagatg agatgacatg aaataaatga aataatgaaa tcgaaatgag atgagaagat   240
acgagatgag atgaaatgat gagatgaaat gatgaaatga gataagatga aaagagttga   300
tgagatgatg agatgaaatg agatgaaaag agatgaaatg agatgaaatg aaatgatgag   360
atgaaatgag gtgaaatgaa attagatgaa acgtaatgag atgaaatgac ataatgaaat   420
gaaaaaatga aatgaaataa tgaaatgagg tgaaattaaa tgagatgatg aaattaaatg   480
atgaaatgaa ataatgaaat ggaaatgaaa tggaaatgat gagatgaatg atgagatgaa   540
atgatgagat gagatgtatt gatgagagga aatgatgaga tgtaatgaaa tgagatgaaa   600
tgaatgagat gaaatggaat antggaangg aaattgattg gngatttgag atgaaatgag   660
ntaaatgnga tgaattaatg atgagatgaa atgntgaatg ccggggtgnn tgagatgaat   720
tgagttgaac cctgngatga atgaagattg nntgaatggt ggntgaatgt tgaatggntg   780
gntggnanaa tgcctgtngg                                               800

<210> SEQ ID NO 97
<211> LENGTH: 334
<212> TYPE: DNA
<213> ORGANISM: Human

<400> SEQUENCE: 97
gatgaattga aatgaaatga aataatgaaa taatgaaatg agatgaaatg aaaagaaatg    60
atgaaatgat attgaaatga aattgaaaga tgagatgatg agatgaaatg gtgaaatgtt   120
gaaatgaaat gatgaaatga atagatgtga catgaaatga gctgaaatga tgagatcaaa   180
tgaaatgaaa tgagattaaa tgatgagatg aaaactgatg aaaacttaaa tgatgaaata   240
atgaaatgaa aatgaaatgg aaatgatgag atgagaagaa atgatgagat gagatgagat   300
aaaatgagat gaaatgatga gatgaaatga tgag                               334

<210> SEQ ID NO 98
<211> LENGTH: 100
<212> TYPE: DNA
<213> ORGANISM: Human
<220> FEATURE:
<221> NAME/KEY: misc_feature
<222> LOCATION: (17)..(17)
<223> OTHER INFORMATION: n is a, c, g, or t

<400> SEQUENCE: 98
ttcaggccgt ctgcttntac atatactatc gagaatggtg ctgtgcactc ataacaccgt    60
tgcttggtag acgcttttga acccttcagc gctgaaagta                         100

<210> SEQ ID NO 99
<211> LENGTH: 500
<212> TYPE: DNA
<213> ORGANISM: Human
<220> FEATURE:
```

```
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t

<400> SEQUENCE: 99
cccgggantt cggcccttat ggcccgggga aatgatgaga tgaaatgatg aaatgagata      60
agatgaaaag agttgatgag atgatgagat gaaatgagat gaaagagat gaaatgagat     120 gaaatgaaat gatgagatga aatgaggtga aatgaaatta gatgaaacgt aatgagatga    180
aatgacctaa tgaaatgaaa aaatgaaatg aaataatgaa atgaggtgaa attaaatgag    240
atgatgaaat taaatgatga aatgaaataa tgaaatggaa atgaaatgga aatgatgaga    300
tgaatgatga gatgaaatga tgagatgaga tctaatgatg agaggagatg atgagatgaa    360
ntgagatgaa aagagatgaa atgagatgaa accgaaatga tgagatgaaa tgaggtgaaa    420
tgaaattaga tgaaacgtaa tgagatgaaa tgacataatg aaatgaaaaa atgaaatgaa    480
ataatgaaat gaggtgaaat                                                500

<210> SEQ ID NO 100
<211> LENGTH: 397
<212> TYPE: DNA
<213> ORGANISM: Human
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 100
cccgggangt ttaagttagg gggcctgccc ctttaagcnt agtcccaccn tgaaanacac      60
tccccttgaa nntctctaaa ccttaacttt ctggccnttt tgtttcagan atgcctaacc    120
ctcagggggt cttttgttct ctacgcctaa aaacttaatc tgtttggaac aattccnttt    180
cctctctgta gaaattgacc tggccatggc tcctgtgaat gatacggttg ctattatccc    240
tgaacactgt aaaaatgaac tttgaaacag ttgggtagga cccaaacaga aaatgatgta    300
tggcttggaa atagtttagc tgaacattat gctttaatat tttactggcc attgcagcac    360
```

```
aggtttagaa atttatgttc ggcttttta  agtttta                            397
```

```
<210> SEQ ID NO 101
<211> LENGTH: 132
<212> TYPE: DNA
<213> ORGANISM: Human
<220> FEATURE:
<221> NAME/KEY: misc_feature
<222> LOCATION: (121)..(121)
<223> OTHER INFORMATION: n is a, c, g, or t

<400> SEQUENCE: 101
gttacctaat gttttactct cattttcttt ttctttattt ttcatttgta aaataggaac    60
attaattgta ctactttcaa aagaattaat tgaagaaaga gagatacagg gtatctaggc   120
ngaggaagac cc                                                       132

<210> SEQ ID NO 102
<211> LENGTH: 246
<212> TYPE: DNA
<213> ORGANISM: Human

<400> SEQUENCE: 102
gggggcttta gttataactg ggctaagcat aattgcgcta ccaattccat attatctcat    60
ggcacttaat tttataattg atatatataa taaaaaattc aatgcagata ttgatataat   120
aaaaatagat aatggtaatc caagcacgat ggtagccatc actctaattg ctttggggtt   180
aacctataac ttattaagta aagtgccaga atggttcttt gacagtatta aaattaaaga   240
aaacag                                                              246

<210> SEQ ID NO 103
<211> LENGTH: 18
<212> TYPE: DNA
<213> ORGANISM: Artificial Sequence
<220> FEATURE:
<223> OTHER INFORMATION: forward primer of exon 1 of insulin gene used
      for quantitative RT-PCR analysis
<220> FEATURE:
<221> NAME/KEY: primer_bind
<222> LOCATION: (1)..(18)

<400> SEQUENCE: 103
gccctctggg gacctgac                                                  18

<210> SEQ ID NO 104
<211> LENGTH: 18
<212> TYPE: DNA
<213> ORGANISM: Artificial Sequence
<220> FEATURE:
<223> OTHER INFORMATION: reverse primer of exons 1 and 2 of insulin gene
      used for quantitative RT-PCR analysis
<220> FEATURE:
<221> NAME/KEY: primer_bind
<222> LOCATION: (1)..(18)

<400> SEQUENCE: 104
cccacctgca ggtcctct                                                  18

<210> SEQ ID NO 105
<211> LENGTH: 24
<212> TYPE: DNA
<213> ORGANISM: Artificial Sequence
<220> FEATURE:
<223> OTHER INFORMATION: forward primer of MyHC gene used for
      quantitative RT-PCR analysis
```

```
<220> FEATURE:
<221> NAME/KEY: primer_bind
<222> LOCATION: (1)..(24)

<400> SEQUENCE: 105
gctggaacgt agagactccc tgct                                        24

<210> SEQ ID NO 106
<211> LENGTH: 24
<212> TYPE: DNA
<213> ORGANISM: Artificial Sequence
<220> FEATURE:
<223> OTHER INFORMATION: reverse primer of  MyHC gene used for
      quantitative RT-PCR analysis
<220> FEATURE:
<221> NAME/KEY: primer_bind
<222> LOCATION: (1)..(24)

<400> SEQUENCE: 106
ggatccttcc agatcatcca cttg                                        24

<210> SEQ ID NO 107
<211> LENGTH: 20
<212> TYPE: DNA
<213> ORGANISM: Artificial Sequence
<220> FEATURE:
<223> OTHER INFORMATION: forward primer of ANF used for quantitative
      RT-PCR analysis
<220> FEATURE:
<221> NAME/KEY: primer_bind
<222> LOCATION: (1)..(20)

<400> SEQUENCE: 107
ggatttcaag aatttgctgg                                             20

<210> SEQ ID NO 108
<211> LENGTH: 20
<212> TYPE: DNA
<213> ORGANISM: Artificial Sequence
<220> FEATURE:
<223> OTHER INFORMATION: reverse primer of ANF used for quantitative
      RT-PCR analysis
<220> FEATURE:
<221> NAME/KEY: primer_bind
<222> LOCATION: (1)..(20)

<400> SEQUENCE: 108
gcagatcgat cagaggagtc                                             20

<210> SEQ ID NO 109
<211> LENGTH: 20
<212> TYPE: DNA
<213> ORGANISM: Artificial Sequence
<220> FEATURE:
<223> OTHER INFORMATION: forward primer of APP used for quantitative
      RT-PCR analysis
<220> FEATURE:
<221> NAME/KEY: primer_bind
<222> LOCATION: (1)..(20)

<400> SEQUENCE: 109
ggatgcttca tgtgaacgtg                                             20

<210> SEQ ID NO 110
<211> LENGTH: 19
<212> TYPE: DNA
<213> ORGANISM: Artificial Sequence
<220> FEATURE:
<223> OTHER INFORMATION: reverse primer of APP used for quantitative
```

-continued

```
        RT-PCR analysis
<220> FEATURE:
<221> NAME/KEY: primer_bind
<222> LOCATION: (1)..(19)

<400> SEQUENCE: 110
tcattcacac cagcacatg                                              19

<210> SEQ ID NO 111
<211> LENGTH: 21
<212> TYPE: DNA
<213> ORGANISM: Artificial Sequence
<220> FEATURE:
<223> OTHER INFORMATION: forward primer of ZFP used for quantitative
      RT-PCR analysis
<220> FEATURE:
<221> NAME/KEY: primer_bind
<222> LOCATION: (1)..(21)

<400> SEQUENCE: 111
cacargagrc arggtcaacg a                                           21

<210> SEQ ID NO 112
<211> LENGTH: 22
<212> TYPE: DNA
<213> ORGANISM: Artificial Sequence
<220> FEATURE:
<223> OTHER INFORMATION: reverse primer of ZFP used for quantitative
      RT-PCR analysis
<220> FEATURE:
<221> NAME/KEY: primer_bind
<222> LOCATION: (1)..(22)

<400> SEQUENCE: 112
ggattaaaat gaagcaccca ga                                          22
```

METHOD FOR THE DETECTION OF CHAGAS DISEASE RELATED GENE TRANSCRIPTS IN BLOOD

RELATED APPLICATIONS

This application is a Continuation-in-Part of Ser. No. 10/802,875, filed: Mar. 12, 2004, which a continuation in part of application Ser. No. 10/601,518, filed on Jun. 20, 2003, which is a continuation-in-part of application Ser. No. 10/268,730 filed on Oct. 9, 2002, which is a continuation of U.S. application Ser. No. 09/477,148 filed Jan. 4, 2000, now abandoned, which claims the benefit of U.S. Provisional Application No. 60/115,125 filed on Jan. 6, 1999. Each of these applications is incorporated herein by reference in their entirety, including figures and drawings.

TABLES

This application includes a compact disc in duplicate (2 compact discs: Tables—Copy 1 and Tables—Copy 2), which are hereby incorporated by reference in their entirety. Each compact disc is identical and contains the following files (corresponding to Tables 2-4):

|   | TABLE | DESCRIPTION | SIZE | CREATED | Text File Name |
|---|---|---|---|---|---|
| 1 | 2 | multi-gene comparison | 371,563 | Mar. 25, 2004 | TABLE2.TXT |
| 2 | 3A | GLF 8 - hypertension | 138,940 | Mar. 28, 2004 | TABLE3A.TXT |
| 3 | 3AA | GLF 29 - asthma | 36,121 | Mar. 27, 2004 | TABLE3AA.TXT |
| 4 | 3AB | multi OA | 29,898 | Mar. 27, 2004 | TABLE3AB.TXT |
| 5 | 3AC | GL MDS vs. schizo | 114,078 | Mar. 27, 2004 | TABLE3AC.TXT |
| 6 | 3AD | steroid differential | 64,646 | Mar. 27, 2004 | TABLE3AD.TXT |
| 7 | 3B | GLF 9 - obesity | 147,421 | Mar. 25, 2004 | TABLE3B.TXT |
| 8 | 3C | GLF 10 - allergies | 95,700 | Mar. 25, 2004 | TABLE3C.TXT |
| 9 | 3D | GLF 11 - steroids | 93,808 | Mar. 25, 2004 | TABLE3D.TXT |
| 10 | 3E | GLF 12 - hypertension | 314,854 | Mar. 25, 2004 | TABLE3E.TXT |
| 11 | 3F | GLF 13 - obesity | 181,310 | Mar. 25, 2004 | TABLE3F.TXT |
| 12 | 3G | GLF 14 - diabetes | 146,212 | Mar. 26, 2004 | TABLE3G.TXT |
| 13 | 3H | GLF 15 - hyperlipidemia | 165,909 | Mar. 26, 2004 | TABLE3H.TXT |
| 14 | 3I | GLF 16 - lung | 92,936 | Mar. 25, 2004 | TABLE3I.TXT |
| 15 | 3J | GLF 17 - bladder | 1,143,423 | Mar. 26, 2004 | TABLE3J.TXT |
| 16 | 3K | GLF 18 - bladder | 953,119 | Mar. 26, 2004 | TABLE3K.TXT |
| 17 | 3L | GLF 19 - Coronary Art Dis. | 246,178 | Mar. 26, 2004 | TABLE3L.TXT |
| 18 | 3M | GLF 20 - rheumarth | 329,672 | Mar. 26, 2004 | TABLE3M.TXT |
| 19 | 3N | GLF 21 - depression | 153,108 | Mar. 26, 2004 | TABLE3N.TXT |
| 20 | 3O | GLF 22 - rheumarth | 49,043 | Mar. 26, 2004 | TABLE3O.TXT |
| 21 | 3P | GLF hypertension 577 only | 84,945 | Mar. 26, 2004 | TABLE3P.TXT |
| 22 | 3Q | GLF OA hypertension shared | 33,081 | Mar. 26, 2004 | TABLE3Q.TXT |
| 23 | 3R | GL obesity 519 | 79,544 | Mar. 26, 2004 | TABLE3R.TXT |
| 24 | 3S | GL obesity shared 152 | 24,583 | Mar. 26, 2004 | TABLE3S.TXT |
| 25 | 3T | GL allergy specific | 39,547 | Mar. 25, 2004 | TABLE3T.TXT |
| 26 | 3U | GL allergy OA shared 241 | 35,603 | Mar. 25, 2004 | TABLE3U.TXT |
| 27 | 3V | GL steroid 362 | 54,954 | Mar. 26, 2004 | TABLE3V.TXT |
| 28 | 3W | GL OA steroid shared | 31,459 | Mar. 27, 2004 | TABLE3W.TXT |
| 29 | 3X | GLF 26 - liver cancer | 435,093 | Mar. 27, 2004 | TABLE3X.TXT |
| 30 | 3Y | GLF 27 - schizophrenia | 578,949 | Mar. 26, 2004 | TABLE3Y.TXT |
| 31 | 3Z | GLF 28 - chagas | 202,477 | Mar. 28, 2004 | TABLE3Z.TXT |
| 32 | 4 | sequence listing | 114,765 | Mar. 11, 2004 | TABLE4.TXT |

BACKGROUND

The blood is a vital part of the human circulatory system for the human body. Numerous cell types make up the blood tissue including monocytes, leukocytes, lymphocytes and erythrocytes. Although many blood cell types have been described, there are likely many as yet undiscovered cell types in the human blood. Some of these undiscovered cells may exist transiently, such as those derived from tissues and organs that are constantly interacting with the circulating blood in health and disease. Thus, the blood can provide an immediate picture of what is happening in the human body at any given time.

The turnover of cells in the hematopoietic system is enormous. It was reported that over one trillion cells, including 200 billion erythrocytes and 70 billion neutrophilic leukocytes, turn over each day in the human body (Ogawa 1993). As a consequence of continuous interactions between the blood and the body, genetic changes that occur within the cells or tissues of the body will trigger specific changes in gene expression within blood. It is the goal of the present invention that these genetic alterations be harnessed for diagnostic and prognostic purposes, which may lead to the development of therapeutics for ameliorating disease.

For example, isoformic myosin heavy chain genes are known to be generally expressed in cardiac muscle tissue. In the rodent, the βMyHC gene is only highly expressed in the fetus and in diseased states such as overt cardiac hypertrophy, heart failure and diabetes; the αMyHC gene is highly expressed shortly after birth and continues to be expressed in the adult heart. In the human, however, βMyHC is highly expressed in the ventricles from the fetal stage through adulthood. This highly expressed βMyHC, which harbours several mutations, has been demonstrated to be involved in familial hypertrophic cardiomyopathy (Geisterfer-Lowrance et al. 1990). It was reported that mutations of βMyHC can be detected by PCR using blood lymphocyte DNA (Ferrie et al., 1992). Most recently, it was also demonstrated that mutations of the myosin-binding protein C in familial hypertrophic cardiomyopathy can be detected in the DNA extracted from lymphocytes (Niimura et al., 1998).

Similarly, APP and APC, which are known to be tissue specific and predominantly expressed in the brain and intestinal tract, are also detectable in the transcripts of blood. These cell- or tissue-specific transcripts are not detectable by Northern blot analysis. However, the low number of transcript copies can be detected by RT-PCR analysis. These findings strongly demonstrate that genes preferentially expressed in specific tissues can be detected by a highly sensitive RT-PCR assay. In recent years, evidence has been obtained to indicate that expression of cell or tissue-restricted genes can be detected in the certain peripheral nucleated blood cells of patients with metastatic transitional cell carcinoma (Yuasa et al. 1998) and patients with prostate cancer (Gala et al. 1998).

In the prior art, there is a need for large samples and/or costly and time-consuming separation of cell types within the blood (Kimoto (1998) and Chelly et al. (1989; 1988)). The prior art, however, is deficient in non-invasive methods of screening for tissue-specific diseases. The present invention fulfills this long-standing need and desire in the art.

SUMMARY OF THE INVENTION

The present invention relates generally to the molecular biology of human diseases. More specifically, the present invention relates to a process using the genetic information contained in human peripheral whole blood for the diagnosis, prognosis and monitoring of genetic and infectious disease in the human body.

This present invention discloses a process of using the genetic information contained in human peripheral whole blood in the diagnosis, prognosis and monitoring of genetic and infectious disease in the human body. The process described herein requires a simple blood sample and is, therefore, non-invasive compared to conventional practices used to detect tissue specific disease, such as biopsies.

The invention is based on the discovery that gene expression in the blood is reflective of body state and, as such, the resultant disruption of homeostasis under conditions of disease can be detected through analysis of transcripts differentially expressed in the blood alone. Thus, the identification of several key transcripts or genetic markers in blood will provide information about the genetic state of the cells, tissues, organ systems of the human body in health and disease.

The present invention demonstrates that a simple drop of blood may be used to determine the quantitative expression of various mRNAs that reflect the health/disease state of the subject through the use of RT-PCR analysis. This entire process takes about three hours or less. The single drop of blood may also be used for multiple RT-PCR analyses. It is believed that the present finding can potentially revolutionize the way that diseases are detected, diagnosed and monitored because it provides a non-invasive, simple, highly sensitive and quick screening for tissue-specific transcripts. The transcripts detected in whole blood have potential as prognostic or diagnostic markers of disease, as they reflect disturbances in homeostasis in the human body. Delineation of the sequences and/or quantitation of the expression levels of these marker genes by RT-PCR will allow for an immediate and accurate diagnostic/prognostic test for disease or to assess the efficacy and monitor a particular therapeutic.

One object of the present invention is to provide a non-invasive method for the diagnosis, prognosis and monitoring of genetic and infectious disease in humans and animals.

In one embodiment of the present invention, there is provided a method for detecting expression of a gene in blood from a subject, comprising the steps of: a) quantifying RNA from a subject blood sample; and b) detecting expression of the gene in the quantified RNA, wherein the expression of the gene in quantified RNA indicates the expression of the gene in the subject blood. An example of the quantifying method is by mass spectrometry.

In another embodiment of the present invention, there is provided a method for detecting expression of one or more genes in blood from a subject, comprising the steps of: a) obtaining a subject blood sample; b) extracting RNA from the blood sample; c) amplifying the RNA; d) generating expressed sequence tags (ESTs) from the amplified RNA product; and e) detecting expression of the genes in the ESTs, wherein the expression of the genes in the ESTs indicates the expression of the genes in the subject blood. Preferably, the subject is a fetus, an embryo, a child, an adult or a non-human animal. The genes are non-cancer-associated and tissue-specific genes. Still preferably, the amplification is performed by RT-PCR using random sequence primers or gene-specific primers.

In still another embodiment of the present invention, there is provided a method for detecting expression of one or more genes in blood from a subject, comprising the steps of: a) obtaining a subject blood sample; b) extracting DNA fragments from the blood sample; c) amplifying the DNA fragments; and d) detecting expression of the genes in the amplified DNA product, wherein the expression of the genes in the amplified DNA product indicates the expression of the genes in the subject blood.

In yet another embodiment of the present invention, there is provided a method for monitoring a course of a therapeutic treatment in an individual, comprising the steps of: a) obtaining a blood sample from the individual; b) extracting RNA from the blood sample; c) amplifying the RNA; d) generating expressed sequence tags (ESTs) from the amplified RNA product; e) detecting expression of genes in the ESTs, wherein the expression of the genes is associated with the effect of the therapeutic treatment; and f) repeating steps a)-e), wherein the course of the therapeutic treatment is monitored by detecting the change of expression of the genes in the ESTs. Such a method may also be used for monitoring the onset of overt symptoms of a disease, wherein the expression of the genes is associated with the onset of the symptoms. Preferably, the amplification is performed by RT-PCR, and the change of the expression of the genes in the ESTs is monitored by sequencing the ESTs and comparing the resulting sequences at various time points; or by performing single nucleotide polymorphism analysis and detecting the variation of a single nucleotide in the ESTs at various time points.

In still yet another embodiment of the present invention, there is provided a method for diagnosing a disease in a test subject, comprising the steps of: a) generating a cDNA library for the disease from a whole blood sample from a normal subject; b) generating expressed sequence tag (EST) profile from the normal subject cDNA library; c) generating a cDNA library for the disease from a whole blood sample from a test subject; d) generating EST profile from the test subject cDNA library; and e) comparing the test subject EST profile to the normal subject EST profile, wherein if the test subject EST profile differs from the normal subject EST profile, the test subject might be diagnosed with the disease.

In still yet another embodiment of the present invention, there is provided a kit for diagnosing, prognosing or predicting a disease, comprising: a) gene-specific primers; wherein the primers are designed in such a way that their sequences contain the opposing ends of two adjacent exons for the specific gene with the intron sequence excluded; and b) a carrier, wherein the carrier immobilizes the primer(s). Preferably, the gene-specific primers are selected from the group consisting of insulin-specific primers, atrial natriuretic factor-specific primers, zinc finger protein gene-specific primers, beta-myosin heavy chain gene-specific primers, amyloid precursor protein gene-specific primers, and adenomatous polyposis-coli protein gene-specific primers. Further preferably, the gene-specific primers are selected from the group consisting of SEQ ID Nos. 1 and 2; and SEQ ID Nos. 5 and 6. Such a kit may be applied to a test subject whole blood sample to diagnose, prognose or predict a disease by detecting the quantitative expression levels of specific genes associated with the disease in the test subject and then comparing to the levels of same genes expressed in a normal subject. Such a kit may also be used for monitoring a course of therapeutic treatment or monitoring the onset of overt symptoms of a disease.

In yet another embodiment of the present invention, there is provided a kit for diagnosing, prognosing or predicting a disease, comprising: a) probes derived from a whole blood sample for a specific disease; and b) a carrier, wherein the carrier immobilizes the probes. Such a kit may be applied to a test subject whole blood sample to diagnose, prognose or predict a disease by detecting the quantitative expression levels of specific genes associated with the disease in the test subject and then comparing to the levels of same genes expressed in a normal subject. Such a kit may also be used for monitoring a course of therapeutic treatment or monitoring the onset of overt symptoms of a disease.

Furthermore, the present invention provides a cDNA library specific for a disease, wherein the cDNA library is generated from whole blood samples.

In one embodiment of the present invention, there is a method of identifying one or more genetic markers for a disease, wherein each of said one or more genetic markers corresponds to a gene transcript, comprising the steps of: a) determining the level of one or more gene transcripts expressed in blood obtained from one or more individuals having a disease, wherein each of said one or more transcripts is expressed by a gene that is a candidate marker for disease; and b) comparing the level of each of said one or more gene transcripts from said step a) with the level of each of said one or more genes transcripts in blood obtained from one or more individuals not having a disease, wherein those compared transcripts which display differing levels in the comparison of step b) are identified as being genetic markers for a disease.

In another embodiment of the present invention, there is a method of identifying one or more genetic markers for a disease, wherein each of said one or more genetic markers corresponds to a gene transcript, comprising the steps of: a) determining the level of one or more gene transcripts expressed in blood obtained from one or more individuals having a disease, wherein each of said one or more transcripts is expressed by a gene that is a candidate marker for a disease; and b) comparing the level of each of said one or more gene transcripts from said step a) with the level of each of said one or more genes transcripts in blood obtained from one or more individuals having a disease, wherein those compared transcripts which display the same levels in the comparison of step b) are identified as being genetic markers for a disease.

In another embodiment of the present invention, there is a method of identifying one or more genetic markers of a stage of a disease progression or regression, wherein each of said one or more genetic markers corresponds to a gene transcript, comprising the steps of: a) determining the level of one or more gene transcripts expressed in blood obtained from one or more individuals having a stage of a disease, wherein said one or more individuals are at the same progressive or regressive stage of a disease, and wherein each of said one or more transcripts is expressed by a gene that is a candidate marker for determining the stage of progression or regression of a disease, and; b) comparing the level of each of said one or more gene transcripts from said step a) with the level of each of said one or more genes transcripts in blood obtained from one or more individuals who are at a progressive or regressive stage of a disease distinct from that of said one or more individuals of step a), wherein those compared transcripts which display differing levels in the comparison of step b) are identified as being genetic markers for the stage of progression or regression of a disease.

In another embodiment of the present invention, there is a method of identifying one or more genetic markers of a stage of a disease progression or regression, wherein each of said one or more genetic markers corresponds to a gene transcript, comprising the steps of: a) determining the level of one or more gene transcripts expressed in blood obtained from one or more individuals having a stage of a disease, wherein said one or more individuals are at the same progressive or regressive stage of a disease, and wherein each of said one or more transcripts is expressed by a gene that is a candidate marker for determining the stage of progression or regression of a disease, and b) comparing the level of each of said one or more gene transcripts from said step a) with the level of each of said one or more genes transcripts in blood obtained from one or more individuals who are at a progressive or regressive stage of a disease identical to that of said one or more individuals of step a), wherein those compared transcripts which display the same levels in the comparison of step b) are identified as being genetic markers for the stage of progression or regression of a disease.

Further embodiments of the methods described in the previous four paragraphs include the embodiments wherein each of said one or more markers identifies one or more transcripts of one or more non immune response genes, wherein each of said one or more markers identifies a transcript of a gene expressed by non-blood tissue, wherein each of said one or more markers identifies a transcript of a gene expressed by non-lymphoid tissue, wherein said one or more markers identifies a sequence selected from the sequences listed in any one of Table 3A-Z and Tables 3AA, 3AB, 3AC and 3AD, wherein said one or more markers identifies the sequence of one or more of the sequences selected from the group consisting of ANF, ZFP and βMyHC, wherein said blood comprises a blood sample obtained from said one or more individuals, wherein said blood sample consists of whole blood, wherein said blood sample consists of a drop of blood, and wherein said blood sample consists of blood that has been lysed.

In another embodiment of the present invention, there is a method of diagnosing or prognosing a disease in an individual, comprising the steps of: a) determining the level of one or more gene transcripts in blood obtained from said individual suspected of having a disease, and b) comparing the level of each of said one or more gene transcripts in said blood according to step a) with the level of each of said one or more gene transcripts in blood from one or more individuals not having a disease, wherein detecting a difference in the levels of each of said one or more gene transcripts in the comparison of step b) is indicative of a disease in the individual of step a).

In another embodiment of the present invention, there is a method of diagnosing or prognosing a disease in an individual, comprising the steps of: a) determining the level of one or more gene transcripts in blood obtained from said individual suspected of having a disease, and b) comparing the level of each of said one or more gene transcripts in said blood according to step a) with the level of each of said one or more gene transcripts in blood from one or more individuals having a disease, wherein detecting the same levels of each of said one or more gene transcripts in the comparison of step b) is indicative of a disease in the individual of step a).

In another embodiment of the present invention, there is a method of determining a stage of disease progression or regression in an individual having a disease, comprising the steps of: a) determining the level of one or more gene transcripts in blood obtained from said individual having a disease, and b) comparing the level of each if said one or more gene transcripts in said blood according to step a) with the level of each of said one or more gene transcripts in blood obtained from one or more individuals who each have been diagnosed as being at the same progressive or regressive stage of a disease, wherein the comparison from step b) allows the determination of the stage of a disease progression or regression in an individual.

In another embodiment of the present invention, there is a method of diagnosing or prognosing osteoarthritis in an individual, comprising the steps of: a) determining the level of one or more gene transcripts expressed in blood obtained from said individual, wherein said one or more gene transcripts correspond to said one or more markers of claim 1 and claim 2, and b) comparing the level of each of said one or more gene transcripts in said blood according to step a) with the level of each of said one or more gene transcripts in blood from one or more individuals having osteoarthritis, c) comparing the level of each of said one or more gene transcripts in said blood according to step a) with the level of each of said one or more gene transcripts in blood from one or more individuals not having osteoarthritis, d) determining whether the level of said one or more gene transcripts of step a) classify with the levels of said transcripts in step b) as compared with the levels of said transcripts in step c) wherein said determination is indicative of said individual of step a) having osteoarthritis.

In another embodiment of the present invention, there is a method of determining a stage of disease progression or regression in an individual having osteoarthritis, comprising the steps of: a) determining the level of one or more gene transcripts expressed in blood obtained from said individual having said stage of osteoarthritis, wherein said one or more gene transcripts correspond to the markers of claim 3 and claim 4, and b) comparing the level of each of said one or more gene transcripts in said blood according to step a) with the level of each of said one or more gene transcripts in blood from one or more individuals having said stage of osteoarthritis, c) comparing the level of each of said one or more gene transcripts in said blood according to step a) with the level of each of said one or more gene transcripts in blood from one or more individuals not having said stage of osteoarthritis, d) determining whether the level of said one or more gene transcripts of step a) classify with the levels of said transcripts in step b) as compared with levels of said transcripts in step c), wherein said determination is indicative of said individual of step a) having said stage of osteoarthritis.

Further embodiments of the methods described in the previous ten paragraphs include embodiments comprising a further step of isolating RNA from said blood samples, and embodiments comprising determining the level of each of said one or more gene transcripts comprising quantitative RT-PCR (QRT-PCR), wherein said one or more transcripts are from step a) and/or step b) of said methods. Further embodiments of these methods include embodiments wherein said QRT-PCR comprises primers which hybridize to one or more transcripts or the complement thereof, wherein said one or more transcripts are from step a) and/or step b) of said methods, embodiments wherein said primers are 15-25 nucleotides in length, and embodiments wherein said primers hybridize to one or more of the sequences of any one of Table 3A-Z and Tables 3AA, 3AB, 3AC and 3AD, or the complement thereof. Further embodiments of the methods described in the previous eight paragraphs include embodiments wherein the step of determining the level of each of said one or more gene transcripts comprises hybridizing a first plurality of isolated nucleic acid molecules that correspond to said one or more transcripts to an array comprising a second plurality of isolated nucleic acid molecules, wherein in one embodiment said first plurality of isolated nucleic acid molecules comprises RNA, DNA, cDNA, PCR products or ESTs, wherein in one embodiment said array comprises a plurality of isolated nucleic acid molecules comprising RNA, DNA, cDNA, PCR products or ESTs, wherein in one embodiment said array comprises two or more of the genetic markers of said methods, wherein in one embodiment said array comprises a plurality of nucleic acid molecules that correspond to genes of the human genome.

In another embodiment of the present invention, there is a plurality of nucleic acid molecules that correspond to two or more sequences from each of any one of Table 3A-Z and Tables 3AA, 3AB, 3AC and 3AD.

In another embodiment of the present invention, there is an array which comprises a plurality of nucleic acid molecules that correspond to two or more sequences from each of any one of Table 3A-Z and Tables 3AA, 3AB, 3AC and 3AD.

In another embodiment of the present invention, there is a kit for diagnosing or prognosing a disease comprising: a) two gene-specific priming means designed to produce double stranded DNA complementary to a gene selected from the group consisting of Table 3L; wherein said first priming means contains a sequence which can hybridize to RNA, cDNA or an EST complementary to said gene to create an extension product and said second priming means capable of hybridizing to said extension product; b) an enzyme with reverse transcriptase activity c) an enzyme with thermostable DNA polymerase activity and d) a labeling means; wherein said primers are used to detect the quantitative expression levels of said gene in a test subject In another embodiment of the present invention, there is a kit for monitoring a course of therapeutic treatment of a disease, comprising a) two gene-specific priming means designed to produce double stranded DNA complementary to a gene selected group consisting of any one of Table 3A-Z and Tables 3AA, 3AB, 3AC and 3AD; wherein said first priming means contains a sequence which can hybridize to RNA, cDNA or an EST complementary to said gene to create an extension product and said second priming means capable of hybridizing to said extension product; b) an enzyme with reverse transcriptase activity c) an enzyme with thermostable DNA polymerase activity and d) a labeling means; wherein said primers are used to detect the quantitative expression levels of said gene in a test subject.

In another embodiment of the present invention, there is a kit for monitoring progression or regression of a disease, comprising: a) two gene-specific priming means designed to produce double stranded DNA complementary to a gene selected group consisting of any one of Table 3A-Z and Tables 3AA, 3AB, 3AC and 3AD; wherein said first priming means contains a sequence which can hybridize to RNA, cDNA or an EST complementary to said gene to create an extension product and said second priming means capable of hybridizing to said extension product; b) an enzyme with reverse transcriptase activity c) an enzyme with thermostable DNA polymerase activity and d) a labeling means; wherein said primers are used to detect the quantitative expression levels of said gene in a test subject.

In another embodiment of the present invention, there is a plurality of nucleic acid molecules that identify or correspond to two or more sequences from any one of Table 3A-Z and Tables 3AA, 3AB, 3AC and 3AD.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A: Lane 1, Molecular weight marker; Lane 2, RT-PCR on APP gene; Lane 3, PCR on APP gene; Lane 4, RT-PCR on APC gene; Lane 5, PCR on APC gene; FIG. 1B: Lanes 1 and 2, RT-PCR and PCR of βMyHC, respectively; Lanes 3 and 4, RT-PCR of βMyHC from RNA prepared from human fetal and human adult heart, respectively; Lane 5, Molecular weight marker.

FIG. 5 shows standardized levels of insulin gene (FIG. 5A) and ZFP gene (FIG. 5B) expressed in a drop of blood. The first three subjects were normal, second two subjects showed normal glucose tolerance, and the last subject had late onset diabetes type II. FIG. 5C shows standardized levels of insulin gene expressed in each fractionated cell from whole blood.

FIG. 6 shows the differential screening of human blood cell cDNA library with different cDNA probes of heart and brain tissue. FIG. 6A shows blood cell cDNA probes vs. adult heart cDNA probes. FIG. 6B shows blood cell cDNA probes vs. human brain cDNA probes.

FIG. 7 graphically shows the 1,800 unique genes in human blood and in the human fetal heart grouped into seven cellular functions.

DETAILED DESCRIPTION

Figure 1:
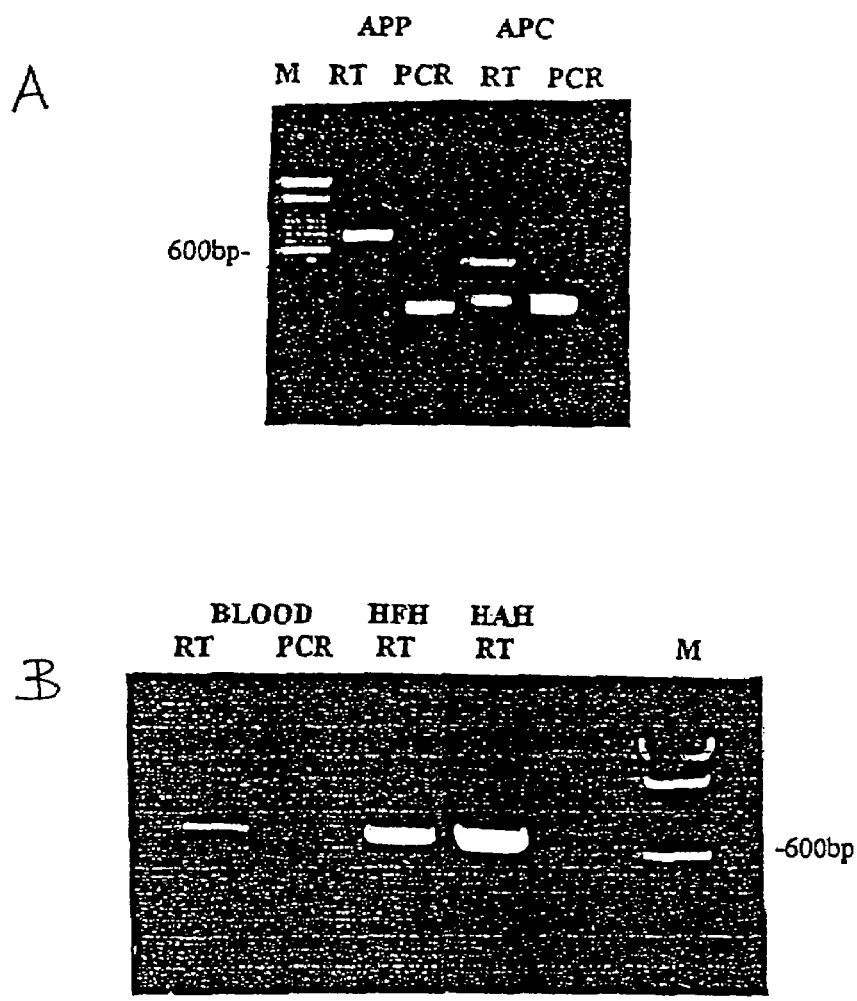
FIG. 1 shows the following RNA samples prepared from human blood.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "cDNA" is defined as copy-DNA or complementary-DNA, and is a product of a reverse transcription reaction from an mRNA transcript. "RT-PCR" refers to reverse transcription polymerase chain reaction and results in production of cDNAs that are complementary to the mRNA template(s).

In addition to RT-PCR, other methods of amplifying may also be used for the purpose of measuring/quantitating tissue-specific transcripts in human blood. For example, mass spectrometry may be used to quantify the transcripts (Koster et al., 1996; Fu et al., 1998). The application of presently disclosed method for detecting tissue-specific transcripts in blood does not restrict to subjects undergoing course of therapy or treatment, it may also be used for monitoring a patient for the onset of overt symptoms of a disease. Furthermore, the present method may be used for detecting any gene transcripts in blood. A kit for diagnosing, prognosing or even predicting a disease may be designed using gene-specific primers or probes derived from a whole blood sample for a specific disease and applied directly to a drop of blood. A cDNA library specific for a disease may be generated from whole blood samples and used for diagnosis, prognosis or even predicting a disease.

The term "oligonucleotide" is defined as a molecule comprised of two or more deoxyribonucleotides and/or ribonucleotides, preferably more than three. Its exact size will depend upon many factors which, in turn, depend upon the ultimate function and use of the oligonucleotide. The upper limit may be 15, 20, 25, 30, 40 or 50 nucleotides in length. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art.

As used herein, random sequence primers refer to a composition of primers of random sequence, i.e. not directed towards a specific sequence. These sequences possess sufficient complementary to hybridize with a polynucleotide and the primer sequence need not reflect the exact sequence of the template.

"Restriction fragment length polymorphism" refers to variations in DNA sequence detected by variations in the length of DNA fragments generated by restriction endonuclease digestion.

A standard Northern blot assay can be used to ascertain the relative amounts of mRNA in a cell or tissue obtained from plant or other tissue, in accordance with conventional Northern hybridization techniques known to those persons of ordinary skill in the art. The Northern blot uses a hybridization probe, e.g. radiolabelled cDNA, either containing the full-length, single stranded DNA or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labelled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, "individual" refers to human subjects as well as non-human subjects. The examples herein are not meant to limit the methodology of the present invention to human subjects only, as the instant methodology is useful in the fields of veterinary medicine, animal sciences and such. The term "individual" refers to human subjects and non-human subjects who are disease or condition free and also includes human and non-human subjects diagnosed with one or more diseases or conditions, as defined herein. "Co-morbid individuals" or "comorbidity" or "individuals considered as co-morbid" are individuals who have more than one disease or condition as defined herein. For example a patient diagnosed with both osteoarthritis and hypertension is considered to present with comorbidities.

As used herein, "detecting" refers to determining the presence of a gene expression product, for example cDNA, RNA or EST, by any method known to those of skill in the art or taught in numerous texts and laboratory manuals (see for example, Ausubel et al. Short Protocols in Molecular Biology (1995) 3rd Ed. John Wiley & Sons, Inc.). For example, methods of detection include but are not limited to, RNA fingerprinting, Northern blotting, polymerase chain reaction, ligase chain reaction, Qbeta replicase, isothermal amplification method, strand displacement amplification, transcription based amplification systems, nuclease protection (SI nuclease or RNAse protection assays) as well as methods disclosed in WO88/10315, WO89/06700, PCT/US87/00880, PCT/US89/01025.

As used herein, a disease of the invention includes, but is not limited to, blood disorder, blood lipid disease, autoimmune disease, arthritis (including osteoarthritis, rheumatoid arthritis, lupus, allergies, juvenile rheumatoid arthritis and the like), bone or joint disorder, a cardiovascular disorder (including heart failure, congenital heart disease; rheumatic fever, valvular heart disease; corpulmonale, cardiomyopathy, myocarditis, pericardial disease; vascular diseases such as atherosclerosis, acute myocardial infarction, ischemic heart disease and the like), obesity, respiratory disease (including asthma, pneumonitis, pneumonia, pulmonary infections, lung disease, bronchiectasis, tuberculosis, cystic fibrosis, interstitial lung disease, chronic bronchitis emphysema, pulmonary hypertension, pulmonary thromboembolism, acute respiratory distress syndrome and the like), hyperlipidemias, endocrine disorder, immune disorder, infectious disease, muscle wasting and whole body wasting disorder, neurological disorders (including migraines, seizures, epilepsy, cerebrovascular diseases, alzheimers, dementia, Parkinson's, ataxic disorders, motor neuron diseases, cranial nerve disorders, spinal cord disorders, meningitis and the like) including neurodegenerative and/or neuropsychiatric diseases and mood disorders (including schizophrenia, anxiety, bipolar disorder; manic depression and the like, skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others) and the like. For further discussion of human diseases, see Mendelian Inheritance in Man: A Catalog of Human Genes and Genetic Disorders by Victor A. McKusick (12th Edition (3 volume set) June 1998, Johns Hopkins University Press, ISBN: 0801857422) and Harrison's Principles of Internal Medicine by Braunwald, Fauci, Kasper, Hauser, Longo, & Jameson (15th Edition, 2001), the entirety of which is incorporated herein.

In another embodiment of the invention, a disease refers to an immune disorder, such as those associated with overexpression of a gene or expression of a mutant gene (e.g., autoimmune diseases, such as diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, a disease of the invention is a cellular proliferative and/or differentiative disorder that includes, but is not limited to, cancer e.g., carcinoma, sarcoma or other metastatic disorders and the like. As used herein, the term "cancer" refers to cells having the capacity for autonomous growth, i.e., an abnormal state of condition characterized by rapidly proliferating cell growth. "Cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumour, in situ, Krebs 2, Merkel cell, mucinous, non-small cell lung, oat cell, papillary, scirrhous, bronchiolar, bronchogenic, squamous cell, and transitional cell), histiocytic disorders, leukaemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumour, adeno-carcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, mymoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic respiratory tract, and urogenital), neurofibromatosis, and cervical dysplasia, and other conditions in which cells have become immortalized or transformed.

In another embodiment, a disease of the invention includes but is not limited to a condition wherein said condition is reflective of the state of a particular individual, whether said state is a physical, emotional or psychological state, said state resulting from the progression of time, treatment, environmental factors or genetic factors.

As used herein, a gene of the invention is a gene that is expressed in blood and is either upregulated, or downregulated and can be used, either solely or in conjunction with other genes, as a marker for disease as defined herein. By a gene that is expressed in blood or in a blood sample is meant a gene that is expressed in the cells which typically make up blood including monocytes, leukocytes, lymphocytes and erythrocytes, all other cells derived directly from haemopoietic or mesenchymal stem cells, or derived directly from a cell which typically makes up the blood.

The term "gene" includes a region that can be transcribed into RNA, as the invention contemplates detection of RNA or equivalents thereof, i.e., cDNA or EST. A gene of the invention includes but is not limited to genes specific for or involved in a particular biological process, such as apoptosis, differentiation, stress response, aging, proliferation, etc.; cellular mechanism genes, e.g. cell-cycle, signal transduction, metabolism of toxic compounds, and the like; disease associated genes, e.g. genes involved in cancer, schizophrenia, diabetes, high blood pressure, atherosclerosis, viral-host interaction and infection and the like.

For example, the gene of the invention can be an oncogene (Hanahan, D. and R. A. Weinberg, Cell (2000) 100:57; and Yokota, J., Carcinogenesis (2000) 21(3):497-503) whose expression within a cell induces that cell to become converted from a normal cell into a tumor cell. Further examples of genes of the invention include, but are not limited to, cytokine genes (Rubinstein, M., et al., Cytokine Growth Factor Rev. (1998) 9(2):175-81); idiotype (Id) protein genes (Benezra, R., et al., Oncogene (2001) 20(58):8334-41; Norton, J. D., J. Cell Sci. (2000) 113(22):3897-905); prion genes (Prusiner, S. B., et al., Cell (1998) 93(3):337-48; Safar, J., and S. B. Prusiner, Prog., Brain Res., (1998) 117:421-34); genes that express molecules that induce angiogenesis (Gould, V. E. and B. M. Wagner, Hum. Pathol. (2002) 33(11):1061-3); genes encoding adhesion molecules (Chothia, C. and E. Y. Jones, Annu. Rev. Biochem. (1997) 66:823-62; Parise, L. V., et al., Semin. Cancer Biol. (2000) 10(6):407-14); genes encoding cell surface receptors (Deller, M. C., and Y. E. Jones, Curr. Opin. Struct. Biol. (2000) 10(2):213-9); genes of proteins that are involved in metastasizing and/or invasive processes (Boyd, D., Cancer Metastasis Rev. (1996) 15(1):77-89; Yokota, J., Carcinogenesis (2000) 21(3):497-503); genes of proteases as well as of molecules that regulate apoptosis and the cell cycle (Matrisian, L. M., Curr. Biol. (1999) 9(20): R776-8; Krepela, E., Neoplasma (2001) 48(5):332-49; Basbaum and Werb, Curr. Opin. Cell Biol. (1996) 8:731-738; Birkedal-Hansen, et al., Crit. Rev. Oral Biol. Med. (1993) 4:197-250; Mignatti and Rifkin, Physiol. Rev. (1993) 73:161-195; Stetler-Stevenson, et al., Annu., Rev. Cell Biol., (1993) 9:541-573; Brinkerhoff, E., and L. M. Matrisan, Nature Reviews (2002) 3:207-214; Strasser, A., et al., Annu., Rev. Biochem., (2000), 69:217-45; Chao, D. T. and S. J. Korsmeyer, Annu. Rev. Immunol. (1998) 16:395-419; Mullauer, L., et al., Mutat. Res. (2001) 488(3):211-31; Fotedar, R., et al., Prog., Cell Cycle Res., (1996), 2:147-63; Reed, J. C., Am. J. Pathol., (2000) 157(5):1415-30; D'Ari, R., Bioassays (2001) 23(7):563-5); or multi-drug resistance genes, such as MDR1 gene (Childs, S., and V. Ling, Imp., Adv. Oncol., (1994) 21-36). In another embodiment, a gene of the invention contains a sequence found in Tables 2 or 3 or FIGS. 22-34. In another embodiment, a gene of the invention can be an immune response gene or a non-immune response gene. By an immune response gene is meant a primary defense response gene located outside the major histocompatibility region (MHC) that is initially triggered in response to a foreign antigen to regulate immune responsiveness. All other genes expressed in blood are considered to be non-immune response gene. For example, an immune response gene would be understood by a person skilled in the art to include: cytokines including interleukins and interferons such as TNF-alpha, IL-10, IL-12, IL-2, IL-4, IL-10, IL-12, IL-13, TGF-Beta, IFN-gamma; immunoglobulins, complement and the like (see for example Bellardelli, F. Role of interferons and other cytokines in the regulation of the immune response APMIS., 1995, March; 103(3): 161-79;).

Construction of a Microarray

A nucleic acid microarray (RNA, DNA, cDNA, PCR products or ESTs) according to the invention was constructed as follows:

Nucleic acids (RNA, DNA, cDNA, PCR products or ESTs) (~40 μl) are precipitated with 4 μl (1/10 volume) of 3M sodium acetate (pH 5.2) and 100 μl (2.5 volumes) of ethanol and stored overnight at −20° C. They are then centrifuged at 3,300 rpm at 4° C. for 1 hour. The obtained pellets were washed with 50 μl ice-cold 70% ethanol and centrifuged again for 30 minutes. The pellets are then air-dried and resuspended well in 50% dimethylsulfoxide (DMSO) or 20 μl 3×SSC overnight. The samples are then deposited either singly or in duplicate onto Gamma Amino Propyl Silane (Corning CMT-GAPS or CMT-GAP2, Catalog No. 40003, 40004) or polylysine-coated slides (Sigma Cat. No. P0425) using a robotic GMS 417 or 427 arrayer (Affymetrix, Calif.). The boundaries of the DNA spots on the microarray are marked with a diamond scriber. The invention provides for arrays where 10-20,000 different DNAs are spotted onto a solid support to prepare an array, and also may include duplicate or triplicate DNAs.

The arrays are rehydrated by suspending the slides over a dish of warm particle free ddH20 for approximately one minute (the spots will swell slightly but not run into each other) and snap-dried on a 70-80° C. inverted heating block for 3 seconds. DNA is then UV crosslinked to the slide (Stratagene, Stratalinker, 65 mJ—set display to "650" which is 650×100 μJ, or baked at 80° C. for two to four hours. The arrays are placed in a slide rack. An empty slide chamber is prepared and filled with the following solution: 3.0 grams of succinic anhydride (Aldrich) is dissolved in 189 ml of 1-methyl-2-pyrrolidinone (rapid addition of reagent is crucial); immediately after the last flake of succinic anhydride dissolved, 21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. ddH$_2$0 for 2 minutes, followed by plunging five times in 95% ethanol. The slides are then air dried by allowing excess ethanol to drip onto paper towels. The arrays are then stored in the slide box at room temperature until use.

Nucleic Acid Microarrays

Any combination of the nucleic acid sequences generated from nucleotides complimentary to regions of DNA expressed in blood are used for the construction of a microarray. In one embodiment, the microarray is chondrocyte-specific and encompasses genes which are important in the osteoarthritis disease process. A microarray according to the invention preferably comprises between 10, 100, 500, 1000, 5000, 10,000 and 15,000 nucleic acid members, and more preferably comprises at least 5000 nucleic acid members. The nucleic acid members are known or novel nucleic acid sequences described herein, or any combination thereof. A microarray according to the invention is used to assay for differential gene expression profiles of genes in blood samples from healthy patients as compared to patients with a disease.

Microarray Used According to the Invention

The Human Genome U133 (HG-U133) Set, consisting of two GeneChip® arrays, contains almost 45,000 probe sets representing more than 39,000 transcripts derived from approximately 33,000 well-substantiated human genes. This set design uses sequences selected from GenBank®, dbEST, and RefSeq.

The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release).

The HG-U133A Array includes representation of the RefSeq database sequences and probe sets related to sequences previously represented on the Human Genome U95Av2 Array. The HG-U133B Array contains primarily probe sets representing EST clusters.

15 K ChondroChip™—The ChondroChip™ is chondrocyte-specific microarray chip comprising 15,000 novel and known EST sequences of the chondrocyte from human chondrocyte-specific cDNA libraries.

Controls on the ChondroChip™—There are two types of controls used on microarrays. First, positive controls are genes whose expression level is invariant between different stages of investigation and are used to monitor:
 a) target DNA binding to the slide,
 b) quality of the spotting and binding processes of the target DNA onto the slide,
 c) quality of the RNA samples, and
 d) efficiency of the reverse transcription and fluorescent labelling of the probes.

Second, negative controls are external controls derived from an organism unrelated to and therefore unlikely to cross-hybridize with the sample of interest. These are used to monitor for:
 a) variation in background fluorescence on the slide, and
 b) non-specific hybridization.

There are currently 63 control spots on the ChondroChip™ consisting of:

| Type | No. |
|---|---|
| Positive Controls: | 2 |
| Alien DNA | 12 |
| *A. thaliana* DNA | 10 |
| Spotting Buffer | 41 |

Figure 24:
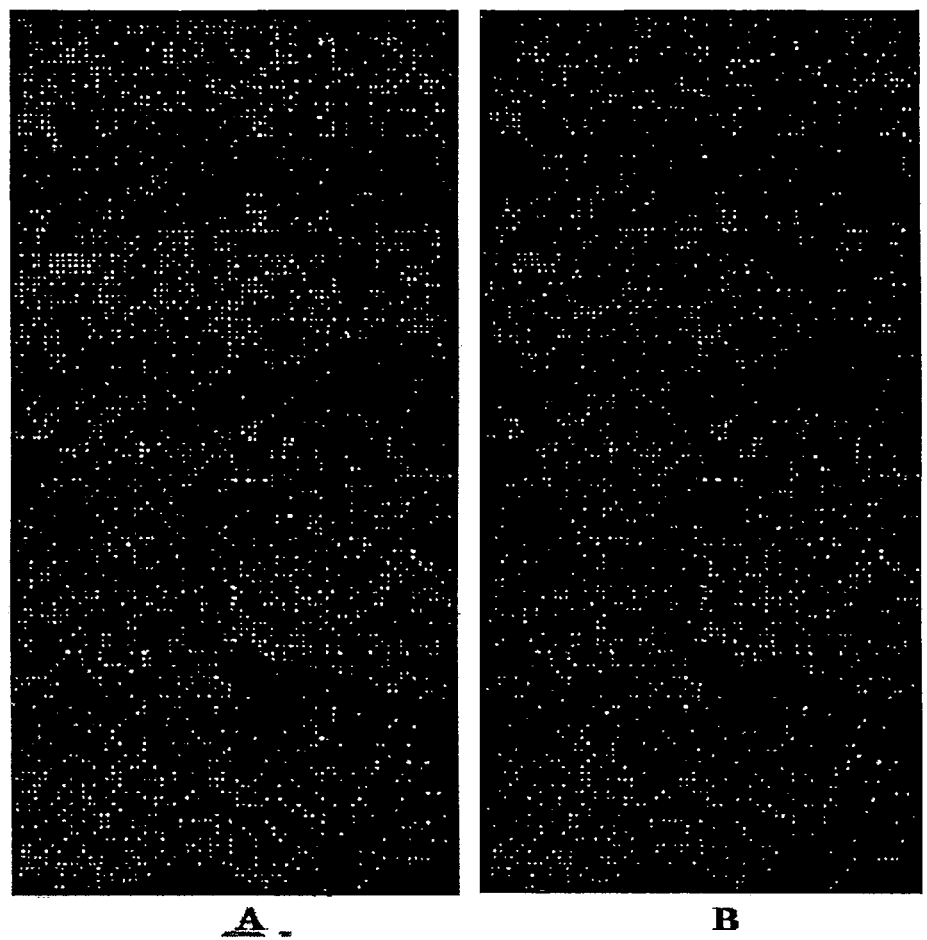
FIG. 24 shows the "Blood Chip", a cDNA microarray slide with 10,368 PCR products derived from peripheral blood cell cDNA libraries. Colors represent hybridization to probes labelled with Cy3 (green) or Cy5 (red). Yellow spots indicate common hybridization between both probes. In slide A, normal blood cell RNA samples were labelled with Cy3 and CAD blood cell RNA samples were labelled with Cy5. In slide B, Cy3 and Cy5 were switched to label the RNA samples. (Cluster analysis revealed distinct gene expression profiles for normal and CAD samples.)

BloodChip™—The "BloodChip™" is a cDNA microarray slide with 10,368 PCR products derived from peripheral blood cell cDNA libraries as shown in FIG. 24.

Target Nucleic Acid Preparation and Hybridization

Preparation of Fluorescent DNA Probe from mRNA

Fluorescently labelled target nucleic acid samples are prepared for analysis with an array of the invention.

2 μg Oligo-dT primers are annealed to 2 μg of mRNA isolated from a blood sample of a patient in a total volume of 15 μg, by heating to 70° C. for 10 min, and cooled on ice. The mRNA is reverse transcribed by incubating the sample at 42° C. for 1.5-2 hours in a 100 μg volume containing a final concentration of 50 mM Tris-HCl (pH 8.3), 75 mM KCl, 3 mM MgCl$_2$, 25 mM DTT, 25 mM unlabelled dNTPs, 400 units of Superscript II (200 U/μL, Gibco BRL), and 15 mM of Cy3 or Cy5 (Amersham). RNA is then degraded by addition of 15 μl of 0.1N NaOH, and incubation at 70° C. for 10 min. The reaction mixture is neutralized by addition of 15 μl of 0.1N HCl, and the volume is brought to 500 μl with TE (10 mM Tris, 1 mM EDTA), and 20 μg of Cot1 human DNA (Gibco-BRL) is added.

The labelled target nucleic acid sample is purified by centrifugation in a Centricon-30 micro-concentrator (Amicon). If two different target nucleic acid samples (e.g., two samples derived from a healthy patient vs. patient with a disease) are being analyzed and compared by hybridization to the same array, each target nucleic acid sample is labelled with a different fluorescent label (e.g., Cy3 and Cy5) and separately concentrated. The separately concentrated target nucleic acid samples (Cy3 and Cy5 labelled) are combined into a fresh centricon, washed with 500 μl TE, and concentrated again to a volume of less than 7 μl. 1 μl of 10 μg/μl polyA RNA (Sigma, #P9403) and 1 μl of 10 μg/μl tRNA (Gibco-BRL, #15401-011) is added and the volume is adjusted to 9.5 μl with distilled water. For final target nucleic acid preparation 2.1 μl 20×SSC (1.5M NaCl, 150 mM NaCitrate (pH8.0)) and 0.35 μL 10% SDS is added.

Hybridization

Labelled nucleic acid is denatured by heating for 2 min at 100° C., and incubated at 37° C. for 20-30 min before being placed on a nucleic acid array under a 22 mm×22 mm glass cover slip. Hybridization is carried out at 65° C. for 14 to 18 hours in a custom slide chamber with humidity maintained by a small reservoir of 3×SSC. The array is washed by submersion and agitation for 2-5 m in 2×SSC with 0.1% SDS, followed by 1×SSC, and 0.1×SSC. Finally, the array is dried by centrifugation for 2 min in a slide rack in a Beckman GS-6 tabletop centrifuge in Microplus carriers at 650 RPM for 2 min.

Signal Detection and Data Generation

Following hybridization of an array with one or more labelled target nucleic acid samples, arrays are scanned immediately using a GMS Scanner 418 and Scanalyzer software (Michael Eisen, Stanford University), followed by GeneSpring™ software (Silicon Genetics, CA) analysis. Alternatively, a GMS Scanner 428 and Jaguar software may be used followed by GeneSpring™ software analysis.

If one target nucleic acid sample is analyzed, the sample is labelled with one fluorescent dye (e.g., Cy3 or Cy5).

After hybridization to a microarray as described herein, fluorescence intensities at the associated nucleic acid members on the microarray are determined from images taken with a custom confocal microscope equipped with laser excitation sources and interference filters appropriate for the Cy3 or Cy5 fluorescence.

The presence of Cy3 or Cy5 fluorescent dye on the microarray indicates hybridization of a target nucleic acid and a specific nucleic acid member on the microarray. The intensity of Cy3 or Cy5 fluorescence represents the amount of target nucleic acid which is hybridized to the nucleic acid member on the microarray, and is indicative of the expression level of the specific nucleic acid member sequence in the target sample.

After hybridization, fluorescence intensities at the associated nucleic acid members on the microarray are determined from images taken with a custom confocal microscope equipped with laser excitation sources and interference filters appropriate for the Cy3 and Cy5 fluors. Separate scans are taken for each fluor at a resolution of 225 μm$^2$ per pixel and 65,536 gray levels. Normalization between the images is used to adjust for the different efficiencies in labeling and detection with the two different fluors. This is achieved by manual matching of the detection sensitivities to bring a set of internal control genes to nearly equal intensity followed by computational calculation of the residual scalar required for optimal intensity matching for this set of genes.

The presence of Cy3 or Cy5 fluorescent dye on the microarray indicates hybridization of a target nucleic acid and a specific nucleic acid member on the microarray. The intensities of Cy3 or Cy5 fluorescence represent the amount of target nucleic acid which is hybridized to the nucleic acid member on the microarray, and is indicative of the expression level of the specific nucleic acid member sequence in the target sample. If a nucleic acid member on the array shows no color, it indicates that the gene in that element is not expressed in either sample. If a nucleic acid member on the array shows a single color, it indicates that a labelled gene is expressed only in that cell sample. The appearance of both colors indicates that the gene is expressed in both tissue samples. The ratios of Cy3 and Cy5 fluorescence intensities, after normalization, are indicative of differences of expression levels of the associated nucleic acid member sequence in the two samples for comparison. A ratio of expression not equal to is used as an indication of differential gene expression.

The array is scanned in the Cy3 and Cy5 channels and stored as separate 16-bit TIFF images. The images are incorporated and analyzed using Scanalyzer software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A liner regression approach is used for normalization and assumes that a scatter plot of the measured Cy5 versus Cy3 intensities should have a scope of one. The average of the ratios is calculated and used to rescale the data and adjust the slope to one. A post-normalization cutoff of a ratio not equal to 1.0-is used to identify differentially expressed genes.

When comparing two or more samples for differences, results are reported as statistically significant when there is only a small probability that similar results would have been observed if the tested hypothesis (i.e., the genes are not expressed at different levels) were true. A small probability can be defined as the accepted threshold level at which the results being compared are considered significantly different. The accepted lower threshold is set at, but not limited to, 0.05 (i.e., there is a 5% likelihood that the results would be observed between two or more identical populations) such that any values determined by statistical means at or below this threshold are considered significant.

When comparing two or more samples for similarities, results are reported as statistically significant when there is only a small probability that similar results would have been observed if the tested hypothesis (i.e., the genes are not expressed at different levels) were true. A small probability can be defined as the accepted threshold level at which the results being compared are considered significantly different. The accepted lower threshold is set at, but not limited to, 0.05 (i.e., there is a 5% likelihood that the results would be observed between two or more identical populations) such that any values determined by statistical means above this threshold are not considered significantly different and thus similar.

Identification of genes differentially expressed in blood samples from patients with disease as compared to healthy patients or as compared to patients without said disease is determined by statistical analysis of the gene expression profiles from healthy patients or patients without disease compared to patients with disease using the Wilcox Mann Whitney rank sum test. Other statistical tests can also be used, see for example (Sokal and Rohlf (1987) Introduction to Biostatistics $2^{nd}$ edition, WH Freeman, New York), which is incorporated herein in their entirety.

In order to facilitate ready access, e.g. for comparison, review, recovery and/or modification, the expression profiles of patients with disease and/or patients without disease or healthy patients can be recorded in a database, whether in a relational database accessible by a computational device or other format, or a manually accessible indexed file of profiles as photographs, analogue or digital imaging, readouts spreadsheets etc. Typically the database is compiled and maintained at a central facility, with access being available locally and/or remotely.

As would be understood by a person skilled in the art, comparison as between the expression profile of a test patient with expression profiles of patients with a disease, expression profiles of patients with a certain stage or degree of progression of said disease, without said disease, or a healthy patient so as to diagnose or prognose said test patient can occur via expression profiles generated concurrently or non concurrently. It would be understood that expression profiles can be stored in a database to allow said comparison.

As additional test samples from test patients are obtained, through clinical trials, further investigation, or the like, additional data can be determined in accordance with the methods disclosed herein and can likewise be added to a database to provide better reference data for comparison of healthy and/or non-disease patients and/or certain stage or degree of progression of a disease as compared with the test patient sample.

Use of Expression Profiles for Diagnostic Purposes

As would be understood to a person skilled in the art, one can utilize sets of genes which have been identified as statistically significant as described above in order to characterize an unknown sample as having said disease or not having said disease. This is commonly termed "class prediction".

Methods that can be used for class prediction analysis have been well described and generally involve a training phase using samples with known classification and a testing phase from which the algorithm generalizes from the training data so as to predict classification of unknown samples (see for Example Slonim, D. (2002), Nature Genetics Supp., Vol. 32 502-8, Raychaudhuri et al., (2001) Trends Biotechnol., 19: 189-193; Khan et al. (2001) Nature Med., 7 673-9.; Golub et al. (1999) Science 286: 531-7. Hastie et al., (2000) Genome Biol., 1(2) Research 0003.1-0003.21, all of which are incorporated herein by reference in their entirety).

As additional samples are obtained, for example during clinical trials, their expression profiles can be determined and correlated with the relevant subject data in the database and likewise be recorded in said database. Algorithms as described above can be used to query additional samples against the existing database to further refine the diagnostic and/or prognostic determination by allowing an even greater association between the disease and gene expression signature.

The diagnosing or prognosing may thus be performed by detecting the expression level of two or more genes, three or more genes, four or more genes, five or more genes, six or more genes, seven or more genes, eight or more genes, nine or more genes, ten or more genes, fifteen or more genes, twenty or more genes thirty or more genes, fifty or more genes, one hundred or more genes, two hundred or more genes, three hundred or more genes, five hundred or more genes or all of the genes disclosed for the specific disease in question.

Data Acquisition and Analysis of Differentially Expressed EST Sequences

The differentially expressed EST sequences are then searched against available databases, including the "nt", "nr", "est", "gss" and "htg" databases available through NCBI to determine putative identities for ESTs matching to known genes or other ESTs. Functional characterisation of ESTs with known gene matches are made according to any known method. Preferably, differentially expressed EST sequences are compared to the non-redundant Genbank/EMBL/DDBJ and dbEST databases using the BLAST algorithm (Altschul S F, Gish W, Miller W, Myers E W, Lipman D J., Basic local alignment search tool., J. Mol. Biol., 1990; 215:403-10). A minimum value of $P=10^{-10}$ and nucleotide sequence identity >95%, where the sequence identity is non-contiguous or scattered, are required for assignments of putative identities for ESTs matching to known genes or to other ESTs. Construction of a non-redundant list of genes represented in the EST set is done with the help of Unigene, Entrez and PubMed at the National Center for Biotechnology Information (NCBI) web site at www.ncbi.nlm.nih.gov.

Genes are identified from ESTs according to known methods. To identify novel genes from an EST sequence, the EST should preferably be at least 100 nucleotides in length, and more preferably 150 nucleotides in length, for annotation. Preferably, the EST exhibits open reading frame characteristics (i.e., can encode a putative polypeptide).

Because of the completion of the Human Genome Project, a specific EST which matches with a genomic sequence can be mapped onto a specific chromosome based on the chromosomal location of the genomic sequence. However, no function may be known for the protein encoded by the sequence and the EST would then be considered "novel" in a functional sense. In one aspect, the invention is used to identify a novel differentially expressed EST, which is part of a larger known sequence for which no function is known, is used to determine the function of a gene comprising the EST. Alternatively, or additionally, the EST can be used to identify an mRNA or polypeptide encoded by the larger sequence as a diagnostic or prognostic marker of a disease.

Having identified an EST corresponding to a larger sequence, other portions of the larger sequence which comprises the EST can be used in assays to elucidate gene function, e.g., to isolate polypeptides encoded by the gene, to generate antibodies specifically reactive with these polypeptides, to identify binding partners of the polypeptides (receptors, ligands, agonists, antagonists and the like) and/or to detect the expression of the gene (or lack thereof) in healthy or diseased individuals.

In another aspect, the invention provides for nucleic acid sequences that do not demonstrate a "significant match" to any of the publicly known sequences in sequence databases at the time a query is done. Longer genomic segments comprising these types of novel EST sequences can be identified by probing genomic libraries, while longer expressed sequences can be identified in cDNA libraries and/or by performing polymerase extension reactions (e.g., RACE) using EST sequences to derive primer sequences as is known in the art. Longer fragments can be mapped to particular chromosomes by FISH and other techniques and their sequences compared to known sequences in genomic and/or expressed sequence databases.

The amino acid sequences encoded by the ESTs can also be used to search databases, such as GenBank, SWISS-PROT, EMBL database, PIR protein database, Vecbase, or GenPept for the amino acid sequences of the corresponding full-length genes according to procedures well known in the art.

Identified genes can be catalogued according to their putative function. Functional characterization of ESTs with known gene matches is preferably made according to the categories described by Hwang et al Compendium of Cardiovascular Genes. Circulation 1997; 96:4146-203. The distribution of genes in each of the subcellular categories will provide important insights into the disease process.

Alternative methods for analysing ESTs are also available. For example, the ESTs may be assembled into contigs with sequence alignment, editing, and assembly programs such as PHRED and PHRAP (Ewing, et al., 1998, Genome Res., 3:175, incorporated herein; and the web site at bozeman.genome.washington.edu). Contig redundancy is reduced by clustering nonoverlapping sequence contigs using the EST clone identification number, which is common for the non-overlapping 5 and 3 sequence reads for a single EST cDNA clone. In one aspect, the consensus sequence from each cluster is compared to the non-redundant Genbank/EMBL/DDBJ and dbEST databases using the BLAST algorithm with the help of unigene, Entrez and PubMed at the NCBI site.

Known Nucleic Acid Sequences or ESTs and Novel Nucleic Acid Sequences or ESTs

An EST that exhibits a significant match (>65%, and preferably 90% or greater, identity) to at least one existing sequence in an existing nucleic acid sequence database is characterised as a "known" sequence according to the invention. Within this category, some known ESTs match to existing sequences which encode polypeptides with known function(s) and are referred to as a "known sequence with a function". Other "known" ESTs exhibit a significant match to existing sequences which encode polypeptides of unknown function(s) and are referred to as a "known sequence with no known function".

EST sequences which have no significant match (less than 65% identity) to any existing sequence in the above cited available databases are categorized as novel ESTs. To identify a novel gene from an EST sequence, the EST is preferably at least 150 nucleotides in length. More preferably, the EST encodes at least part of an open reading frame, that is, a nucleic acid sequence between a translation initiation codon and a termination codon, which is potentially translated into a polypeptide sequence.

The following references were cited herein:
Claudio J O et al. (1998). Genomics 50:44-52.
Chelly J et al. (1989). Proc. Nat. Acad. Sci. USA. 86:2617-2621.
Chelly J et al. (1988). Nature 333:858-860.
Drews J & Ryser S (1997). Nature Biotech. 15:1318-9.
Ferrie R M et al. (1992). Am. J. Hum. Genet. 51:251-62.
Fu D-J et al. (1998). Nat. Biotech 16: 381-4.
Gala J L et al. (1998). Clin. Chem. 44(3):472-81.
Geisterfer-Lowrance A A T et al. (1990). Cell 62:999-1006.
Groden J et al. (1991). Cell 66:589-600.
Hwang D M et al. (1997). Circulation 96:4146-4203.
Jandreski M A & Liew C C (1987). Hum. Genet. 76:47-53.
Jin O et al. (1990). Circulation 82:8-16
Kimoto Y (1998). Mol. Gen. Genet 258:233-239.
Koster M et al. (1996). Nat. Biotech 14: 1123-8.
Liew & Jandreski (1986). Proc. Nat. Acad. Sci. USA. 83:3175-3179
Liew C C et al. (1990). Nucleic Acids Res. 18:3647-3651.
Liew C C (1993). J. Mol. Cell. Cardiol. 25:891-894
Liew C C et al. (1994). Proc. Natl. Acad. Sci. USA. 91:10645-10649.
Liew et al. (1997). Mol. and Cell. Biochem. 172:81-87.
Niimura H et al. (1998). New Eng. J. Med. 338:1248-1257.
Ogawa M (1993). Blood 81:2844-2853.
Santoro I M & Groden J (1997). Cancer Res. 57:488-494.
Yuasa T et al. (1998). Japanese J. Cancer Res. 89:879-882.

Description of Tables:
Table 1: Overlap of Genes Expressed in Blood
(Estimated from about 5,100 unique known genes from the over 25,000 ESTs obtained from human blood cDNA libraries).
Table 2: Comparison of approximately 5,140 Unique Genes Identified in the Blood Cell cDNA Library to Genes Previously Identified in Specific Tissues
Column 1: List of unique genes derived from 25,000 known ESTs from blood cells.
Column 2: Number of genes found in randomly sequenced ESTs from blood cells.
Column 3: Accession number.
Column 4: "+" indicates the presence of the unique gene in publicly available cDNA libraries of blood (Bl), brain (Br), heart (H), kidney (K), liver (Li) and lung (Lu).

Figure 8:
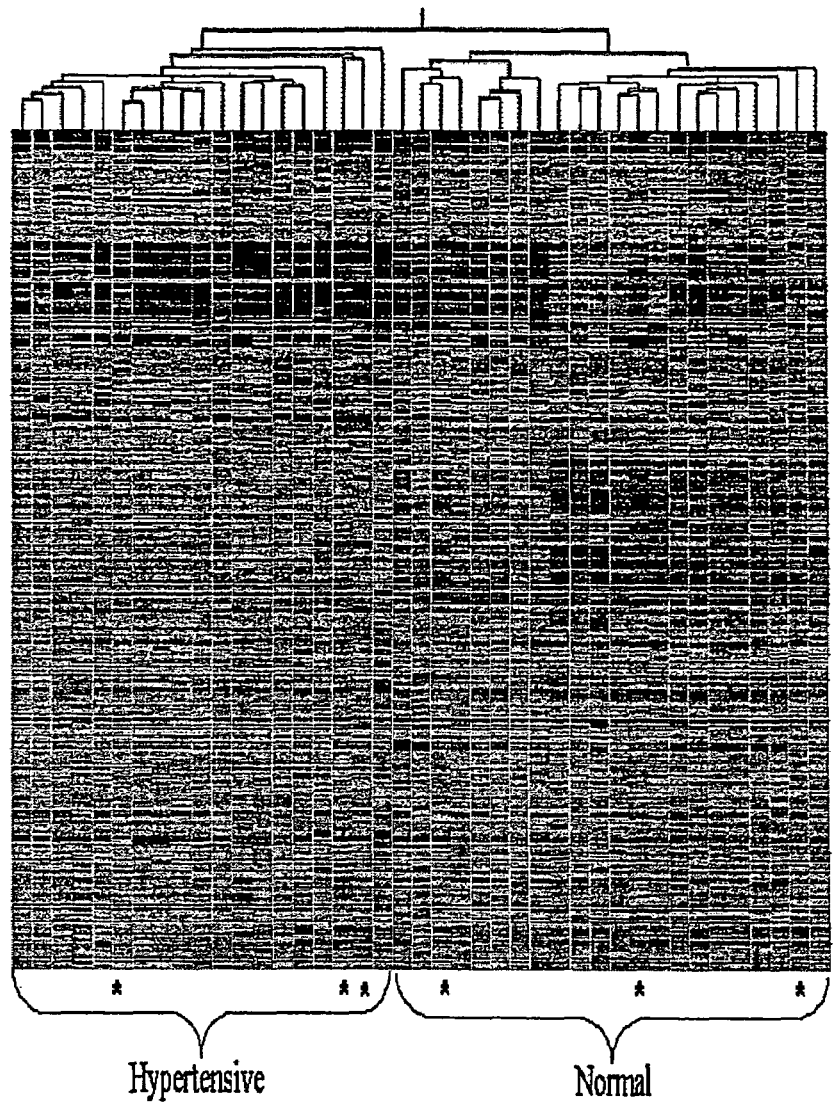
FIG. 8 shows a diagrammatic representation of gene expression profiles of blood samples from individuals having both osteoarthritis and hypertension as compared with gene expression profiles from normal individuals.
Figure 9:
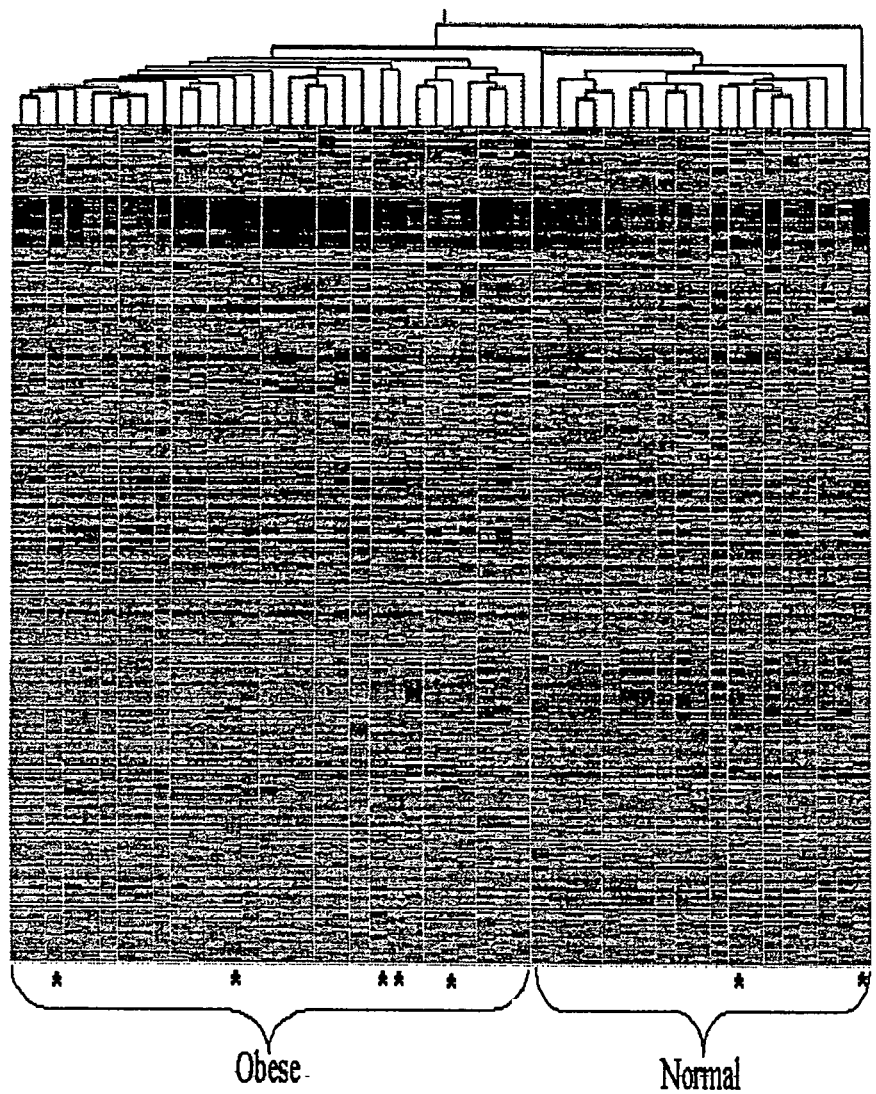
FIG. 9 shows a diagrammatic representation of gene expression profiles of blood samples from individuals who were identified as having both osteoarthritis and who were obese as described herein as compared with gene expression profiles from normal individuals.
Figure 10:
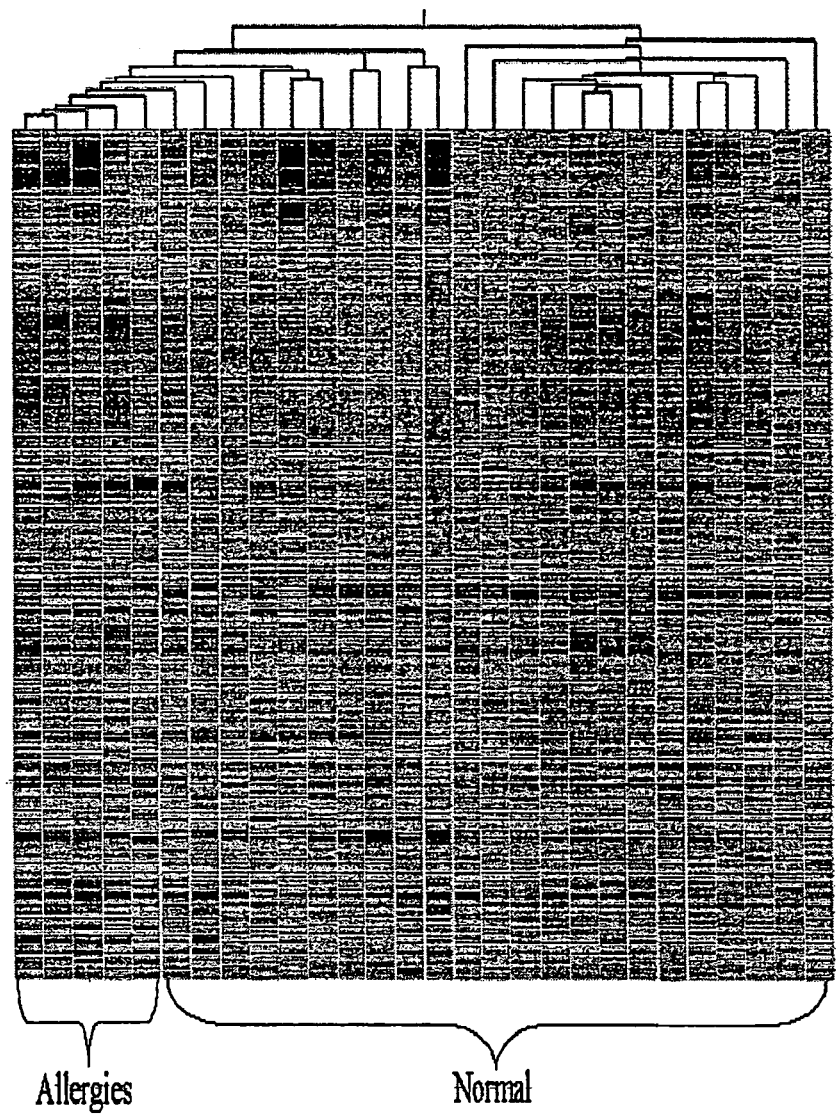
FIG. 10 shows a diagrammatic representation of gene expression profiles of blood samples from individuals who were identified as having both osteoarthritis and allergies as described herein as compared with gene expression profiles from normal individuals.
Figure 11:
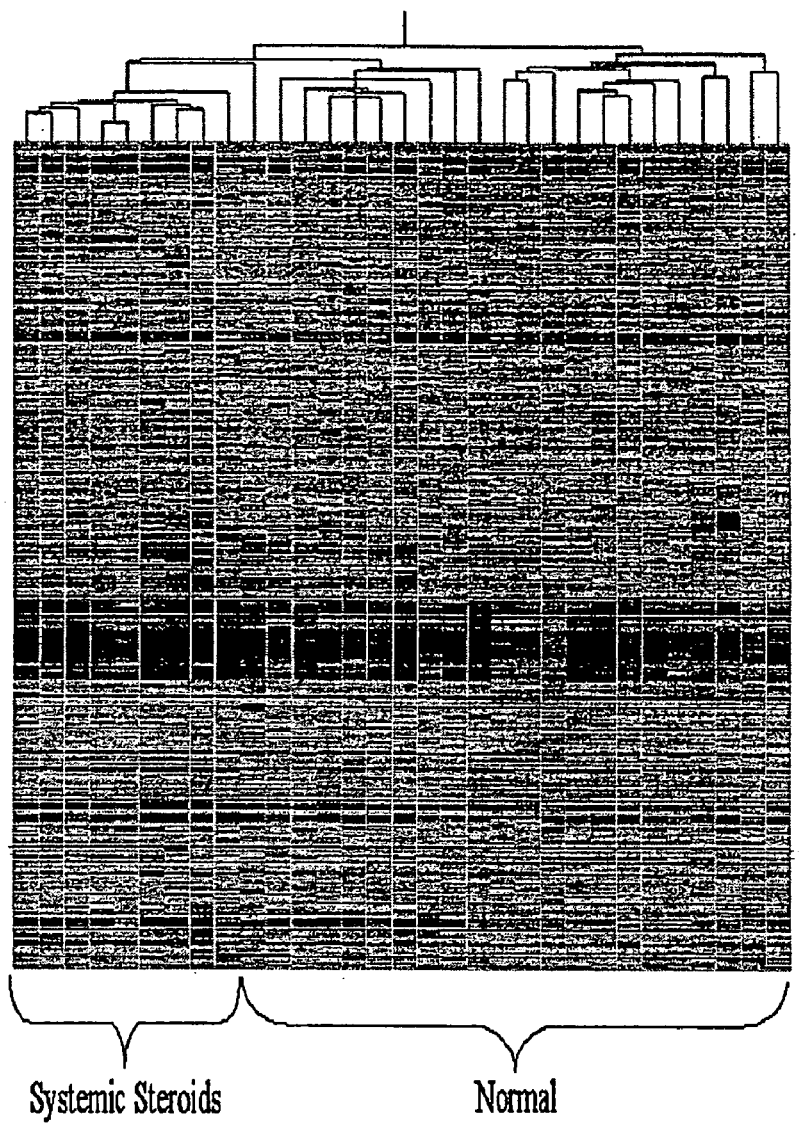
FIG. 11 shows a diagrammatic representation of gene expression profiles of blood samples from individuals having osteoarthritis and who were subject to systemic steroids as described herein as compared with gene expression profiles from normal individuals.
Figure 12:
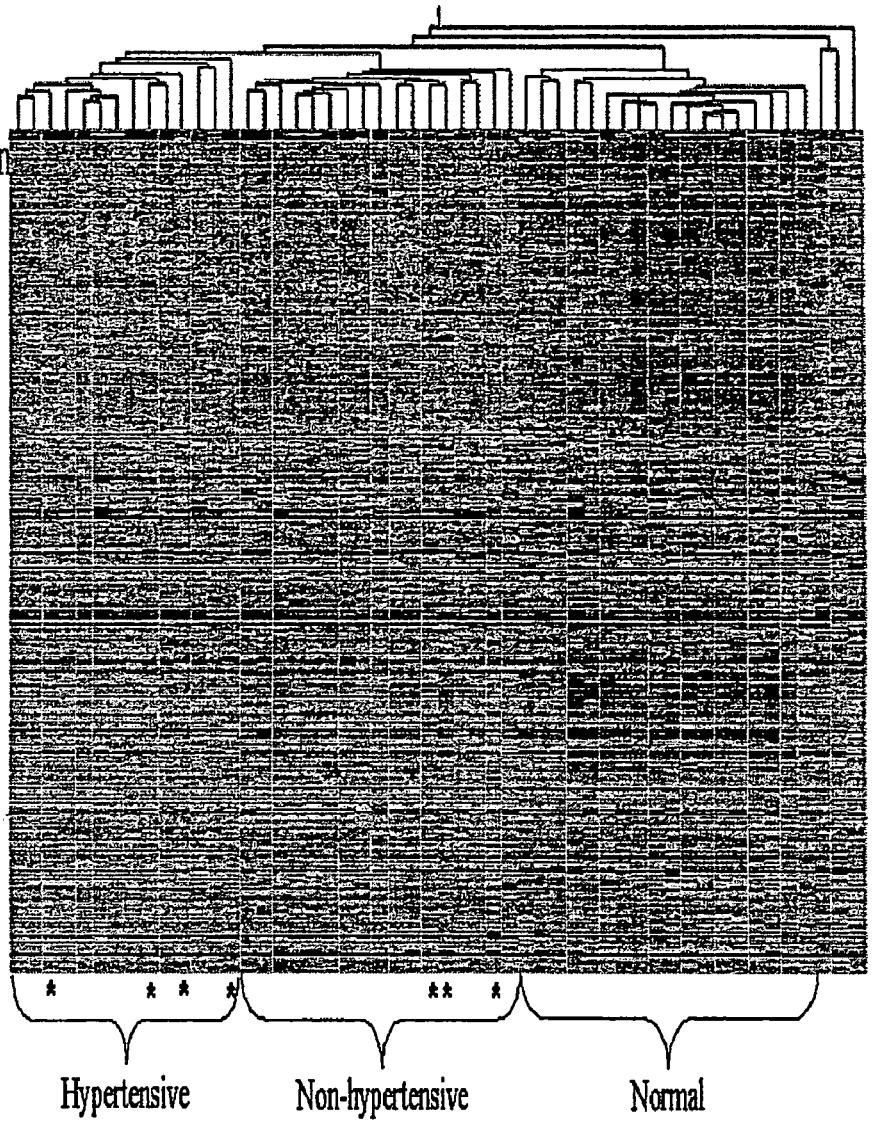
FIG. 12 shows a diagrammatic representation of gene expression profiles of blood samples from individuals having hypertension as compared with gene expression profiles from samples of both non-hypertensive and normal individuals.
Figure 13:
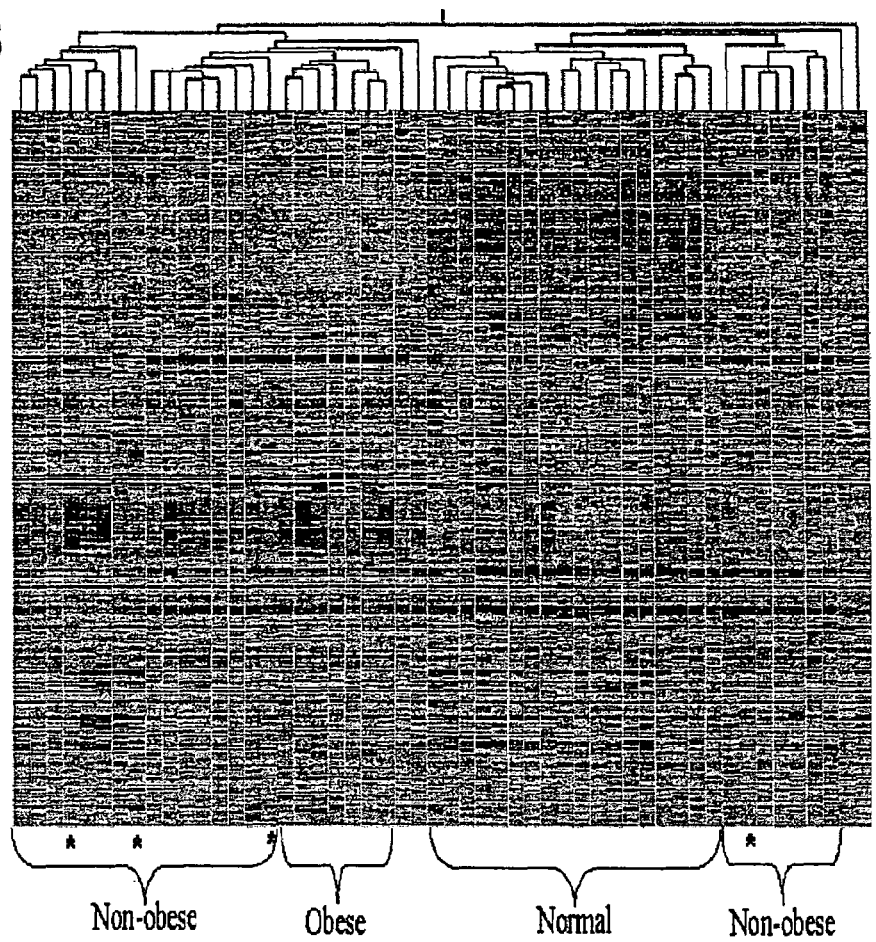
FIG. 13 shows a diagrammatic representation of gene expression profiles of blood samples from individuals who were identified as obese as described herein as compared with gene expression profiles from normal and non-obese individuals.
Figure 14:
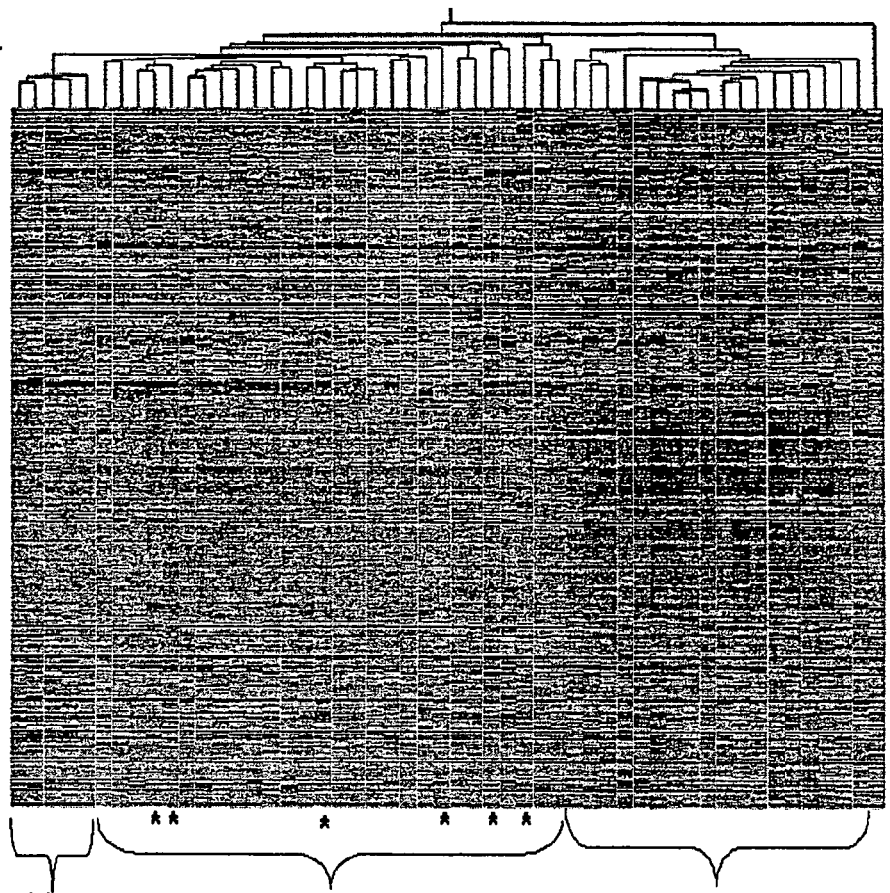
FIG. 14 shows a diagrammatic representation of gene expression profiles of blood samples from individuals who were identified as having type 2 diabetes as described herein as compared with gene expression profiles from normal and non-type 2 diabetes individuals.
Figure 15:
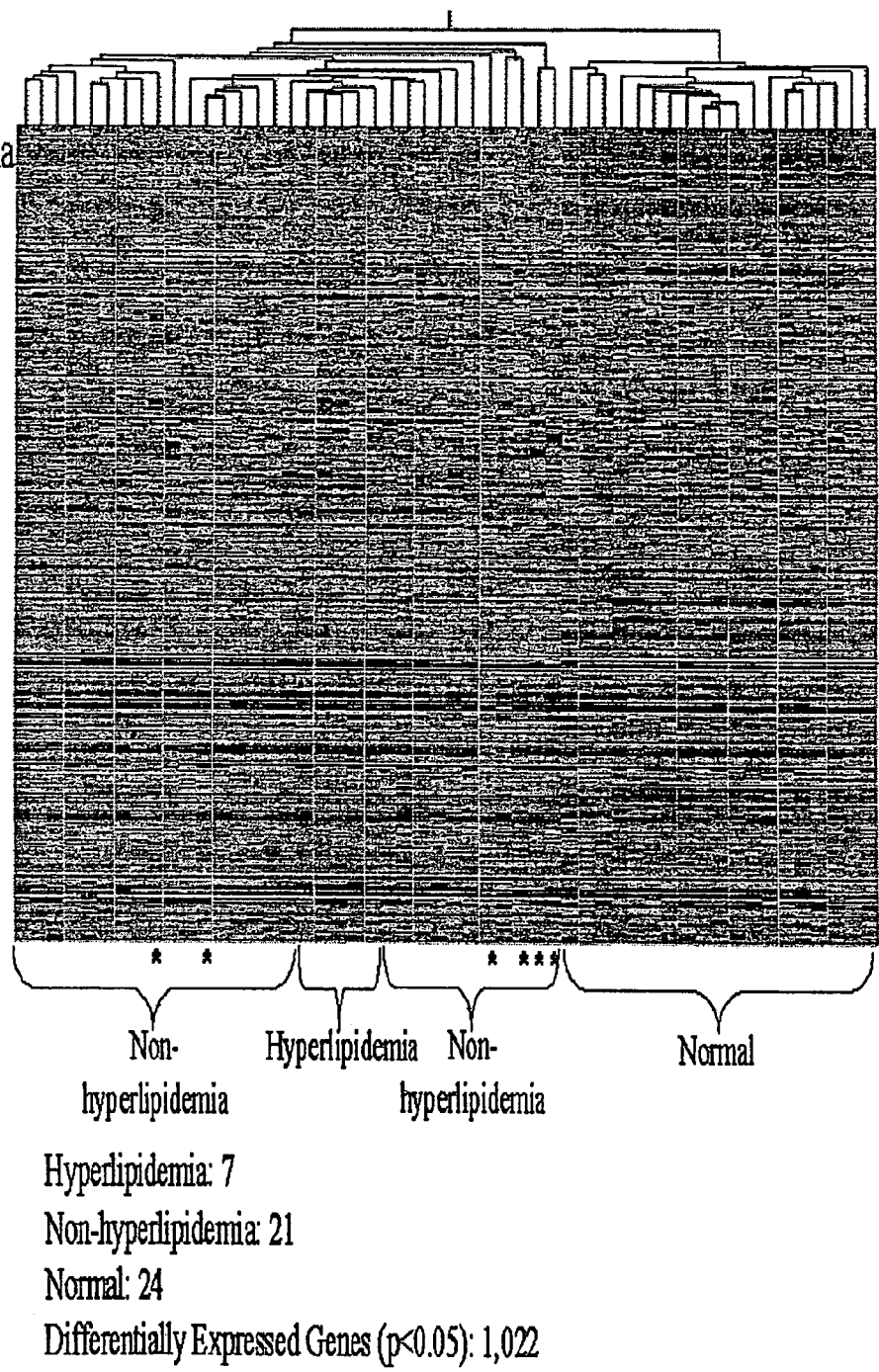
FIG. 15 shows a diagrammatic representation of gene expression profiles of blood samples from individuals who were identified as having hyperlipidemia as described herein as compared with gene expression profiles from normal and non-hyperlipidemia patients.
Figure 16:
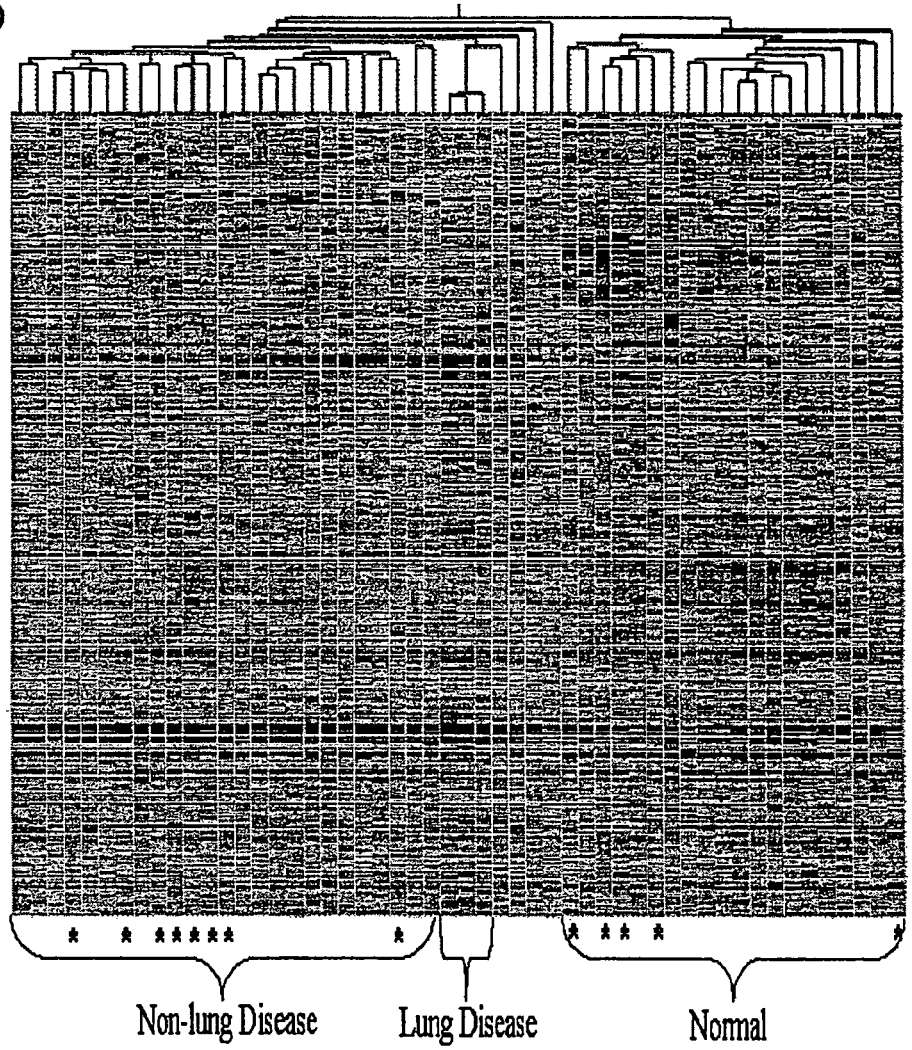
FIG. 16 shows a diagrammatic representation of gene expression profiles of blood samples from individuals who were identified as having lung disease as described herein as compared with gene expression profiles from normal and non lung disease individuals.

**Comparison to previously identified tissue-specific genes was determined using the GenBank of the National Centre of Biotechnology Information (NCBI) Database.
Table 3 shows genes that are differentially expressed in blood samples from patients with different diseases as compared to blood samples from healthy patients.
Table 3A shows the identity of those genes that are differentially expressed in blood samples from patients with osteoarthritis and hypertension as compared with normal patients as depicted in FIG. 8
Table 3B shows the identity of those genes that are differentially expressed in blood samples from patients with osteoarthritis and obesity as compared with normal patients as depicted in FIG. 9.
Table 3C shows the identity of those genes that are differentially expressed in blood samples from patients with osteoarthritis and allergies as compared with normal patients as depicted in FIG. 10.
Table 3D shows the identity of those genes that are differentially expressed in blood samples from patients with osteoarthritis and subject to systemic steroids as compared with normal patients as depicted in FIG. 11.
Table 3E shows the identity of those genes that are differentially expressed in blood samples from patients with hypertension as depicted in FIG. 12.
Table 3F shows the identity of those genes that are differentially expressed in blood samples from patients obesity as depicted in FIG. 13.
Table 3G shows the identity of those genes that are differentially expressed in blood samples from patients with type II diabetes as depicted in FIG. 14.
Table 3H shows the identity of those genes that are differentially expressed in blood samples from patients with hyperlipidemia as depicted in FIG. 15.
Table 3I shows the identity of those genes that are differentially expressed in blood samples from patients with lung disease as depicted in FIG. 16.

Figure 17:
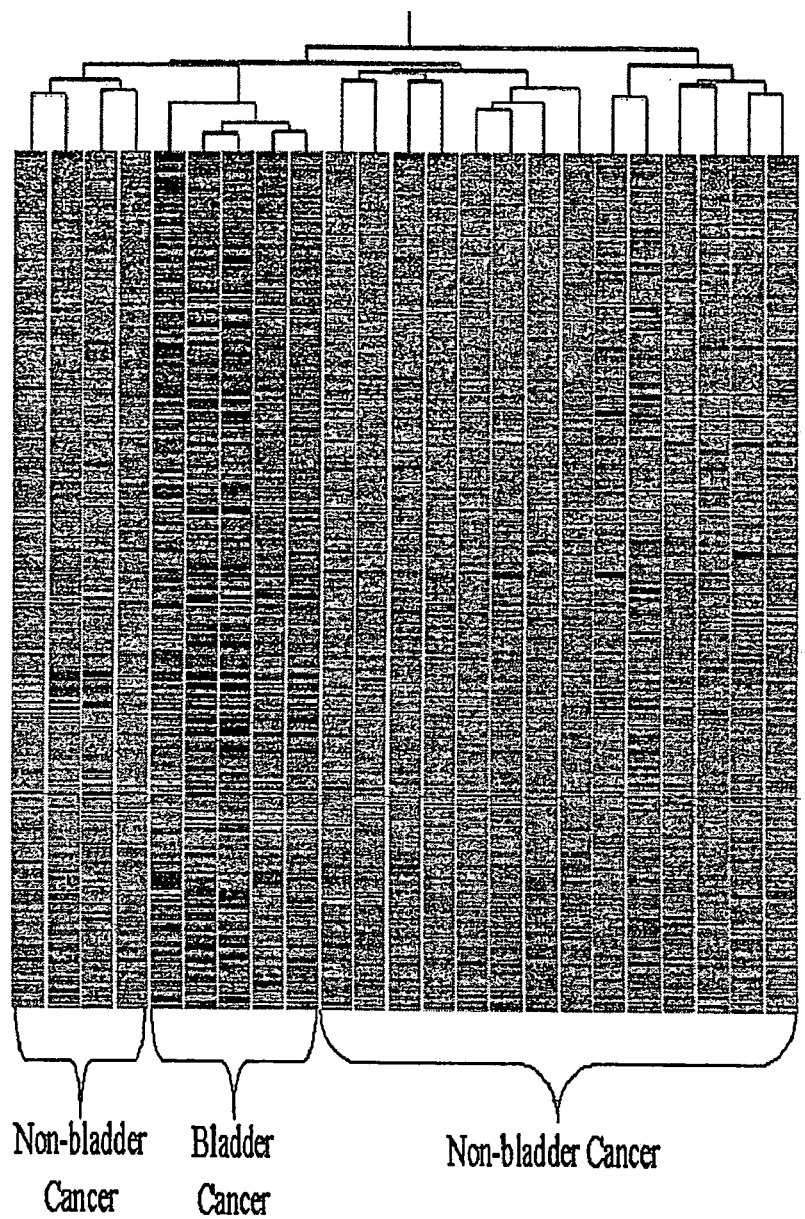
FIG. 17 shows a diagrammatic representation of gene expression profiles of blood samples from individuals who were identified as having bladder cancer as described herein as compared with gene expression profiles from non bladder cancer individuals.

Table 3J shows the identity of those genes that are differentially expressed in blood samples from patients with bladder cancer as depicted in FIG. 17.

Figure 18:
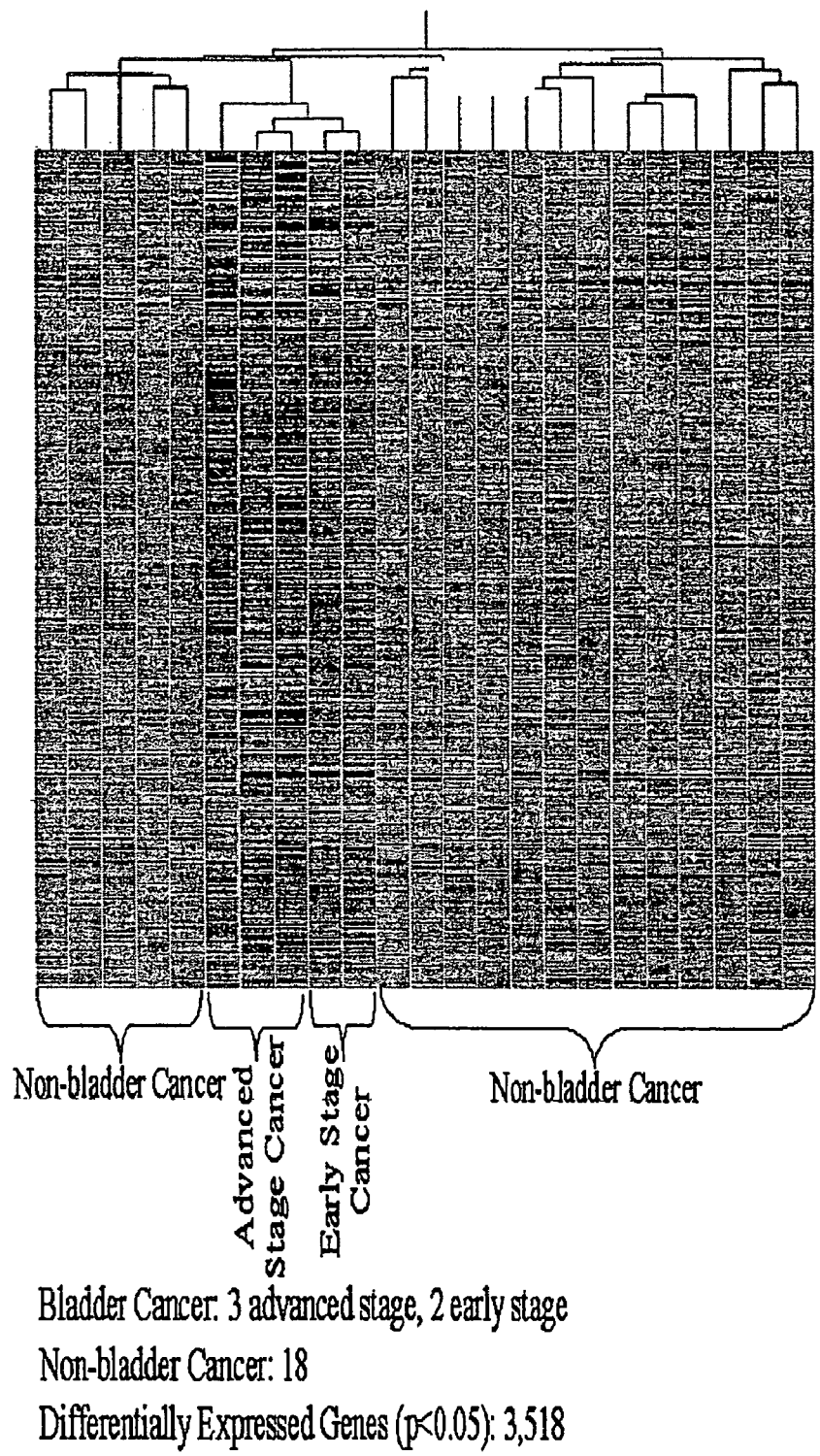
FIG. 18 shows a diagrammatic representation of gene expression profiles of blood samples from individuals who were identified as having advanced stage bladder cancer or early stage bladder cancer as described herein as compared with gene expression profiles from non bladder cancer individuals.

Table 3K shows the identity of those genes that are differentially expressed in blood samples from patients with bladder cancer as depicted in FIG. 18.

Figure 19:
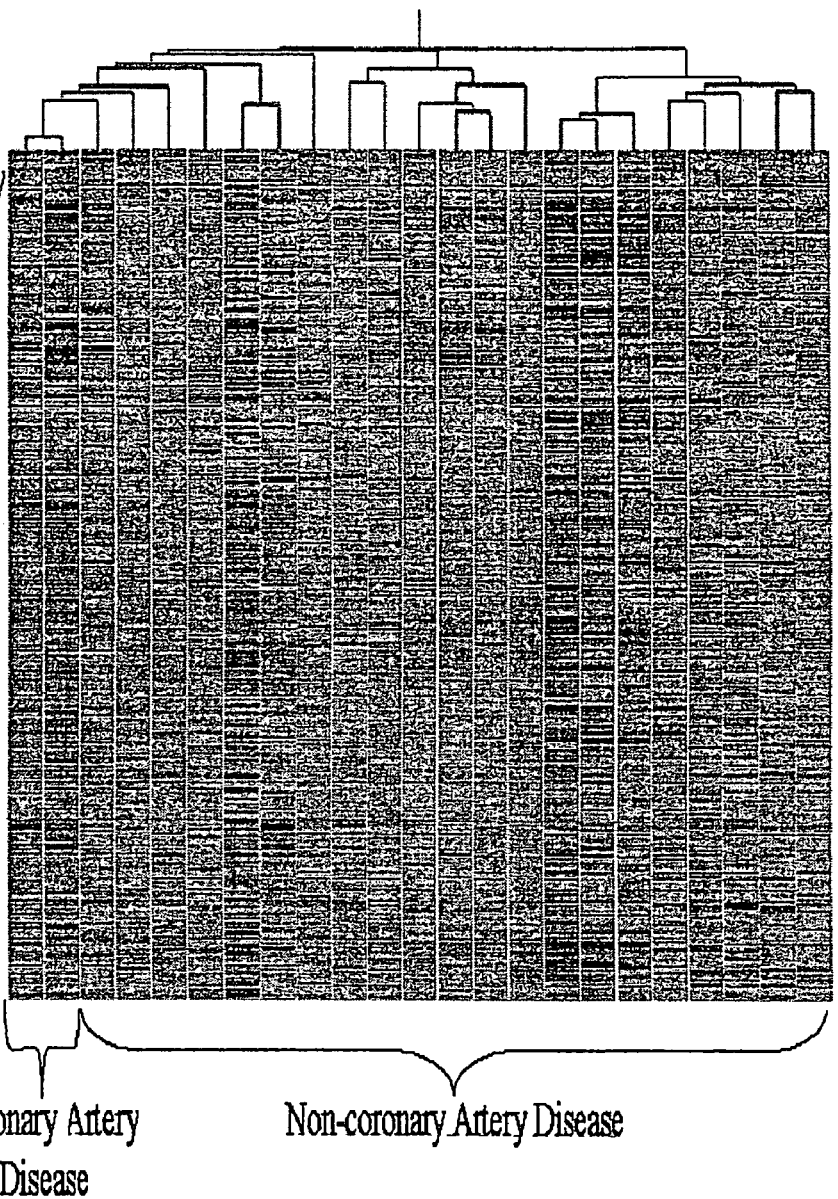
FIG. 19 shows a diagrammatic representation of gene expression profiles of blood samples from individuals who were identified as having coronary artery disease (CAD) as described herein as compared with gene expression profiles from non-coronary artery disease individuals.

Table 3L shows the identity of those genes that are differentially expressed in blood samples from patients with coronary artery disease (CAD) as depicted in FIG. 19.

Figure 20:
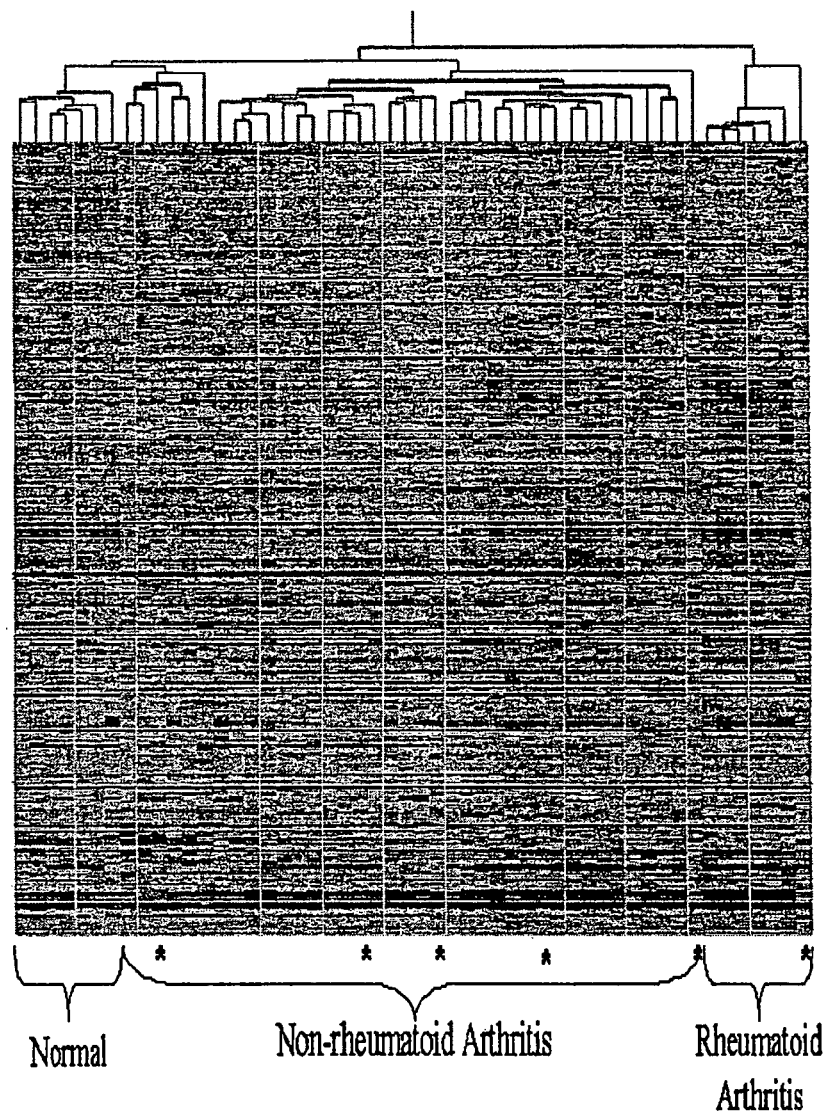
FIG. 20 shows a diagrammatic representation of gene expression profiles of blood samples from individuals who were identified as having rheumatoid arthritis as described herein as compared with gene expression profiles from non-rheumatoid arthritis individuals.

Table 3M shows the identity of those genes that are differentially expressed in blood samples from patients with rheumatoid arthritis as depicted in FIG. 20.

Figure 21:
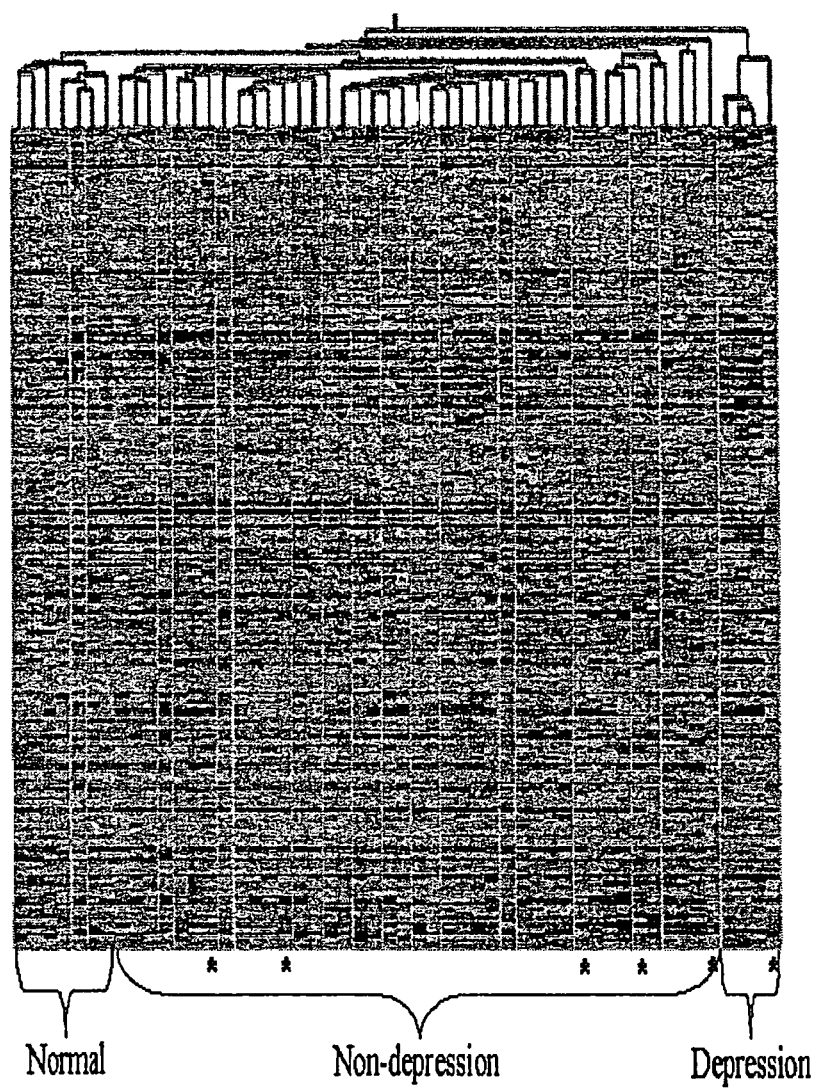
FIG. 21 shows a diagrammatic representation of gene expression profiles of blood samples from individuals who were identified as having depression as described herein as compared with gene expression profiles from non-depression individuals.

Table 3N shows the identity of those genes that are differentially expressed in blood samples from patients with depression as depicted in FIG. 21.

Figure 22:
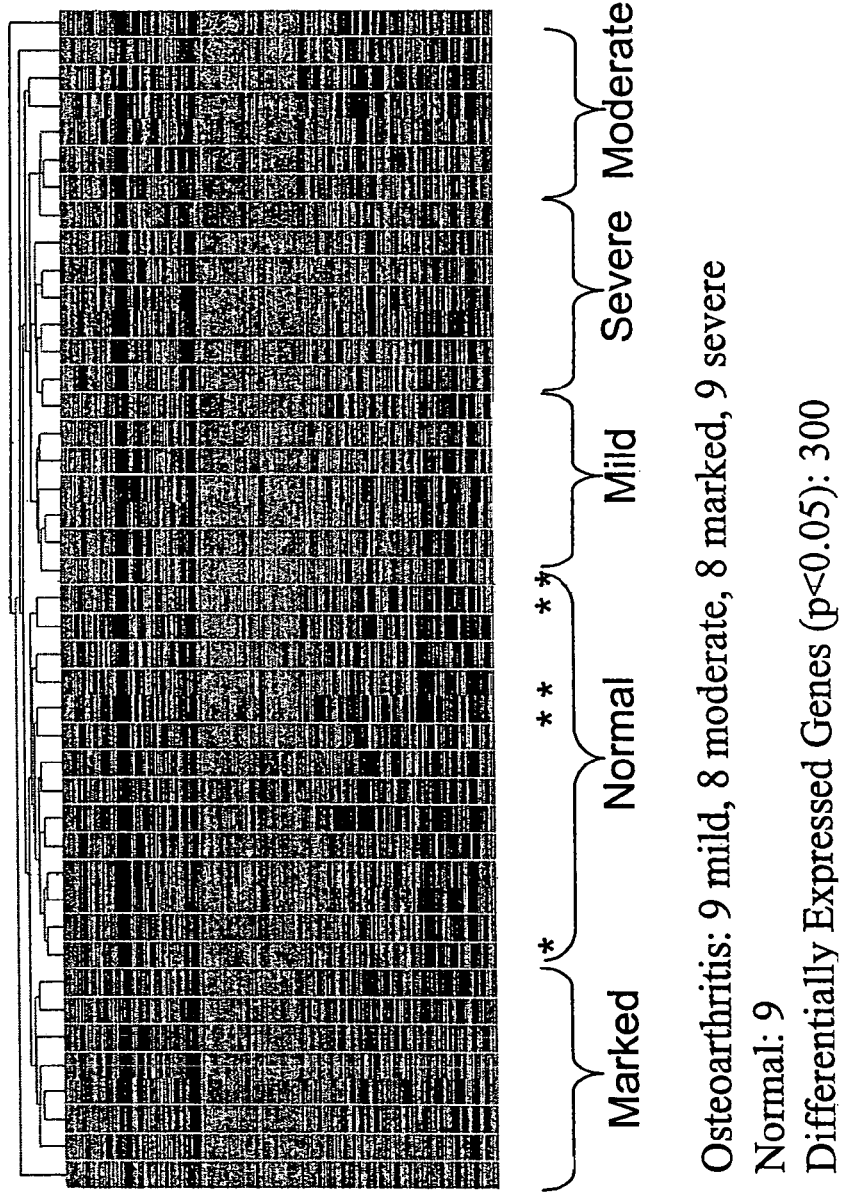
FIG. 22 shows a diagrammatic representation of gene expression profiles of blood samples from individuals who were identified as having various stages of osteoarthritis as described herein as compared with gene expression profiles from normal individuals.
Figure 23:
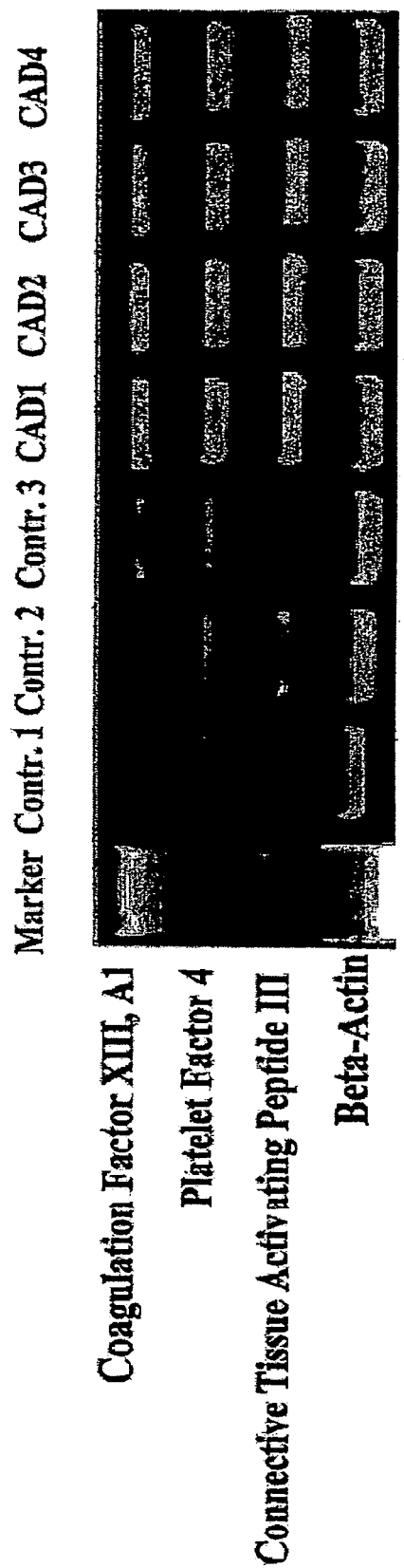
FIG. 23 shows RT-PCR of overexpressed genes in CAD peripheral blood cells identified using microarray experiments, including PBP, PF4 and F13A.

Table 3O shows the identity of those genes that are differentially expressed in blood samples from patients with various stages of osteoarthritis as depicted in FIG. 22.

Table 3P shows the identity of those genes that are differentially expressed in blood samples from patients with hypertension and OA when compared with patients who have OA only wherein genes identified in Table 3A have been removed so as to identify genes which are unique to hypertension.

Table 3Q shows the identity of those genes which were identified in Table 3A which are shared with those genes differentially expressed in blood samples from patients with hypertension and OA when compared with patients who have OA only.

Table 3R shows the identity of those genes that are differentially expressed in blood samples from patients who are obese and have OA when compared with patients who have OA only and wherein genes identified in Table 3B have been removed so as to identify genes which are unique to obesity.

Table 3S shows the identify of those genes identified in Table 3B which are shared with those genes differentially expressed in blood samples from patients who are obese and have OA when compared with patients who have OA.

Table 3T shows the identity of those genes that are differentially expressed in blood samples from patients with allergies and OA when compared with patients who have OA only wherein genes identified in Table 3C have been removed so as to identify genes which are unique to allergies.

Table 3U shows the identify of those genes identified in Table 3C which are shared with those genes differentially expressed in blood samples from patients with allergies and OA when compared with patients who have OA only.

Table 3V shows the identity of those genes that are differentially expressed in blood samples from patients who are on systemic steroids and have OA when compared with patients who have OA only wherein genes identified in Table 3D have been removed so as to identify genes which are unique to patients on systemic steroids.

Table 3W shows the identify of those genes identified in Table 3D which are shared with those genes differentially expressed in blood samples from patients who are on systemic steroids and have OA when compared with patients who have OA only.

Figure 25:
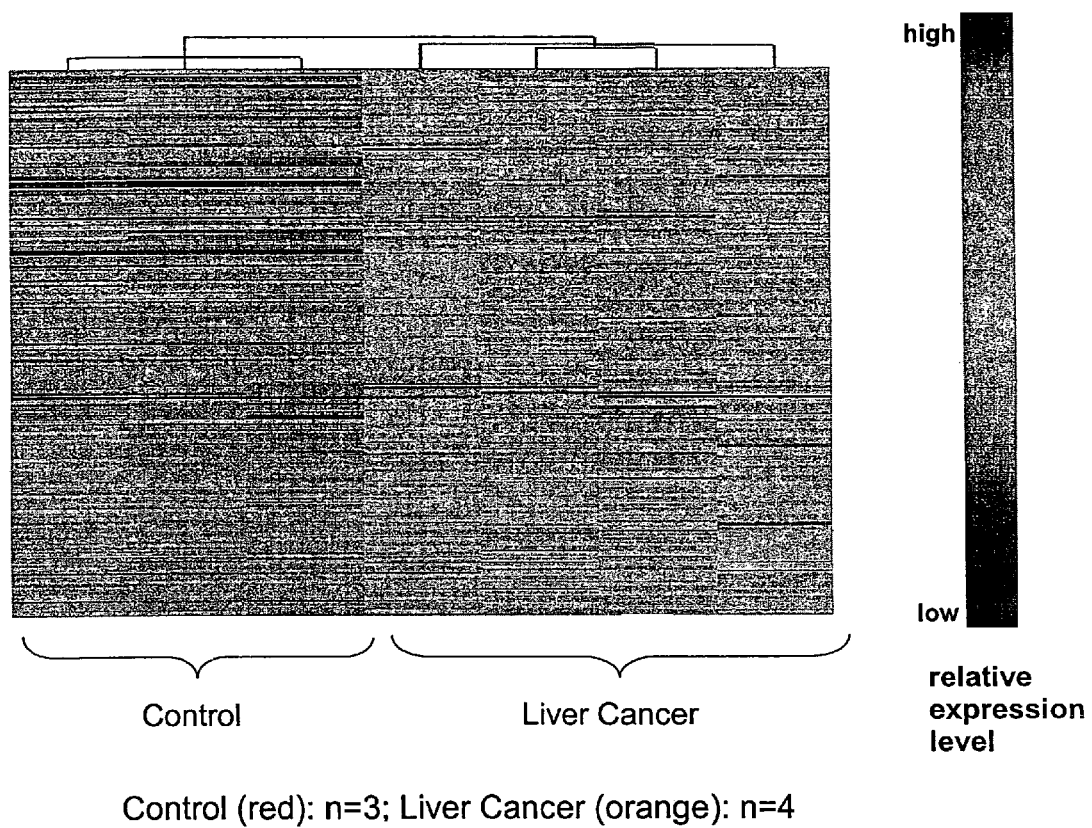
FIG. 25 shows a diagrammatic representation of gene expression profiles of blood samples from individuals who were identified as having liver cancer as described herein as compared with gene expression profiles from normal individuals.

Table 3X shows the identity of those genes that are differentially expressed in blood samples from patients with liver cancer as depicted in FIG. 25.

Figure 26:
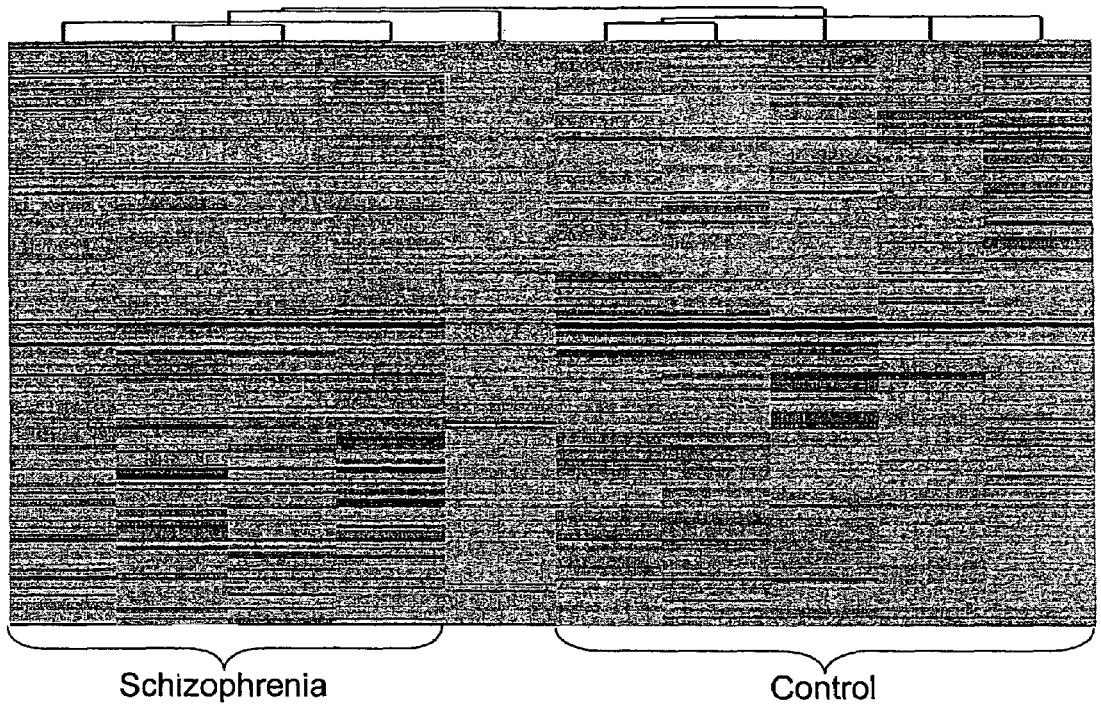
FIG. 26 shows a diagrammatic representation of gene expression profiles of blood samples from individuals who were identified as having schizophrenia as described herein as compared with gene expression profiles from normal individuals.

Table 3Y shows the identity of those genes that are differentially expressed in blood samples from patients with schizophrenia as depicted in FIG. 26.

Figure 27:
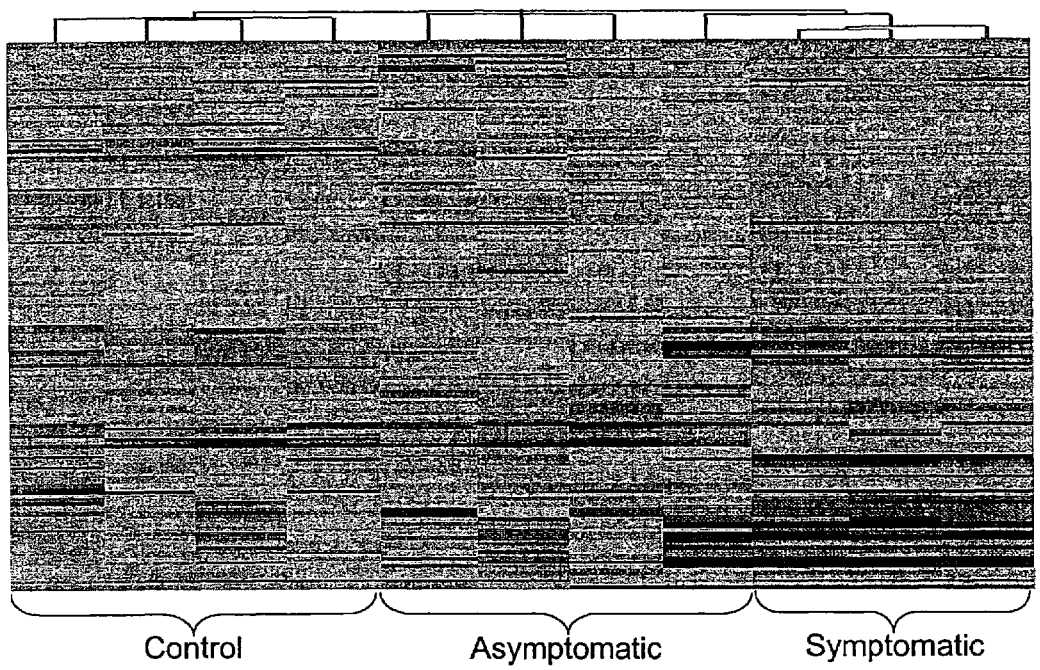
FIG. 27 shows a diagrammatic representation of gene expression profiles of blood samples from individuals who were identified as having symptomatic or asymptomatic chagas disease as described herein as compared with gene expression profiles from normal individuals.

Table 3Z shows the identity of those genes that are differentially expressed in blood samples from patients with Chagas disease as depicted in FIG. 27.

Figure 28:
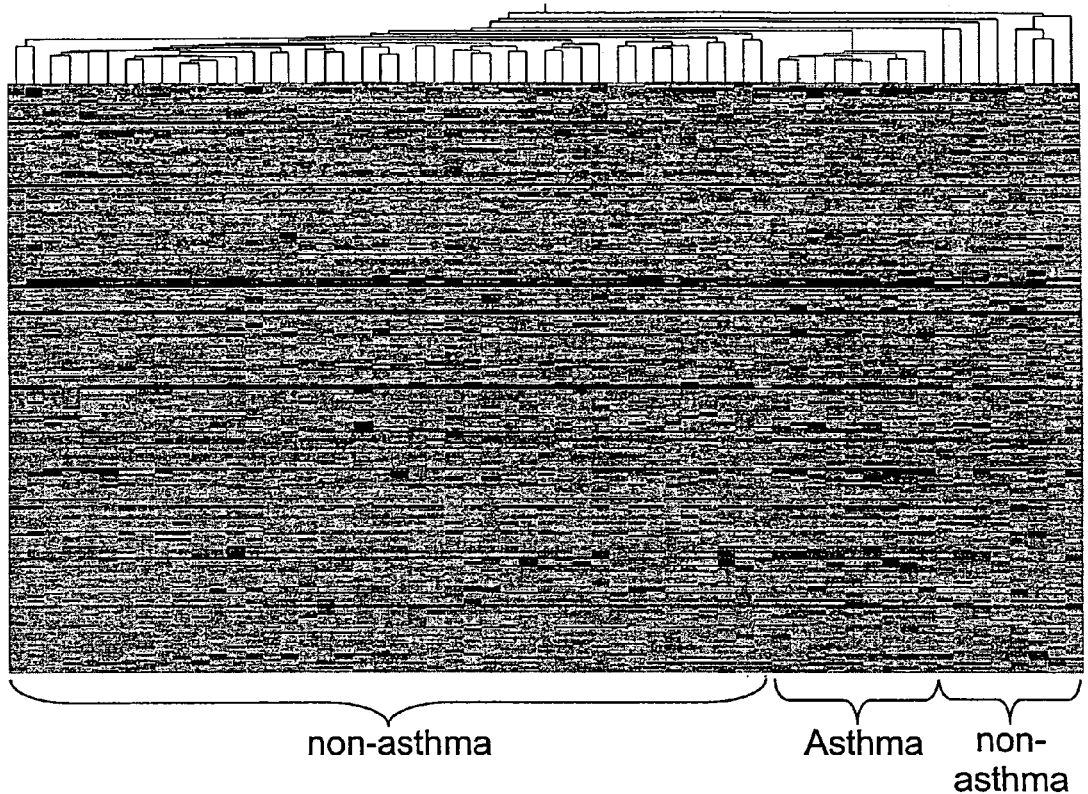
FIG. 28 shows a diagrammatic representation of gene expression profiles of blood samples from individuals who were identified as having asthma and OA as compared with individuals having just OA.
Figure 29:
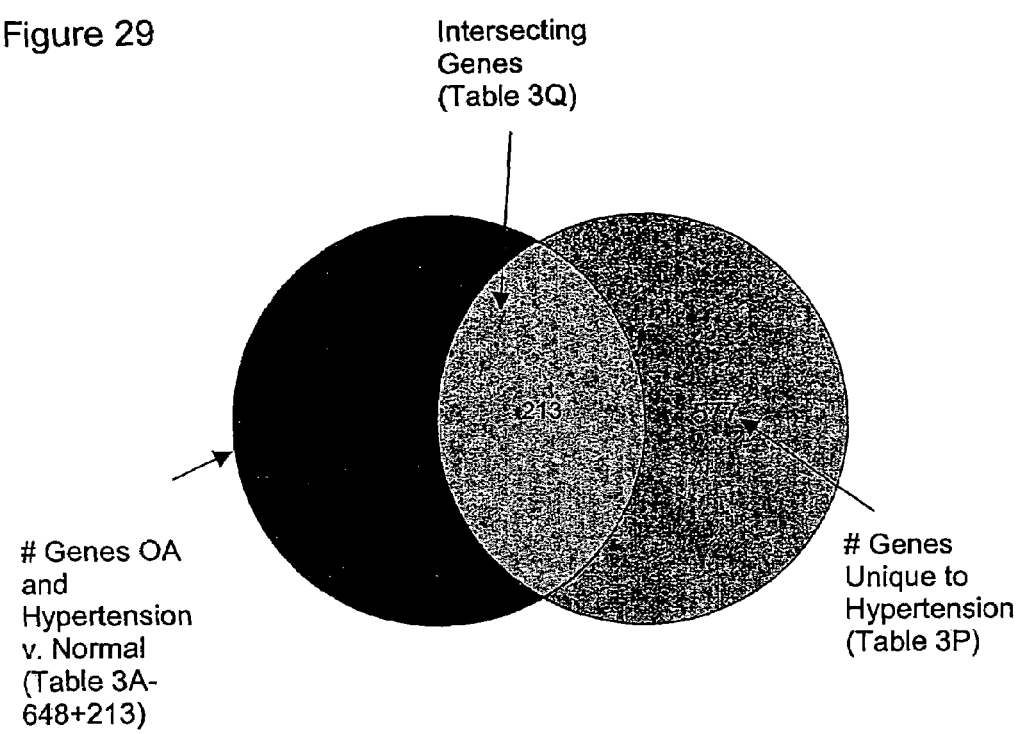
FIG. 29 shows a venn diagram illustrating a summary of the analysis comparing hypertension and OA patients vs. normal (Table 3A) hypertension and OA patients vs. OA patients (Table 3P) and the intersection between the two populations of genes (Table 3Q).
Figure 30:
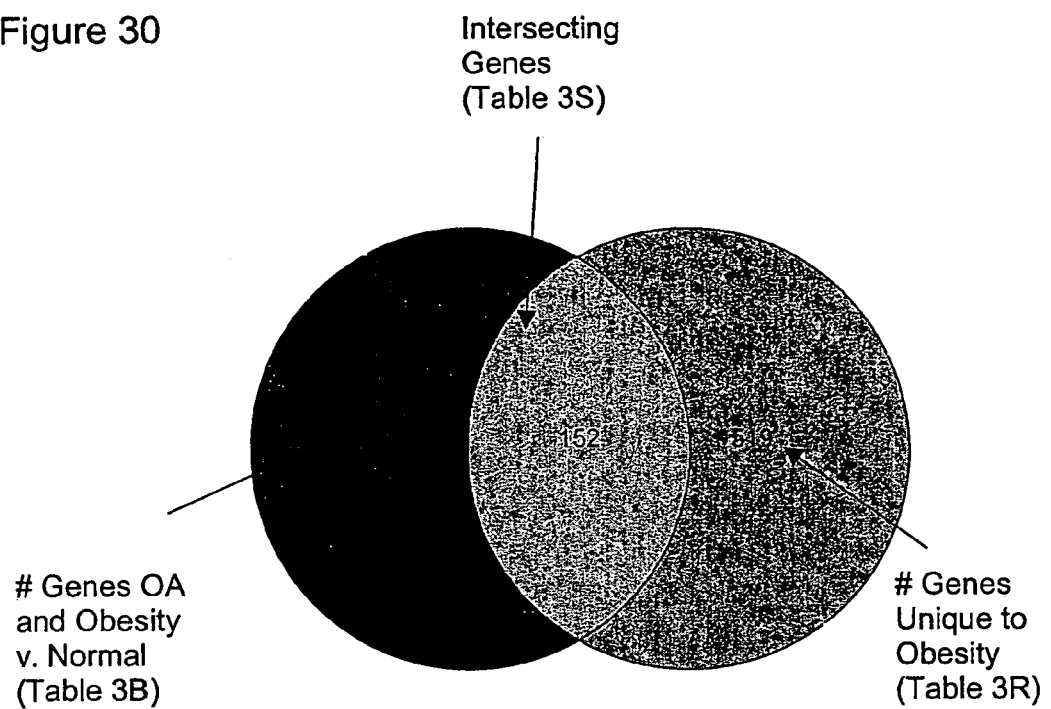
FIG. 30 shows a venn diagram illustrating a summary of the analysis comparing obesity and OA patients vs. normal (Table 3B) obesity and OA patients vs. OA patients (Table 3R) and the intersection between the two populations of genes (Table 3S).
Figure 31:
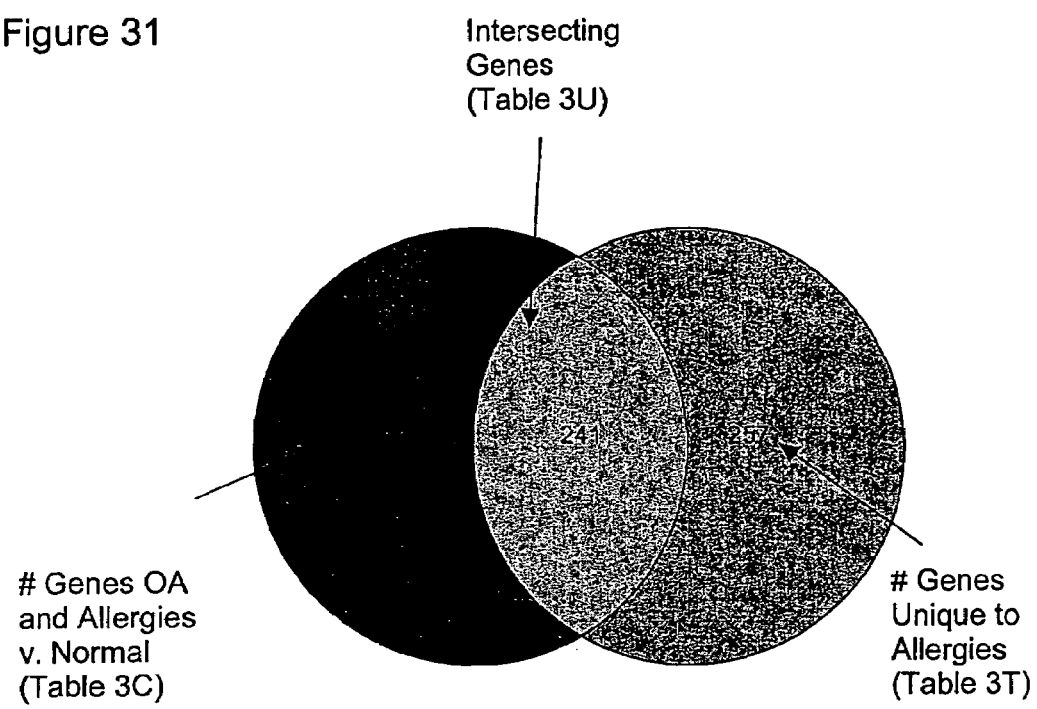
FIG. 31 shows a venn diagram illustrating a summary of the analysis comparing allergy and OA patients vs. normal (Table 3C) allergy and OA patients vs. OA patients (Table 3T) and the intersection between the two populations of genes (Table 3U).
Figure 32:
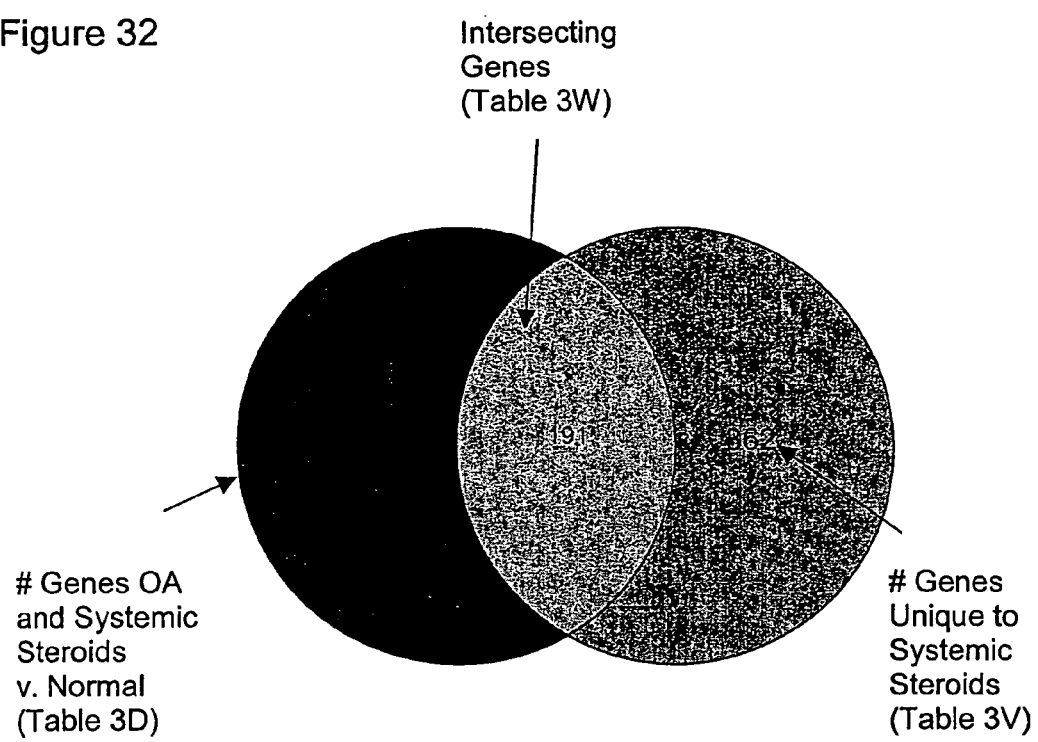
FIG. 32 shows a venn diagram illustrating a summary of the analysis comparing systemic steroids and OA patients vs. normal (Table 3D) systemic steroids and OA patients vs. OA patients (Table 3V) and the intersection between the two populations of genes (Table 3W).
Figure 33:
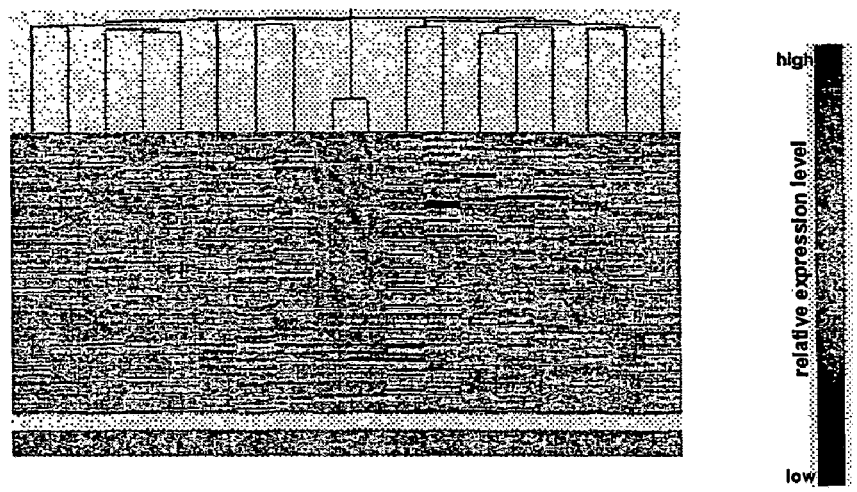
FIG. 33 shows a diagrammatic representation of gene expression profiles of blood samples from individuals who were identified as having Manic Depression as compared with those individuals who have Schizophrenia.

Table 3AA shows the identity of those genes that are differentially expressed in blood samples from patients with asthma as depicted in FIG. 28.

Table 3AB shows the identity of those genes that are differentially expressed in blood from patients with either mild or severe OA, but for which genes relevant to asthma, obesity, hypertension, systemic steroids and allergies have been removed.

Table 3AC shows the identity of those genes that are differentially expressed in blood from patients with schizophrenia as compared with manic depression syndrome (MDS).

Figure 34:
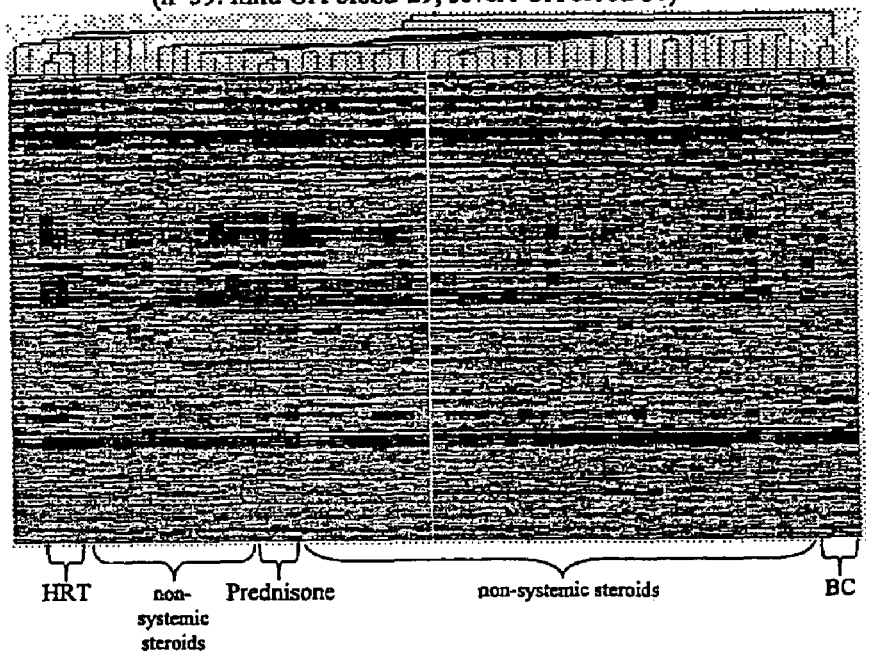
FIG. 34 shows a diagrammatic representation of gene expression profiles of blood samples from individuals who were identified as having OA and being one form of systemic steroids.

Table 3AD shows the identity of those genes that are differentially expressed in blood from patients taking either birth control, prednisone or hormone replacement therapy and presenting with OA as depicted in FIG. 34.

Table 4 shows 102 EST sequences of Tables 3A-3AD with "no-significant match" to known gene sequences.

Table 5 shows a list of genes showing greater than two fold differential expression in CAD peripheral blood cells vs. normal blood cells.

The following examples are given for the purpose of illustrating various embodiments of the invention and are not meant to limit the present invention in any fashion.

EXAMPLE 1

Construction of a cDNA Library

RNA extracted from human tissues (including fetal heart, adult heart, liver, brain, prostate gland and whole blood) were used to construct unidirectional cDNA libraries. The first mammalian heart cDNA library was constructed as early as 1982. Since then, the methodology has been revised and optimal conditions have been developed for construction of human heart and hematopoietic progenitor cDNA libraries (Liew et al., 1984; Liew 1993, Claudio et al., 1998). Most of the novel genes which were identified by sequence annotation can now be obtained as full length transcripts.

EXAMPLE 2

Catalogue of EST Database

Random partial sequencing of expressed sequence tags (ESTs) of cDNA clones from the blood cell library was carried out to establish an EST database of blood. The known genes as derived from the ESTs were categorized into seven major cellular functions (Hwang, Dempsey et al., 1997). The preparation of the chondrocyte-specific EST database is reported in WO 02/070737, which is hereby incorporated by reference in its entirety.

EXAMPLE 3

Differential Screening of cDNA Library cDNA probes generated from transcripts of each tissue were used to hybridize the blood cell cDNA clones or chondrocyte cDNA clones (Liew et al., 1997; WO 02/070737). The "positive" signals which were hybridized with P-labelled cDNA probes were defined as genes which shared identity with blood and respective tissues. The "negative" spots which were not exposed to P-labelled cDNA probes were considered to be blood-cell-enriched or low frequency transcripts.

EXAMPLE 4

Reverse Transcriptase-Polymerase Chain Reaction (RT-PCR) Assay

RNA extracted from samples of human tissue was used for RT-PCR analysis (Jin et al. 1990). Three pairs of forward and reverse primers were designed for human cardiac beta-myosin heavy chain gene (βMyHC), amyloid precursor protein (APP) gene and adenomatous polyposis-coli protein (APC) gene. The PCR products were also subjected to automated DNA sequencing to verify the sequences as derived from the specific transcripts of blood.

EXAMPLE 5

Detection of Tissue Specific Gene Expression in Human Blood Using RT-PCR

The beta-myosin heavy chain gene (βMyHC) transcript (mRNA) is known to be highly expressed in ventricles of the human heart. This sarcomeric protein is important for heart muscle contraction and its presence would not be expected in other non-muscle tissues and blood. In 1990, the gene for human cardiac βMyHC was completely sequenced (Liew et al. 1990) and was comprised of 41 exons and 42 introns.

The method of reverse transcription polymerase chain reaction (RT-PCR) was used to determine whether this cardiac specific mRNA is also present in human blood. A pair of primers was designed; the forward primer (SEQ ID No. 3) was on the boundary of exons 21 and 22, and the reverse primer (SEQ ID No. 4) was on the boundary of exons 24 and 25. This region of mRNA is only present in βMyHC and is not found in the alpha-myosin heavy chain gene (αMyHC).

A blood sample was first treated with lysing buffer and then undergone centrifuge. The resulting pellets were further processed with RT-PCR. RT-PCR was performed using the total blood cell RNA as a template. A nested PCR product was generated and used for sequencing. The sequencing results were subjected to BLAST and the identity of exons 21 to 25 was confirmed to be from βMyHC (FIG. 1A).

Using the same method just described, two other tissue specific genes—amyloid precursor protein (APP, forward primer, SEQ ID No. 7; reverse primer, SEQ ID No. 8) found in the brain and associated with Alzheimer's disease, and adenomatous polyposis coli protein (APC) found in the colon and rectum and associated with colorectal cancer (Groden et al. 1991; Santoro and Groden 1997)—were also detected in the RNA extracted from human blood (FIG. 1B).

EXAMPLE 6

Multiple RT-PCR Analysis on a Drop of Blood From a Normal/Diseased Individual

Figure 2:
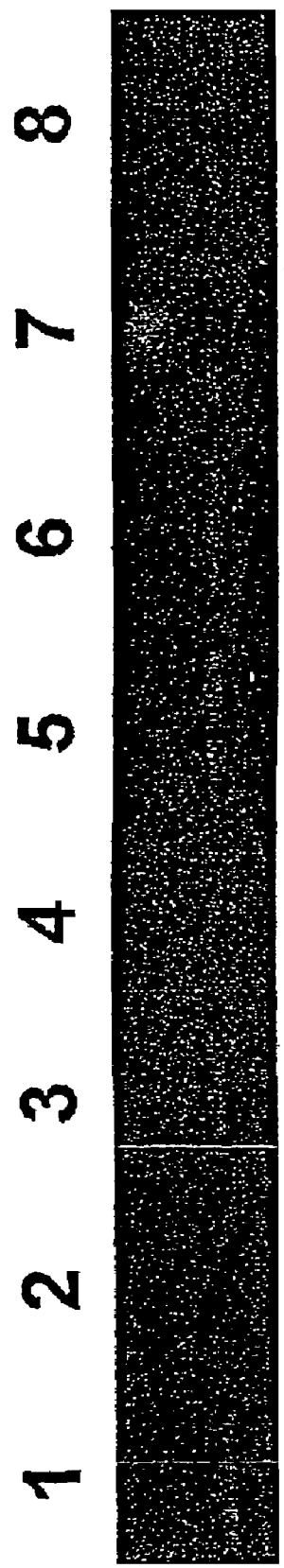
FIG. 2 shows quantitative RT-PCR analysis performed on RNA samples extracted from a drop of blood. Forward primer (5'-GCCCTCTGGGGACCTGAC-3', SEQ ID No. 1) of exon 1 and reverse primer (5'-CCCACCTGCAGGTCCTCT-3", SEQ ID No. 2) of exons 1 and 2 of insulin gene. Blood samples of 4 normal subjects were assayed. Lanes 1, 3, 5 and 7 represent overnight "fasting" blood sample and lanes 2, 4, 6 and 8 represent "non-fasting" samples.

A drop of blood was extracted to obtain RNA to carry out quantitative RT-PCR analysis. Specific primers for the insulin gene were designed: forward primer (5'-GCCCTCTGGG-GACCTGAC-3', SEQ ID NO 1) of exon 1 and reverse primer (5'-CCCACCTGCAGGTCCTCT-3", SEQ ID NO 2) of exons 1 and 2 of insulin gene. Such reverse primer was obtained by deleting the intron between the exons 1 and 2. Blood samples of 4 normal subjects were assayed. It was found that the insulin gene is expressed in the blood and the quantitative expression of the insulin gene in a drop of blood is influenced by fasting and non-fasting states of normal healthy subjects (FIG. 2). This very low level of expression of the insulin gene reflects the phenotypic status of a person and strongly suggests that there is a physiological and pathological role for its expression, contrary to the basal or illegitimate theory of transcription suggested by Chelly et al. (1989) and Kimoto (1998).

Figure 3:
FIG. 3 shows quantitative RT-PCR analysis performed on RNA samples extracted from a drop of blood. Lanes 1 and 2 represent normal healthy person and lane 3 represents late-onset diabetes (Type II) and lane 4 represents asymptomatic diabetes.

Same quantitative RT-PCR analysis was performed using insulin specific primers on RNA samples extracted from a drop of blood from a normal healthy person, a person having late-onset diabetes (Type II) and a person having asymptomatic diabetes. It was found that the insulin gene is expressed differentially amongst subjects that are healthy, diagnosed as type II diabetic, and also in an asymptomatic preclinical patient (FIG. 3).

Similarly, specific primers for the atrial natriuretic factor (ANF) gene were designed (forward primer, SEQ ID No. 5; reverse primer, SEQ ID No. 6) and RT-PCR analysis was performed on a drop of blood. ANF is known to be highly expressed in heart tissue biopsies and in the plasma of heart failure patients. However, atrial natriuretic factor was observed to be expressed in the blood and the expression of the atrial natriuretic factor gene is significantly higher in the blood of patients with heart failure as compared to the blood of a normal control patient.

Specific primers for the zinc finger protein gene (ZFP, forward primer, SEQ ID No. 9; reverse primer, SEQ ID No. 10) were also designed and RT-PCR analysis was performed on a drop of blood. ZFP is known to be high in heart tissue biopsies of cardiac hypertrophy and heart failure patients. In the present study, the expression of ZFP was observed in the blood as well as differential expression levels of ZFP amongst the normal, diabetic and asymptomatic preclinical subjects (FIG. 4); although neither of the non-normal subjects has been specifically diagnosed as suffering from cardiac hypertrophy and/or heart failure, the higher expression levels of the ZFP gene in their blood may indicate that these subjects are headed in that general direction.

Figure 4:
FIG. 4 shows multiple RT-PCR assay in a drop of blood. Primers were derived from insulin gene (INS), zinc-finger protein gene (ZFP) and house-keeping gene (GADH). Lane 1 represents normal person. Lane 2 represents late-onset diabetes and lane 3 represents asymptomatic diabetes.

It was hypothesized that a housekeeping gene such as glyceraldehyde dehydrogenase (GADH) which is required and highly expressed in all cells would not be differentially expressed in the blood of normal vs. disease subjects. This hypothesis was confirmed by RT-PCR using GADH specific primers (FIG. 4). Thus, GADH is useful as an internal control.

Standardized levels of insulin gene or ZFP gene expressed in a drop of blood were estimated using a housekeeping gene as an internal control relative to insulin or ZFP expressed (FIGS. 5A & 5B). The levels of insulin gene expressed in each fractionated cell from whole blood were also standardized and shown in FIG. 5C.

EXAMPLE 7

Human Blood Cell cDNA Library

In order to further substantiate the present invention, differential screening of the human blood cell cDNA library was conducted. cDNA probes derived from human blood, adult heart or brain were respectively hybridized to the human blood cDNA library clones. As shown in FIG. 7, more than 95% of the "positively" identified clones are identical between the blood and other tissue samples.

DNA sequencing of randomly selected clones from the human whole blood cell cDNA library was also performed. This allowed information regarding the cellular function of blood to be obtained concurrently with gene identification. More than 20,000 expressed sequence tags (ESTs) have been generated and characterized to date, 17.6% of which did not result in a statistically significant match to entries in the GenBank databases and thus were designated as "Novel"

ESTs. These results are summarized in FIG. 7 together with the seven cellular functions related to percent distribution of known genes in blood and in the fetal heart.

From 20,000 ESTs, 1,800 have been identified as known genes which may not all appear in the hemapoietic system. For example, the insulin gene and the atrial natriuretic factor gene have not been detected in these 20,000 ESTs but their transcripts were detected in a drop of blood, strongly suggesting that all transcripts of the human genome can be detected by performing RT-PCR analysis on a drop of blood.

In addition, approximately 400 novel genes have been identified from the 20,000 ESTs characterized to date, and these will be subjected to full length sequencing and open reading frame alignment to reduce the actual number of novel ESTs prior to screening for disease markers.

Analysis of the approximately 6,283 ESTs which have known matches in the GenBank databases revealed that this dataset represents over 1,800 unique genes. These genes have been catalogued into seven cellular functions. Comparisons of this set of unique genes with ESTs derived from human brain, heart, lung and kidney demonstrated a greater than 50% overlap in expression (Table 1).

TABLE 1

Overlap of Genes Expressed in Blood

| Tissue | UniGene* | Overlap |
| --- | --- | --- |
| Brain | 19,158 | 70% |
| Heart | 17,021 | 67% |
| Kidney | 19,414 | 69% |
| Liver | 22,836 | 71% |
| Lung | 22,209 | 75% |

*Known gene cluster numbers found in a corresponding tissue in UniGene.

There are about 5,100 unique known genes from the over 25,000 ESTs obtained from human blood cDNA libraries. These genes were searched against human UniGene, Build #160 (with a total of 111,064 clusters).

EXAMPLE 8

Blood Cell ESTs

The results from the differential screening clearly indicate that the transcripts expressed in the whole blood are reflective of genes expressed in all cells and tissues of the body. More than 95% of detectable spots were identical from two different tissues. The remaining 5% of spots may represent cell- or tissue-specific transcripts; however, results obtained from partial sequencing to generate ESTs of these clones revealed most of them not to be cell- or tissue-specific transcripts. Therefore, the negative spots are postulated to be reflective of low abundance transcripts in the tissue from which the cDNA probes were derived.

An alternative approach that was employed to identify transcripts expressed at low levels is the large-scale generation of expressed sequence tags (ESTs). There is substantial evidence regarding the efficiency of this technology to detect previously characterized (known) and uncharacterized (unknown or novel) genes expressed in the cardiovascular system (Hwang & Dempsey et al. 1997). In the present invention, 20,000 ESTs have been produced from a human blood cell cDNA library and resulted in the identification of approximately 1,800 unique known genes (Table 2)

In the most recent GenBank release, analysis of more than 300,000 ESTs in the database (dbESTs) generated more than 48,000 gene clusters which are thought to represent approximately 50% of the genes in the human genome. Only 4,800 of the dbESTs are blood-derived. In the present invention, 20,000 ESTs have been obtained to date from a human blood cDNA library, which provides the world's most informative database with respect to blood cell transcripts. From the limited amount of information generated so far (i.e. 1,800 unique genes), it has already been determined that more than 50% of the transcripts are found in other cells or tissues of the human body (Table 2). Thus, it is expected that by increasing the number of ESTs generated, more genes will be identified that have an overlap in expression between the blood and other tissues. Furthermore, the transcripts for several genes which are known to have tissue-restricted patterns of expression (i.e. βMyHC, APP, APC, ANF, ZFP) have also been demonstrated to be present in blood.

Most recently, a cDNA library of human hematopoietic progenitor stem cells has also been constructed. From the limited set of 1,000 ESTs, there are at least 200 known genes that are shared with other tissue related genes (Claudio et al. 1998).

Table 2 demonstrates the expression of known genes of specific tissues in blood cells. Previously, only the presence of "housekeeping" genes would have been expected. Additionally, the presence of at least 25 of the currently known 500 genes corresponding to molecular drug targets was detected. These molecular drug targets are used in the treatment of a variety of diseases which involve inflammation, renal and cardiovascular function, neoplastic disease, immunomodulation and viral infection (Drews & Ryser, 1997). It is expected that additional novel ESTs will represent future molecular drug targets.

EXAMPLE 9

Blood cDNA chip Microarray Data Analysis of gene expression profiles of blood samples from individuals having coronary artery disease as compared with gene expression profiles from normal individuals.

A microarray was constructed using cDNA clones from a human peripheral blood cell cDNA library, as described herein. A total of 10,368 polymerase chain reaction (PCR) products of the clones from the human peripheral blood cell cDNA library described herein were arrayed using GNS 417 arrayer (Affymetrix). RNA for microarray analysis was isolated from whole blood samples obtained from three male and one female patients with coronary heart disease (80-90% stenosis) receiving vascular extension drugs and awaiting bypass surgery, and three healthy male controls.

A method of high-fidelity mRNA amplification from 1 pg of total RNA sample was used. Cy5- or Cy3-dUTP was incorporated into cDNA probes by reverse transcription of antisense RNA, primed by oligo-dT. Labelled probes were purified and concentrated to the desired volume. Pre-hybridization and hybridization were performed following Hegde's protocol (Hegde P et al., A concise guide to cDNA microarray analysis. Biotechniques, 2000; 29: 548-56). After overnight hybridization and washing, hybridization signals were detected with a GMS 418 scanner at 635-nm (Cy5) and 532-nm (Cy3) wave lengths (see FIG. 24). Two RNA pools were labelled alternatively with Cy5- and Cy3-dUTP, and each experiment was repeated twice. Cluster analysis using GeneSpring™ 4.1.5 (Silicon Genetics) revealed two distinct groups consisting of four CAD and three normal control samples. Two images scanned at different wavelengths were super-imposed. Individual spots were identified on a customized grid. Of 10,368 spots, 10,012 (96.6%) were selected after the removal of spots with irregular shapes. Data quality was assessed with values of Ch1GTB2 and Ch2GTB2 provided by ScanAlyze. Only spots with Ch1GTB2 and Ch2GTB2 over 0.50 were selected. After evaluation of signal intensities, 8750 (84.4%) spots were left. Signal intensities were normalized using a scatter-plot of the signal intensities of the two channels. After normalization, the expression ratios of β-actin were 1.00+0 21, 1.11+0.22, 1.14+0.20 and 1.30+0.18 (24 samples of β-actin were spotted on this slide as the positive control) in the four images. Gene differential expression was assessed as the ratio of two wave-length signal intensities. Spots showing a differential expression more than twofold in all four experiments were identified as peripheral blood cell, differentially expressed candidate genes in CAD. 108 genes are differentially expressed in CAD peripheral blood cells. 43 genes are down-regulated in CAD blood cells and 65 are upregulated (see Table 5). Functional characterization of these genes shows that differential expression takes place in every gene functional category, indicating that profound changes occur in CAD blood cells.

The differential expression of three genes, pro-platelet basic protein (PBP), platelet factor 4 (PF4) and coagulation factor XIII A1 (F13A), initially identified in the microarray data analysis, was further examined by reverse transcriptase-PCR (RT-PCR) using the Titan One-tube RT-PCR kit (Boehringer Mannheim). Reaction solution contains 0.2 mM each dNTP, 5 mM DTT, 1.5 mM MgCl 0.1 pg of total RNA from each sample and 20 pmol each of left and right primers of PBP (5'-GGTGCTGCTGCTTCTGTCAT-3' and 5'-GGCA-GATTTTCCTCCCATCC-3'), F13A (5'-AGTCCACCGT-GCTAACCATC-3' and 5'-AGGGAGTCACTGCTCATGCT-3') and PF4 (5' GTTGCTGCTCCTGCCACTT 3' and 5' GTGGCTATCAGTTGGGCAGT-3'). RT-PCR steps are as follows: 1. reverse-transcription: 30 min at 60° C.; 2. PCR: 2 min at 94° C., followed by 30-35 cycles (as optimized for each gene) for 30 s at 94° C., 30 s at optimized annealing temperature and 2 min at 68° C.; 3. final extension: 7 min at 68° C. PCR products were electrophoresed on 1.5% agarose gels. Human (β-actin primers (5'-GCGAGAAGATGACCCA-GATCAT-3' and 5'-GCTCAGGAGGAGCAATGATCTT-3') were used as the internal control. The RT-PCR analysis confirmed that the expression of the three secreted proteins: PBP, PF4 and F13A were all upregulated in CAD blood cells (see FIG. 23).

TABLE 5

|  | Accession number | Fold (average) | Functional category | Protein Accession Number |
|---|---|---|---|---|
| Upregulated gene in CAD |  |  |  |  |
| REV3-like, catalytic subunit of DNA polymerase zeta | AF035537 | 2.3 | Cell cycle | NP_002903 |
| TGFB1-induced anti-apoptotic factor 1 | D86970 | 2.2 | Cell cycle | NP_510880 |
| A disintegrin and metalloproteinase domain 10 | AA044656 | 2.7 | Cell signaling | NP_001101 |
| Centaurin, delta 2 | AA351412 | 2 | Cell signaling | NP_631920 |
| Chloride intracellular channel 4 | AA411940 | 2.2 | Cell signaling | NP_039234 |
| Endothelin receptor typeA | D90348 | 2.1 | Cell signaling | NP_001948 |
| Glutamate receptor, ionotropic | N33821 | 2.4 | Cell signaling | NP_777567 |
| Mitogen-activated protein kinase 7 | L38486 | 3.7 | Cell signaling | NP_002395 |
| Mitogen-activated protein kinase kinase kinase 7 | AB009356 | 4.5 | Cell signaling | NP_663306 |
| Myristoylated alanine-rich protein kinase C substrate | D10522 | 2.5 | Cell signaling | NP_002347 |
| NIMA-related kinase 7 | AA093324 | 3.5 | Cell signaling | NP_598001 |
| PAK2 | AA262968 | 3.5 | Cell signaling | Q13177 |
| Phospholipid scramblase 1 | AA054476 | 3.3 | Cell signaling | NP_066928 |
| Serum deprivation response | Z30112 | 4.5 | Cell signaling | NP_004648 |
| Adducin 3 | AA029158 | 2.9 | Cell structure | NP_063968 |
| Desmin | AF167579 | 4.4 | Cell structure | NP_001918 |
| Fibromodulin | W23613 | 2.9 | Cell structure | NP_002014 |
| Laminin, beta 2 | S77512 | 2.2 | Cell structure | NP_002283 |
| Laminin, beta 3 | L25541 | 2.4 | Cell structure | NP_000219 |
| Osteonectin | Y00755 | 3.1 | Cell structure | NP_003109 |
| CD59 antigen p18-20 | W01111 | 2.4 | Cell/organism defense | NP_000602 |
| Clusterin | M64722 | 3.5 | Cell/organism defense | NP_001822 |
| F13A | M14539 | 2.1 | Cell/organism defense | NP_000120 |
| Defensin, alpha 1 | M26602 | 4.2 | Cell/organism defense | NP_004075 |
| PF4 | M25897 | 2.1 | Cell/organism defense | NP_002610 |
| PBP | M54995 | 5.5 | Cell/organism defense | NP_002695 |

TABLE 5-continued

| | Accession number | Fold (average) | Functional category | Protein Accession Number |
|---|---|---|---|---|
| E2F transcription factor 3 | D38550 | 2.1 | Gene expression | NP_001940 |
| Early growth response 1 | M62829 | 2.7 | Gene expression | NP_001955 |
| Eukaryotic translation elongation factor 1 alpha 1 | N86030 | 2.3 | Gene expression | NP_001393 |
| Eukaryotic translation initiation factor 4E | M15353 | 2.1 | Gene expression | NP_001959 |
| F-box and WD-40 domain protein 1B | AB014596 | 2.7 | Gene expression | NP_387449 |
| Makorin, ring finger protein, 2 | AA331966 | 2.1 | Gene expression | NP_054879 |
| Non-canonical ubiquitin-conjugating enzyme 1 | N92776 | 2.5 | Gene expression | NP_057420 |
| Nuclear receptor subfamily 1, group I, member 3 | Z30425 | 4.7 | Gene expression | NP_005113 |
| Ring finger protein 11 | T08927 | 3 | Gene expression | NP_055187 |
| Transducin-like enhancer of split 1 | M99435 | 3.3 | Gene expression | NP_005068 |
| Alkaline phosphatase, liver/bone/kidney | AB011406 | 2.2 | Metabolism | NP_000469 |
| Annexin A3 | M63310 | 3.4 | Metabolism | NP_005130 |
| Branched chain aminotransferase 1, cytosolic | AA336265 | 4.8 | Metabolism | NP_005495.1 |
| Cytochrome b | AF042500 | 2.5 | Metabolism | |
| Glutaminase | D30931 | 2.6 | Metabolism | NP_055720 |
| Lysophospholipase I | AF035293 | 2.8 | Metabolism | NP_006321 |
| NADH dehydrogenase 1, subcomplex unknown 1, 6 kDa | AA056111 | 2.5 | Metabolism | NP_002485 |
| Phosphofructokinase | M26066 | 2.2 | Metabolism | NP_000280 |
| Ubiquinol-cytochrome c reductase binding protein | M22348 | 2.5 | Metabolism | NP_006285 |
| CGI-110 protein | AA341061 | 2.4 | Unclassified | NP_057131 |
| Dactylidin | H95397 | 2.7 | Unclassified | NP_112225 |
| Deleted in split-hand/split-foot 1 region | T24503 | 2.4 | Unclassified | NP_006295 |
| Follistatin-like 1 | R14219 | 2.7 | Unclassified | NP_009016 |
| FUS-interacting protein 1 | W37945 | 2.8 | Unclassified | NP_473357 |
| Hypothetical protein FLJ12619 | W47233 | 7 | Unclassified | NP_112201 |
| Hypothetical protein from EUROIMAGE 588495 | N68247 | 2.7 | Unclassified | |
| Hypothetical protein LOC51315 | AA251423 | 2.2 | Unclassified | NP_057702 |
| KIAA1705 protein | T80569 | 2.7 | Unclassified | NP_009121.1 |
| Mesoderm induction early response 1 | AI650409 | 2.2 | Unclassified | NP_065999 |
| Phosphodiesterase 4D-interacting protein | AA740661 | 2.5 | Unclassified | NP_055459 |
| Preimplantation protein 3 | D59087 | 2.5 | Unclassified | NP_056202 |
| Putative nuclear protein ORF1-FL49 | W33098 | 2.8 | Unclassified | NP_115788 |
| Similar to rat nuclear ubiquitous casein kinase 2 | H09434 | 2.2 | Unclassified | Q9H1E3 |
| Similar to RIKEN | AA297412 | 2.5 | Unclassified | T02670 |
| Spectrin, beta | AI334431 | 2.5 | Unclassified | Q01082 |
| Stromal cell-derived factor receptor 1 | H71558 | 4.1 | Unclassified | NP_816929 |
| Thioredoxin-related protein | AA421549 | 2.8 | Unclassified | NP_110437 |
| Transmembrane 4 superfamily member 2 | D29808 | 2.4 | Unclassified | NP_004606 |
| Tumor endothelial marker 8 | D79964 | 2.5 | Unclassified | NP_444262 |
| Downregulated gene in CAD | | | | |
| CASP8 and FADD-like apoptosis regulator | AF015450 | 0.45 | Cell cycle | NP_003870 |
| CD81 antigen | M33680 | 0.41 | Cell cycle | NP_004347 |
| Cell division cycle 25B | M81934 | 0.4 | Cell cycle | NP_068660 |
| DEAD/H (Asp-Glu-Ala-Asp/His) box polypeptide 27 | AA985699 | 0.42 | Cell cycle | NP_694705 |

TABLE 5-continued

| | Accession number | Fold (average) | Functional category | Protein Accession Number |
|---|---|---|---|---|
| F-box and leucine-rich repeat protein 11 | R98291 | 0.27 | Cell cycle | NP_036440 |
| Minichromosome maintenance deficient 3 associated protein | H10286 | 0.43 | Cell cycle | NP_003897 |
| Protein phosphatase 2, regulatory subunit A, alpha isoform | J02902 | 0.48 | Cell cycle | NP_055040 |
| Thyroid autoantigen 70 kDa | J04607 | 0.25 | Cell cycle | NP_001460 |
| A disintegrin and metalloproteinase domain 17 | R32760 | 0.37 | Cell signaling | |
| A kinase anchor protein 13 | M90360 | 0.31 | Cell signaling | NP_658913 |
| Calpastatin | AF037194 | 0.39 | Cell signaling | NP_006471 |
| Diacylglycerol kinase, alpha 80 kDa | AF064770 | 0.44 | Cell signaling | NP_001336 |
| gamma-aminobutyric acid B receptor, 1 | AJ012187 | 0.42 | Cell signaling | NP_068705 |
| Inositol polyphosphate-5-phosphatase, 145 kDa | U84400 | 0.41 | Cell signaling | NP_005532 |
| Lymphocyte-specific protein tyrosine kinase | X05027 | 0.45 | Cell signaling | NP_005347 |
| RAP1B, member of RAS oncogene family | P09526 | 0.4 | Cell signaling | P09526 |
| Ras association (RalGDS/AF-6) domain family 1 | AF061836 | 0.43 | Cell signaling | NP_733835 |
| CDC42-effector protein 3 | AF104857 | 0.28 | Cell signaling | NP_006440 |
| Leupaxin | AF062075 | 0.31 | Cell signaling | NP_004802 |
| Annexin A6 | D00510 | 0.45 | Cell structure | NP_004024 |
| RAN-binding protein 9 | AB008515 | 0.41 | Cell structure | NP_005484 |
| Thymosin, beta 10 | M20259 | 0.26 | Cell structure | NP_066926 |
| GranzymeA | M18737 | 0.17 | Cell/organism defense | NP_006135 |
| ThromboxaneA synthase 1 | M80646 | 0.44 | Cell/organism defense | NP_112246 |
| Coatomer protein complex, subunit beta | AA357332 | 0.39 | Gene expression | NP_057535 |
| Cold-inducible RNA-binding protein | H39820 | 0.27 | Gene expression | NP_001271 |
| Leucine-rich repeat interacting protein 1 | U69609 | 0.44 | Gene expression | NP_004726 |
| Proteasome subunit, alpha type, 3 | D00762 | 0.31 | Gene expression | NP_687033 |
| Proteasome subunit, alpha type, 7 | AF022815 | 0.35 | Gene expression | NP_689468 |
| Protein phosphatase 1G, gamma isoform | AI417405 | 0.5 | Gene expression | NP_817092 |
| Ribonuclease/angiogenin inhibitor | M36717 | 0.44 | Gene expression | NP_002930 |
| RNA-binding protein-regulatory subunit | AF021819 | 0.3 | Gene expression | NP_009193 |
| Signal transducer and activator of transcription 6 | U16031 | 0.45 | Gene expression | NP_003144 |
| Transcription factor A, mitochondrial | M62810 | 0.41 | Gene expression | NP_036383 |
| Ubiquitin-specific protease 4 | AF017306 | 0.31 | Gene expression | NP_003354 |
| Dehydrogenase/reductase SDR family member 1 | AA100046 | 0.46 | Metabolism | NP_612461 |
| Solute carrier family 25, member 6 | J03592 | 0.3 | Metabolism | NP_001627 |
| Amplified in osteosarcoma | U41635 | 0.45 | Unclassified | NP_006803 |
| Expressed in activated T/LAK lymphocytes | C00577 | 0.45 | Unclassified | NP_009198 |
| Integral inner nuclear membrane protein | W00460 | 0.4 | Unclassified | NP_055134 |
| Phosphodiesterase 4D-interacting protein | T95969 | 0.45 | Unclassified | NP_055459 |
| Tumor endothelial marker 7 precursor | N93789 | 0.45 | Unclassified | NP_065138 |
| Wiskott-Aldrich syndrome protein interacting protein | AF031588 | 0.22 | Unclassified | NP_003378 |

EXAMPLE 10

ChondroChip™ Microarray Data Analysis of gene expression profiles of blood samples from co-morbid individuals having osteoarthritis and hypertension as compared with gene expression profiles from normal individuals.

This example demonstrates the use of the claimed invention to detect differential gene expression in blood samples taken from patients with osteoarthritis and hypertension as compared to blood samples taken from healthy patients.

As used herein, the term "hypertension" is defined as high blood pressure or elevated arterial pressure. Patients identified with hypertension herein include persons who have an increased risk of developing a morbid cardiovascular event and/or persons who benefit from medical therapy designed to treat hypertension. Patients identified with hypertension also can include persons having systolic blood pressure of >130 mm Hg or a diastolic blood pressure of >90 mm Hg or a person takes antihypertensive medication.

Osteoarthritis (OA), as used herein also known as "degenerative joint disease", represents failure of a diarthrodial (movable, synovial-lined) joint. It is a condition, which affects joint cartilage, and or subsequently underlying bone and supporting tissues leading to pain, stiffness, movement problems and activity limitations. It most often affects the hip, knee, foot, and hand, but can affect other joints as well.

OA severity can be graded according to the system described by Marshall (Marshall K W. J. Rheumatol, 1996: 23(4) 582-85). Briefly, each of the six knee articular surfaces was assigned a cartilage grade with points based on the worst lesion seen on each particular surface. Grade 0 is normal (0 points), Grade I cartilage is soft or swollen but the articular surface is intact (1 point). In Grade II lesions, the cartilage surface is not intact but the lesion does not extend down to subchondral bone (2 points). Grade III damage extends to subchondral bone but the bone is neither eroded nor eburnated (3 points). In Grade IV lesions, there is eburnation of or erosion into bone (4 points). A global OA score is calculated by summing the points from all six cartilage surfaces. If there is any associated pathology, such as meniscus tear, an extra point will be added to the global score. Based on the total score, each patient is then categorized into one of four OA groups: mild (1-6), moderate (7-12), marked (13-18), and severe (>18). As used herein, patients identified with OA may be categorized in any of the four OA groupings as described above.

Blood samples were taken from patients who were diagnosed with osteoarthritis and hypertension as defined herein. Gene expression profiles were then analysed and compared to profiles from patients unaffected by any disease. In each case, the diagnosis of osteoarthritis and hypertension was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with disease as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 8 shows a diagrammatic representation of gene expression profiles of blood samples from individuals having hypertension and osteoarthritis as compared with gene expression profiles from normal individuals. Expression profiles were generated using GeneSpring™ software analysis as described herein. Each column represents the hybridization pattern resulting from a single individual. In this example, hypertensive patients also presented with OA, as described herein. Normal individuals have no known medical conditions and were not taking any known medication. Hybridizations to create said gene expression profiles were done using the ChondroChip™. A dendogram analysis is shown above. Samples are clustered and marked as representing patients who are hypertensive or normal. The "*" indicates those patients who abnormally clustered as either hypertensive, or normal despite presenting with the reverse. The number of hybridizations profiles determined for either hypertensive patients or normal individuals are shown. 861 differentially expressed genes were identified as being differentially expressed with a p value of <0.05 as between the hypertensive patients and normal individuals. The identity of the differentially expressed genes is shown in Table 3A.

Classification or class prediction of a test sample as either having hypertension and OA or being normal can be done using the differentially expressed genes as shown in Table 3A in combination with well known statistical algorithms for class prediction as would be understood by a person skilled in the art and described herein. Commercially available programs such as those provided by Silicon Genetics (e.g. GeneSpring™) for Class Predication are also available.

EXAMPLE 10A

ChondroChip™ Microarray Data Analysis of gene expression profiles of blood samples from individuals having osteoarthritis and hypertension as compared with gene expression profiles from patients having osteoarthritis only.

This example demonstrates the use of the claimed invention to detect differential gene expression in blood samples taken from co-morbid patients with osteoarthritis and hypertension as compared to blood samples taken from OA patients only.

Blood samples were taken from patients who were diagnosed with osteoarthritis and hypertension as defined herein. Gene expression profiles were then analysed and compared to profiles from patients having OA only. In each case, the diagnosis of osteoarthritis and/or hypertension was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with disease as compared to OA patients only was determined by statistical analysis using the Wilcox Mann Whitney rank sum test (Glantz S A., Primer of Biostatistics., 5th ed., New York, USA: McGraw-Hill Medical Publishing Division, 2002).

Expression profiles were generated using GeneSpring™ software analysis as described herein (data not shown). The gene list generated from this analysis was identified and those genes previously identified in Table 3A removed so as to identify those genes which are unique to hypertension. 790 differentially expressed genes were identified as being differentially expressed with a p value of <0.05 as between the OA and hypertensive patients when compared with OA individuals. 577 genes were identified as unique to hypertension. The identity of these differentially expressed genes are shown in Table 3P. A gene list is also provided of the 213 genes which were found in common as between those genes identified in Table 3A and genes differentially expressed in blood samples taken from patients with osteoarthritis and hypertension as compared to blood samples taken from OA patients only. The identity of these intersecting differentially expressed genes is shown in Table 3Q and a venn diagram showing the relationship between the various groups of gene lists is found in FIG. 29.

Classification or class prediction of a test sample as having hypertension or not having hypertension can be done using the differentially expressed genes as shown in Table 3P as the predictor genes in combination with well known statistical algorithms as would be understood by a person skilled in the art and described herein. Commercially available programs such as those provided by Silicon Genetics (e.g. GeneSpring™) for Class Predication are also available. Classification of individuals as having both OA and hypertension using the genes in Table 3Q can also be performed.

EXAMPLE 11

ChondroChip™ Microarray Data Analysis of gene expression profiles of blood samples from co-morbid individuals having osteoarthritis and obesity as compared with gene expression profiles from normal individuals.

This example demonstrates the use of the claimed invention to detect differential gene expression in blood samples taken from patients with obesity and OA as compared to blood samples taken from healthy patients.

As used herein, "obesity" is defined as an excess of adipose tissue that imparts a health risk. Obesity is assessed in terms of height and weight in the relevance of age. Patients who are considered obese include, but are not limited to, patients having a body mass index or BMI ((defined as body weight in kg divided by (height in meters)$^2$) greater than or equal to 30.0.

Blood samples were taken from patients who were diagnosed with osteoarthritis and obesity as defined herein. Gene expression profiles were then analysed and compared to profiles from patients unaffected by any disease. In each case, the diagnosis of the disease was corroborated by a skilled Board certified physician. Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with disease as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 9 shows a diagrammatic representation of gene expression profiles of blood samples from individuals who were identified as obese as described herein as compared with gene expression profiles from normal individuals. Expression profiles were generated using GeneSpring™ software analysis as described herein. Each column represents the hybridization pattern resulting from a single individual. In this example, obese patients also presented with OA, as described herein. Normal individuals have no known medical conditions and were not taking any known medication. Hybridizations to create said gene expression profiles were done using the ChondroChip™. A dendogram analysis is shown above. Samples are clustered and marked as representing patients who are obese or normal. The "*" indicates those patients who abnormally clustered as either obese or normal despite presenting with the reverse. The number of hybridization profiles determined for obese patients with OA and normal individuals are shown. 913 genes were identified as being differentially expressed with a p value of <0.05 as between the obese patients with OA and normal individuals is noted. The identity of the differentially expressed genes is shown in Table 3B.

Classification or class prediction of a test sample as either having obesity and OA or being normal can be done using the differentially expressed genes as shown in Table 3B in combination with well known statistical algorithms as would be understood by a person skilled in the art and described herein. Commercially available programs such as those provided by Silicon Genetics (e.g. GeneSpring™) for Class Predication are also available.

EXAMPLE 11A

ChondroChip™ Microarray Data Analysis of gene expression profiles of blood samples from co-morbid individuals having osteoarthritis and obesity as compared with gene expression profiles from patients having osteoarthritis only.

This example demonstrates the use of the claimed invention to detect differential gene expression in blood samples taken from patients with obesity and OA as compared to blood samples taken from patients with OA only.

Blood samples were taken from patients who were diagnosed with osteoarthritis and obesity as defined herein. Gene expression profiles were then analysed and compared to profiles from patients affected by OA only.

In each case, the diagnosis of the disease was corroborated by a skilled Board certified physician. Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with obesity and OA as compared to OA patients only was determined by statistical analysis using the Wilcox Mann Whitney rank sum test (Glantz S A., Primer of Biostatistics., 5th ed. New York, USA: McGraw-Hill Medical Publishing Division, 2002).

Expression profiles were generated using GeneSpring™ software analysis as described herein (data not shown). 671 genes were identified as being differentially expressed with a p value of <0.05 as between the obese patients with OA and those patients with only OA. Those genes previously identified in Table 3B were removed so as to identify those genes which are unique to obesity. The identity of these 519 genes unique to obesity are shown in Table 3R. A gene list is also provided of those genes which were found in common as between those genes identified in Table 3B and genes differentially expressed in blood samples taken from patients with osteoarthritis and obesity as compared to blood samples taken from OA patients only. 152 genes are shown in Table 3S. A venn diagram showing the relationship between the various groups of gene lists is found in FIG. 30.

Classification or class prediction of a test sample as having obesity or not having obesity can be done using the differentially expressed genes as shown in Table 3R as the predictor genes in combination with well known statistical algorithms as would be understood by a person skilled in the art and described herein. Commercially available programs such as those provided by Silicon Genetics (e.g. GeneSpring™) for Class Predication are also available. Classification of individuals as having both OA and obesity using the genes in Table 3S can also be performed.

EXAMPLE 12

ChondroChip™ Microarray Data Analysis of gene expression profiles of blood samples from co-morbid individuals having osteoarthritis and allergies as compared with gene expression profiles from normal individuals.

This example demonstrates the use of the claimed invention to detect differential gene expression in blood samples taken from patients with allergies as compared to blood samples taken from healthy patients.

As used herein, "allergies" encompasses diseases and conditions wherein a patient demonstrates a hypersensitive or allergic reaction to one or more substances or stimuli such as drugs, food stuffs, plants, animals etc. and as a result has an increased immune response. Such immune responses can include anaphylaxis, allergic rhinitis, asthma, skin sensitivity such as urticaria, eczema, and allergic contact dermatitis and ocular allergies such as allergic conjunctivitis and contact allergy. Patients identified as having allergies includes patients having one or more of the above noted conditions.

Blood samples were taken from patients who were diagnosed with osteoarthritis and allergies as defined herein. These patients are classified as presenting with co-morbidity, or multiple disease states. Gene expression profiles were then analysed and compared to profiles from patients unaffected by any disease. In each case, the diagnosis of osteoarthritis and allergies was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with osteoarthritis and allergies as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 10 shows a diagrammatic representation of gene expression profiles of blood samples from individuals who were identified as having allergies as described herein as compared with gene expression profiles from normal individuals. Expression profiles were generated using GeneSpring™ software analysis as described herein. Each column represents the hybridization pattern resulting from a single individual. In this example, patients with allergies also presented with OA, as described herein. Normal individuals had no known medical conditions and were not taking any known medication. Hybridizations to create said gene expression profiles were done using the ChondroChip™. A dendograrn analysis is shown above. Samples are clustered and marked as representing patients who are obese or normal. The "*" indicates those patients who abnormally clustered as either having allergies or being normal despite presenting with the reverse. The number of hybridizations profiles determined for patients with allergies and normal individuals are shown. 633 genes were identified as being differentially expressed with a p value of <0.05 as between patients with allergies and normal individuals is noted. The identity of the differentially expressed genes is shown in Table 3C.

Classification or class prediction of a test sample as either having allergies and OA or being normal can be done using the differentially expressed genes as shown in Table 3C in combination with well known statistical algorithms as would be understood by a person skilled in the art and described herein. Commercially available programs such as those provided by Silicon Genetics (e.g. GeneSpring™) for Class Predication are also available.

EXAMPLE 12A

ChondroChip™ Microarray Data Analysis of gene expression profiles of blood samples from individuals having osteoarthritis (OA) and allergies as compared with gene expression profiles from individuals with OA only.

This example demonstrates the use of the claimed invention to detect differential gene expression in blood samples taken from patients with allergies and OA as compared to blood samples taken from OA patients.

Blood samples were taken from patients who were diagnosed with osteoarthritis and allergies as defined herein. Gene expression profiles were then analysed and compared to profiles from patients affected by OA only. In each case, the diagnosis of osteoarthritis and allergies was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with osteoarthritis and allergies as compared to OA patients only was determined by statistical analysis using the Wilcox Mann Whitney rank sum test (Glantz S A., Primer of Biostatistics., 5th ed., New York, USA: McGraw-Hill Medical Publishing Division, 2002).

Expression profiles were generated using GeneSpring™ software analysis as described herein (data not shown). 498 genes were identified as being differentially expressed with a p value of <0.05 as between patients with allergies and OA as compared with patients with OA only. Of the 498 genes identified, those genes previously identified in Table 3C were removed so as to identify those genes which are unique to allergies. 257 differentially expressed genes were identified as being as unique to allergies. The identity of these differentially expressed genes is shown in Table 3T. A gene list is also provided of the 241 genes which were found in common as between those genes identified in Table 3C and genes differentially expressed in blood samples taken from patients with osteoarthritis and allergies as compared to blood samples taken from OA patients only. The identity of these intersecting differentially expressed genes is shown in Table 3U and a venn diagram showing the relationship between the various groups of gene lists is found in FIG. 31.

Classification or class prediction of a test sample as having allergies or not having allergies can be done using the differentially expressed genes as shown in Table 3T as the predictor genes in combination with well known statistical algorithms as would be understood by a person skilled in the art and described herein. Commercially available programs such as those provided by Silicon Genetics (e.g. GeneSpring™) for Class Predication are also available. Classification of individuals as having both OA and allergies using the genes in Table 3U can also be performed.

EXAMPLE 13

ChondroChip™ Microarray Data Analysis of gene expression profiles of blood samples from co-morbid individuals having osteoarthritis and subject to systemic steroids as compared with gene expression profiles from normal individuals This example demonstrates the use of the claimed invention to detect differential gene expression in blood samples taken from patients subject to systemic steroids as compared to blood samples taken from healthy patients.

As used herein, "systemic steroids" indicates a person subjected to artificial levels of steroids as a result of medical intervention. Such systemic steroids include birth control pills, prednisone, and hormones as a result of hormone replacement treatment. A person identified as having systemic steroids is one who is on one or more of the following of the above treatment regimes.

Blood samples were taken from patients who were diagnosed with osteoarthritis and subject to systemic steroids as defined herein. Gene expression profiles were then analysed and compared to profiles from patients unaffected by any disease. In each case, the diagnosis of osteoarthritis and systemic steroids was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to the 15K Chondrogene Microarray Chip (ChondroChip™) as described herein. Identification of genes differentially expressed in blood samples from patients with osteoarthritis and subject to systemic steroids as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 11 shows a diagrammatic representation of gene expression profiles of blood samples from individuals who were subject to systemic steroids as described herein as compared with gene expression profiles from normal individuals. Expression profiles were generated using GeneSpring™ software analysis as described herein. Each column represents the hybridization pattern resulting from a single individual. In this example, patients taking systemic steroids also presented with OA, as described herein. Normal individuals have no known medical conditions and were not taking any known medication. Hybridizations to create said gene expression profiles were done using the ChondroChip™. (A dendogram analysis is shown above. Samples are clustered and marked as representing patients who are taking systemic steroids or normal. The "*" indicates those patients who abnormally clustered as either systemic steroids or normal despite presenting with the reverse. The number of hybridizations profiles determined for patients with systemic steroids and normal individuals are shown. 605 genes were identified as being differentially expressed with a p value of <0.05 as between patients with systemic steroids and normal individuals is noted. The identity of the differentially expressed genes is shown in Table 3D.

Classification or class prediction of a test sample from a patient as indicating said patient takes systemic steroids and has OA or as being normal can be done using the differentially expressed genes as shown in Table 3A in combination with well known statistical algorithms for class prediction as would be understood by a person skilled in the art and is described herein. Commercially available programs such as those provided by Silicon Genetics (e.g. GeneSpring™) for Class Predication are also available.

EXAMPLE 13A

ChondroChip™ Microarray Data Analysis of gene expression profiles of blood samples from co-morbid individuals having osteoarthritis and subject to systemic steroids as compared with gene expression profiles from with osteoarthritis only.

This example demonstrates the use of the claimed invention to detect differential gene expression in blood samples taken from patients subject to systemic steroids and having OA as compared to blood samples taken from OA patients only.

Blood samples were taken from patients who were diagnosed with osteoarthritis and subject to systemic steroids as defined herein. Gene expression profiles were then analysed and compared to profiles from patients having OA only. In each case, the diagnosis of osteoarthritis and systemic steroids was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to the 15K Chondrogene Microarray Chip (ChondroChip™) as described herein. Identification of genes differentially expressed in blood samples from patients with osteoarthritis and subject to systemic steroids as compared patients with OA only was determined by statistical analysis using the Wilcox Mann Whitney rank sum test (Glantz S A., Primer of Biostatistics., 5th ed., New York, USA: McGraw-Hill Medical Publishing Division, 2002).

Expression profiles were generated using GeneSpring™ software analysis as described herein (data not shown). 553 genes were identified as being differentially expressed with a p value of <0.05 as between patients taking systemic steroids and OA as compared with patients with OA only. Of the 553 genes identified, those genes previously identified in Table 3D were removed so as to identify those genes which are unique to systemic steroids. 362 differentially expressed genes were identified as being as unique to systemic steroids. The identity of these differentially expressed genes are shown in Table 3V. A gene list is also provided of the 191 genes which were found in common as between those genes identified in Table 3D and genes differentially expressed in blood samples taken from patients with osteoarthritis and systemic steroids as compared to blood samples taken from OA patients only. The identity of these intersecting differentially expressed genes is shown in Table 3W and a venn diagram showing the relationship between the various groups of gene lists is found in FIG. 32.

Classification or class prediction of a test sample of an individual as either taking systemic steroids or not taking systemic steroids can be done using the differentially expressed genes as shown in Table 3V as the predictor genes in combination with well known statistical algorithms as would be understood by a person skilled in the art and described herein. Commercially available programs such as those provided by Silicon Genetics (e.g. GeneSpring™) for Class Predication are also available. Classification of individuals as having both OA and taking systemic steroids using the genes in Table 3W can also be performed.

EXAMPLE 13B

ChondroChip™ Microarray Data Analysis of gene expression profiles of blood samples from co-morbid individuals having osteoarthritis and subject to systemic steroids as compared with gene expression profiles from normal individuals.

This example demonstrates the use of the claimed invention to detect differential gene expression in blood samples taken from patients subject to various specific systemic steroids as compared to blood samples taken from healthy patients, and the ability to categorize and differentiate as between the systemic steroid being taken.

As used herein, "systemic steroids" indicates a person subjected to artificial levels of steroids as a result of medical intervention. Such systemic steroids include birth control pills, prednisone, and hormones as a result of hormone replacement treatment. A person identified as having systemic steroids is one who is on one or more of the following of the above treatment regimes.

Blood samples were taken from patients who were diagnosed with osteoarthritis and subject to systemic steroids as defined herein. Gene expression profiles were then analysed and compared as between the systemic steroids as compared to profiles from patients unaffected by any disease. In each case, the diagnosis of osteoarthritis and systemic steroids was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to the 15K Chondrogene Microarray Chip (ChondroChip™) as described herein. Identification of genes differentially expressed in blood samples from patients with osteoarthritis and subject to systemic steroids as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 34 shows a diagrammatic representation of gene expression profiles of blood samples from individuals who were subject to either birth control, prednisone, or hormone replacement therapy as described herein as compared with gene expression profiles from normal individuals. Expression profiles were generated using GeneSpring™ software analysis as described herein. Each column represents the hybridization pattern resulting from a single individual. In this example, patients taking with each of the systemic steroids also presented with OA, as described herein. Normal individuals have no known medical conditions and were not taking any known medication. Hybridizations to create said gene expression profiles were done using the ChondroChip™. A dendogram analysis is shown above. Samples are clustered and marked as representing patients who are taking birth control, prednisone, hormone replacement therapy or normal. The "*" indicates those patients who abnormally clustered. The number of hybridizations profiles determined for patients with birth control, prednisone, hormone replacement therapy or normal individuals are shown. 396 genes were identified as being differentially expressed with a p value of <0.05 as between patients with systemic steroids and normal individuals is noted. The identity of the differentially expressed genes is shown in Table 3AD.

Classification or class prediction of a test sample from a patient as indicating said patient takes systemic steroids and has OA or as being normal can be done using the differentially expressed genes as shown in Table 3AD in combination with well known statistical algorithms for class prediction as would be understood by a person skilled in the art and is described herein. Commercially available programs such as those provided by Silicon Genetics (e.g. GeneSpring™) for Class Predication are also available.

EXAMPLE 14

ChondroChip™ Microarray Data Analysis of gene expression profiles of blood samples from individuals having hypertension as compared with gene expression profiles from normal individuals.

This example demonstrates the use of the claimed invention to detect differential gene expression in blood samples taken from patients with hypertension but without osteoarthritis as compared to blood samples taken from healthy patients.

As used herein, the term "hypertension" is defined as high blood pressure or elevated arterial pressure. Patients identified with hypertension herein include persons who have an increased risk of developing a morbid cardiovascular event and/or persons who benefit from medical therapy designed to treat hypertension. Patients identified with hypertension also can include persons having systolic blood pressure of >130 mm Hg or a diastolic blood pressure of >90 mm Hg or a person takes antihypertensive medication.

Blood samples were taken from patients who were diagnosed with hypertension as defined herein. Gene expression profiles were then analysed and compared to profiles from patients unaffected by any disease. In each case, the diagnosis of hypertension was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with hypertension as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 12 shows a diagrammatic representation of gene expression profiles of blood samples from individuals having hypertension as compared with gene expression profiles from samples of both non-hypertensive and normal individuals. Expression profiles were generated using GeneSpring™ software analysis as described herein. Each column represents the hybridization pattern resulting from a single individual. Non-hypertensive individuals presented without hypertension, but may have presented with other medical conditions and may be under various treatment regimes. Normal individuals have no known medical conditions and were not taking any known medication. Hybridizations to create said gene expression profiles were done using the ChondroChip™. A dendogram analysis is shown above. Samples are clustered and marked as representing patients who are hypertensive, normal or non-hypertensive. The "*" indicates those patients who abnormally clustered as either hypertensive, non-hypertensive or normal despite actual presentation. The number of hybridizations profiles determined for hypertensive patients, non-hypertensive patients and normal individuals are shown. 1,993 genes identified as being differentially expressed with a p value of <0.05 as between the hypertensive patients and the combined normal and non-hypertensive individuals is noted. The identity of the differentially expressed genes are shown in Table 3E.

Classification or class prediction of a test sample of an individual so as to determine whether said individual has or does not have hypertension can be done using the differentially expressed genes as shown in Table 3E as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 15

ChondroChip™ Microarray Data Analysis of gene expression profiles of blood samples from individuals having obesity as compared with gene expression profiles from normal individuals.

This example demonstrates the use of the claimed invention to detect differential gene expression in blood samples taken from patients with obesity but without osteoarthritis as compared to blood samples taken from healthy patients.

As used herein, "obesity" is defined as an excess of adipose tissue that imparts a health risk. Obesity is assessed in terms of height and weight in the relevance of age. Patients who are considered obese include, but are not limited to, patients having a body mass index or BMI ((defined as body weight in kg divided by (height in meters)$^2$) greater than or equal to 30.0.

Blood samples were taken from patients who were diagnosed with hypertension as defined herein. Gene expression profiles were then analysed and compared to profiles from patients unaffected by any disease. In each case, the diagnosis of obesity was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a (ChondroChip™) as described herein. Identification of genes differentially expressed in blood samples from patients with obesity as compared to healthy patients was determined by statistical analysis using the Wilcox Mann Whitney rank sum test (Glantz SA., Primer of Biostatistics, 5th ed., New York, USA: McGraw-Hill Medical Publishing Division, 2002).

FIG. 13 shows a diagrammatic representation of gene expression profiles of blood samples from individuals who were identified as obese as described herein as compared with gene expression profiles from normal and non-obese individuals. Expression profiles were generated using GeneSpring™ software analysis as described herein. Each column represents the hybridization pattern resulting from a single individual. Normal individuals have no known medical conditions and were not taking any known medication. Non-obese individuals presented without obesity, but may have presented with other medical conditions and may be under various treatment regimes. Hybridizations to create said gene expression profiles were done using the ChondroChip™. A dendogram analysis is shown above. Samples are clustered and marked as representing patients who are obese, normal or non-obese. The "*" indicates those patients who abnormally clustered as either obese, normal or non-obese despite actual presentation. The number of hybridizations profiles determined for obese patients, non-obese patients and normal individuals are shown. 1,147 genes were identified as being differentially expressed with a p value of <0.05 as between the obese patients and the combination of normal and non-obese individuals is noted. The identity of the differentially expressed genes is shown in Table 3F.

Classification or class prediction of a test sample as being obese or not being obese can be done using the differentially expressed genes as shown in Table 3F as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 16

ChondroChip™ Microarray Data Analysis of gene expression profiles of blood samples from individuals having type 2 diabetes as compared with gene expression profiles from normal individuals.

This example demonstrates the use of the claimed invention to detect differential gene expression in blood samples taken from patients with type 2 diabetes but without osteoarthritis as compared to blood samples taken from healthy patients.

As used herein, "diabetes", or "diabetes mellitus" includes both "type 1 diabetes" (insulin-dependent diabetes (IDDM)) and "type 2 diabetes" (insulin-independent diabetes (NIDDM). Both type 1 and type 2 diabetes characterized in accordance with Harrison's Principles of Internal Medicine 14th edition, as a person having a venous plasma glucose concentration ≧140 mg/dL on at least two separate occasions after overnight fasting and venous plasma glucose concentration ≧200 mg/dL at 2 h and on at least one other occasion during the 2-h test following ingestion of 75 g of glucose. Patients identified as having type 2 diabetes as described herein are those demonstrating insulin-independent diabetes as determined by the methods described above.

Blood samples were taken from patients who were diagnosed with type II diabetes as defined herein. Gene expression profiles were then analysed and compared to profiles from patients unaffected by any disease. In each case, the diagnosis of type II diabetes was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with type 2 diabetes as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 14 shows a diagrammatic representation of gene expression profiles of blood samples from individuals who were identified as having type 2 diabetes as described herein as compared with gene expression profiles from normal and non-type 2 diabetes individuals. Expression profiles were generated using GeneSpring™ software analysis as described herein. Each column represents the hybridization pattern resulting from a single individual. Normal individuals have no known medical conditions and were not taking any known medication. Non-type 2 diabetes individuals presented without type 2 diabetes, but may have presented with other medical conditions and may be under various treatment regimes. Hybridizations to create said gene expression profiles were done using the ChondroChip™. A dendogram analysis is shown above. Samples are clustered and marked as representing patients who have type 2 diabetes, are normal or do not have type 2 diabetes. The "*" indicates those patients who abnormally clustered despite actual presentation. The number of hybridizations profiles determined for type 2 diabetes, non-type 2 diabetes and normal individuals are shown. 915 were identified as being differentially expressed with a p value of <0.05 as between the type 2 diabetes patients and the combination of normal and non type 2 diabetes individuals is noted. The identity of the differentially expressed genes is shown in Table 3G.

Classification or class prediction of a test sample of an individual so as to determine whether said individual has type 2 diabetes or does not have type 2 diabetes can be done using the differentially expressed genes as shown in Table 3G as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 17

ChondroChip™ Microarray Data Analysis of gene expression profiles of blood samples from individuals having hyperlipidemia as compared with gene expression profiles from normal individuals.

This example demonstrates the use of the claimed invention to detect differential gene expression in blood samples taken from patients with hyperlipidemia but without osteoarthritis as compared to blood samples taken from healthy patients.

As used herein, "hyperlipidemia" is defined as an elevation of lipid protein profiles and includes the elevation of chylomicrons, very low-density lipoproteins (VLDL), intermediate-density lipoproteins (IDL), low-density lipoproteins (LDL), and/or high-density lipoproteins (HDL) as compared with the general population. Hyperlipidemia includes hypercholesterolemia and/or hypertriglyceridemia. By hypercholesterolemia, it is meant elevated fasting plasma total cholesterol level of >200 mg/dL, and/or LDL-cholesterol levels of >130 mg/dL. A desirable level of HDL-cholesterol is >60 mg/dL. By hypertriglyceridemia it is meant plasma triglyceride (TG) concentrations of greater than the $90^{th}$ or $95^{th}$ percentile for age and sex and can include, for example, TG>160 mg/dL as determined after an overnight fast.

Blood samples were taken from patients who were diagnosed with hyperlipidemia as defined herein. Gene expression profiles were then analysed and compared to profiles from patients unaffected by any disease. In each case, the diagnosis of hyperlipidemia was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with hyperlipidemia as compared to healthy patients was determined by statistical analysis using the Wilcox Mann Whitney rank sum test (Glantz S A., Primer of Biostatistics, 5th ed., New York, USA: McGraw-Hill Medical Publishing Division, 2002).

FIG. 15 shows a diagrammatic representation of gene expression profiles of blood samples from individuals who were identified as having hyperlipidemia as described herein as compared with gene expression profiles from normal and non-hyperlipidemia patients. Expression profiles were generated using GeneSpring™ software analysis as described herein. Each column represents the hybridization pattern resulting from a single individual. Normal individuals have no known medical conditions and were not taking any known medication. Non hyperlipidemia individuals presented without elevated cholesterol or elevated triglycerides but may have presented with other medical conditions and may be under various treatment regimes. Hybridizations to create said gene expression profiles were done using the ChondroChip™. A dendogram analysis is shown above. Samples are clustered and marked as representing patients who have elevated lipids and/or cholesterol, are normal or do not have elevated lipids or cholesterol. The "*" indicates those patients who abnormally clustered as having either hyperlipidemia, normal or non-hyperlipidemia despite actual presentation. The number of hybridizations profiles determined for hyperlipidemia patients, non-hyperlipidemia patients and normal individuals are shown. 1,022 genes were identified as being differentially expressed with a p value of <0.05 as between the patients with hyperlipidemia and the combination of normal and non hyperlipidemia individuals. The identity of the differentially expressed genes is shown in Table 3H.

Classification or class prediction of a test sample of an individual as having hyperlipidemia or not having hyperlipidemia can be done using the differentially expressed genes as shown in Table 3H as the predictor genes in combination with well known statistical algorithms as would be understood by a person skilled in the art and described herein. Commercially available programs such as those provided by Silicon Genetics for Class Predication (e.g. GeneSpring™) are also available.

EXAMPLE 18

ChondroChip™ Microarray Data Analysis of gene expression profiles of blood samples from individuals having lung disease as compared with gene expression profiles from normal individuals.

This example demonstrates the use of the claimed invention to detect differential gene expression in blood samples taken from patients with lung disease but without osteoarthritis as compared to blood samples taken from healthy patients.

As used herein, "lung disease" encompasses any disease that affects the respiratory system and includes bronchitis, chronic obstructive lung disease, emphysema, asthma, and lung cancer. Patients identified as having lung disease includes patients having one or more of the above noted conditions.

Blood samples were taken from patients who were diagnosed with lung disease as defined herein. Gene expression profiles were then analysed and compared to profiles from patients unaffected by any disease. In each case, the diagnosis of lung disease was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with lung disease as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 16 shows a diagrammatic representation of gene expression profiles of blood samples from individuals who were identified as having lung disease as described herein as compared with gene expression profiles from normal and non lung disease individuals. Expression profiles were generated using GeneSpring™ software analysis as described herein. Each column represents the hybridization pattern resulting from a single individual. Normal individuals have no known medical conditions and were not taking any known medication. Non-lung disease individuals presented without lung disease, but may have presented with other medical conditions and may be under various treatment regimes. Hybridizations to create said gene expression profiles were done using the ChondroChip™. A dendogram analysis is shown above. Samples are clustered and marked as representing patients who have lung disease, are normal or do not have lung disease. The "*" indicates those patients who abnormally clustered despite actual presentation. The number of hybridizations profiles determined for either the lung disease patients, non-lung disease patients and normal individuals are show. 596 genes were identified as being differentially expressed with a p value of <0.05 as between the lung disease patients and the combination of normal and non lung disease individuals is noted. The identity of the differentially expressed genes is shown in Table 3I.

Classification or class prediction of a test sample of an individual to determine whether said individual has lung disease or does not having lung disease can be done using the differentially expressed genes as shown in Table 3I as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 19

Affymetrix U133A Chip Microarray Data Analysis of gene expression profiles of blood samples from individuals having bladder cancer as compared with gene expression profiles from normal individuals.

This example demonstrates the use of the claimed invention to detect differential gene expression in blood samples taken from patients with bladder cancer but without osteoarthritis as compared to blood samples taken from healthy patients.

As used herein, the term "cancer" or "carcinoma" is defined as a disease in which cells behave abnormally and includes; (i) cancers which originate from a single cell proliferating to form a clone of malignant cells, (ii) cancers wherein the growth of the cell is not regulated by normal biological and physical influences of the environment, (iii) anaplasic cancer, wherein the cells lack normal coordinated cell differentiation and (iv) metastasis cancer, wherein the cells have the capacity for discontinuous growth and dissemination to other parts of the body. The diagnosis of cancer can include careful clinical assessment and/or diagnostic investigations including endoscopy, imaging, histopathology, cytology and laboratory studies.

As used herein, "bladder cancer" includes carcinomas that occur in the transitional epithelium lining the urinary tract, starting at the renal pelvis and extending through the ureter, the urinary bladder, and the proximal two-thirds of the urethra. As used herein, patients diagnosed with bladder cancer include patients diagnosed utilizing any of the following methods or a combination thereof: urinary cytologic evaluation, endoscopic evaluation for the presence of malignant cells, CT (computed tomography), MRI (magnetic resonance imaging) for metastasis status.

Blood samples were taken from patients who were diagnosed with bladder cancer as defined herein. Gene expression profiles were then analysed and compared to profiles from patients unaffected by any disease. In each case, the diagnosis of bladder cancer was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with bladder cancer as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 17 shows a diagrammatic representation of gene expression profiles of blood samples from individuals who were identified as having bladder cancer as described herein as compared with gene expression profiles from non bladder cancer individuals. Expression profiles were generated using GeneSpring™ software analysis as described herein. Each column represents the hybridization pattern resulting from a single individual. Non bladder cancer individuals presented without bladder cancer, but may have presented with other medical conditions and may be under various treatment regimes. Hybridizations to create said gene expression profiles were done using the Affymetrix U133A chip. A dendogram analysis is shown above. Samples are clustered and marked as representing patients who have bladder cancer, or do not have bladder cancer. The "*" indicates those patients who abnormally clustered as either bladder cancer, or non bladder cancer despite actual presentation. The number of hybridizations profiles determined for patients with bladder cancer and without bladder cancer are shown. 4,228 genes were identified as being differentially expressed with a p value of <0.05 as between the bladder cancer patients and the non bladder cancer individuals is noted. The identity of the differentially expressed genes is shown in Table 3J.

Classification or class prediction of a test sample of an individual to determine whether said individual has bladder cancer or does not having bladder cancer can be done using the differentially expressed genes as shown in Table 3J as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 20

Affymetrix U133A Chip Microarray Data Analysis of gene expression profiles of blood samples from individuals having early or advanced bladder cancer as compared with gene expression profiles from normal individuals.

This example demonstrates the use of the claimed invention to detect differential gene expression in blood samples taken from patients with early or advanced late stage bladder cancer but without osteoarthritis as compared to blood samples taken from healthy patients.

As used herein, "early stage bladder cancer" includes bladder cancer wherein the detection of the anatomic extent of the tumour, both in its primary location and in metastatic sites, as defined by the TNM staging system in accordance with Harrison's Principles of Internal Medicine 14th edition can be considered early stage. More specifically, early stage bladder cancer can include those instances wherein the carcinoma is mainly superficial.

As used herein, "advanced stage bladder cancer" is defined as bladder cancer wherein the detection of the anatomic extent of the tumour, both in its primary location and in metastatic sites, as defined by the TNM staging system in accordance with Harrison's Principles of Internal Medicine 14th edition, can be considered as advanced stage. More specifically, advanced stage carcinomas can involve instances wherein the cancer has infiltrated the muscle and wherein metastasis has occurred.

Blood samples were taken from patients who were diagnosed with early or advanced late stage bladder cancer as defined herein. Gene expression profiles were then analysed and compared to profiles from patients unaffected by any disease. In each case, the diagnosis of early or advanced late stage bladder cancer was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with early or advanced late stage bladder cancer as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 18 shows a diagrammatic representation of gene expression profiles of blood samples from individuals who were identified as having advanced stage bladder cancer or early stage bladder cancer as described herein as compared with gene expression profiles from non bladder cancer individuals. Expression profiles were generated using GeneSpring™ software analysis as described herein. Each column represents the hybridization pattern resulting from a single individual. Non bladder cancer individuals presented without bladder cancer, but may have presented with other medical conditions and may be under various treatment regimes. Hybridizations to create said gene expression profiles were done using the Affymetrix U1338 chip. A dendogram analysis is shown above. Samples are clustered and marked as representing patients who have early stage bladder cancer, advanced stage bladder cancer, or do not have bladder cancer. The "*" indicates those patients who abnormally clustered despite actual presentation. The number of hybridizations profiles determined for either early stage bladder cancer, advanced bladder cancer or non-bladder cancer are shown. 3,518 genes were identified as being differentially expressed with a p value of <0.05 as between the bladder cancer patients and the non bladder cancer individuals is noted. The identity of the differentially expressed genes is shown in Table 3K.

Classification or class prediction of a test sample of an individual to determine whether said individual has advanced bladder cancer, early stage bladder cancer or does not have bladder cancer can be done using the differentially expressed genes as shown in Table 3K as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 21

Affymetrix U133A Chip Microarray Data Analysis of gene expression profiles of blood samples from individuals having coronary artery disease as compared with gene expression profiles from normal individuals.

This example demonstrates the use of the claimed invention to detect differential gene expression in blood samples taken from patients with coronary artery disease but without osteoarthritis as compared to blood samples taken from healthy patients As used herein, "Coronary artery disease" (CAD) is defined as a condition wherein at least one coronary artery has >50% luminal diameter stenosis, as diagnosed by coronary angiography and includes conditions in which there is atheromatous narrowing and subsequent occlusion of the vessel. CAD includes those conditions which manifest as angina, silent ischaemia, unstable angina, myocardial infarction, arrhythmias, heart failure, and sudden death. Patients identified as having CAD herein Coronary artery disease is defined Blood samples were taken from patients who were diagnosed with Coronary artery disease as defined herein. Gene expression profiles were then analysed and compared to profiles from patients unaffected by any disease. In each case, the diagnosis of Coronary artery disease was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with Coronary artery disease as compared to healthy patients was determined by statistical analysis using the Wilcox Mann Whitney rank sum test (Glantz S A., Primer of Biostatistics, 5th ed., New York, USA, McGraw-Hill Medical Publishing Division, 2002).

FIG. 19 shows a diagrammatic representation of gene expression profiles of blood samples from individuals who were identified as having coronary artery disease (CAD) as described herein as compared with gene expression profiles from non-coronary artery disease individuals. Expression profiles were generated using GeneSpring™ software analysis as described herein. Each column represents the hybridization pattern resulting from a single individual. Non coronary artery disease individuals presented without coronary artery disease, but may have presented with other medical conditions and may be under various treatment regimes. Hybridizations to create said gene expression profiles were done using the Affymetrix™ U133A chip. A dendogram analysis is shown above. Samples are clustered and marked as representing patients who have coronary artery disease or do not have coronary artery disease. The "*" indicates those patients who abnormally clustered despite actual presentation. The number of hybridizations profiles determined for patients with CAD or without CAD are shown. 967 genes were identified as being differentially expressed with a p value of <0.05 as between the coronary artery disease patients and those individuals without coronary artery disease is noted. The identity of the differentially expressed genes is shown in Table 3L.

Classification or class prediction of a test sample of an individual to determine whether said individual has CAD or does not have CAD can be done using the differentially expressed genes as shown in Table 3L as the predictor genes in combination with well known statistical algorithms as would be understood by a person skilled in the art and described herein. Commercially available programs such as those provided by Silicon Genetics for Class Predication (e.g. GeneSpring™) are also available.

EXAMPLE 22

Affymetrix U133A Chip Microarray Data Analysis of gene expression profiles of blood samples from individuals having Rheumatoid arthritis as compared with gene expression profiles from normal individuals.

This example demonstrates the use of the claimed invention to detect differential gene expression in blood samples taken from patients with Rheumatoid arthritis but without osteoarthritis as compared to blood samples taken from healthy patients.

Rheumatoid arthritis (RA) is defined as a chronic, multi-system disease of unknown etiology with the characteristic feature of persistent inflammatory synovitis. Said inflammatory synovitis usually involves peripheral joints in a systemic distribution. Patients having RA as defined herein were identified as having one or more of the following; (i) cartilage destruction, (ii) bone erosions, and/or (iii) joint deformities.

Blood samples were taken from patients who were diagnosed Rheumatoid arthritis as defined herein. Gene expression profiles were then analysed and compared to profiles from patients unaffected by any disease. In each case, the diagnosis of Rheumatoid arthritis was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with Rheumatoid arthritis as compared to healthy patients was determined by statistical analysis using the Wilcox Mann Whitney rank sum test (Glantz S A., Primer of Biostatistics., 5th ed., New York, USA: McGraw-Hill Medical Publishing Division, 2002).

FIG. 20 shows a diagrammatic representation of gene expression profiles of blood samples from individuals who were identified as having rheumatoid arthritis as described herein as compared with gene expression profiles from non-rheumatoid arthritis individuals. Expression profiles were generated using GeneSpring™ software analysis as described herein. Each column represents the hybridization pattern resulting from a single individual. Normal individuals have no known medical conditions and were not taking any known medication. Non rheumatoid arthritis individuals presented without rheumatoid arthritis, but may have presented with other medical conditions and may be under various treatment regimes. Hybridizations to create said gene expression profiles were done using ChondroChip™. A dendogram analysis is shown above. Samples are clustered and marked as representing patients who have rheumatoid arthritis or do not have rheumatoid arthritis. The "*" indicates those patients who abnormally clustered despite actual presentation. The number of hybridizations profiles determined for patients with rheumatoid arthritis and without rheumatoid arthritis are shown. 2,068 genes were identified as being differentially expressed with a p value of <0.05 as between the rheumatoid arthritis patients and a combination of those individuals without rheumatoid arthritis and normal is noted. The identity of the differentially expressed genes is shown in Table 3M.

Classification or class prediction of a test sample of an individual as having rheumatoid arthritis or not having rheumatoid arthritis can be done using the differentially expressed genes as shown in Table 3M as the predictor genes in combination with well known statistical algorithms as would be understood by a person skilled in the art and described herein. Commercially available programs such as those provided by Silicon Genetics for Class Predication (e.g. GeneSpring™) are also available.

EXAMPLE 23

Affymetrix U133A Chip Microarray Data Analysis of gene expression profiles of blood samples from individuals having depression as compared with gene expression profiles from normal individuals.

This example demonstrates the use of the claimed invention to detect differential gene expression in blood samples taken from patients with depression but without osteoarthritis as compared to blood samples taken from healthy patients As used herein "mood disorders" are conditions characterized by a disturbance in the regulation of mood, behavior, and affect. "Mood disorders" can include depression, anxiety, schizophrenia, bipolar disorder, manic depression and the like.

As used herein "depression" includes depressive disorders or depression in association with medical illness or substance abuse in addition to depression as a result of sociological situations. Patients defined as having depression were diagnosed mainly on the basis of clinical symptoms including a depressed mood episode wherein a person displays a depressed mood on a daily basis for a period of greater than 2 weeks. A depressed mood episode may be characterized by sadness, indifference, apathy, or irritability and is usually associated with changes in a number of neurovegetative functions, including sleep patterns, appetite and weight, fatigue, impairment in concentration and decision making.

Blood samples were taken from patients who were diagnosed with depression as defined herein. Gene expression profiles were then analysed and compared to profiles from patients unaffected by any disease. In each case, the diagnosis of depression was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with depression as compared to healthy patients was determined by statistical analysis using the Wilcox Mann Whitney rank sum test (Glantz S A., Primer of Biostatistics, 5th ed., New York, USA: McGraw-Hill Medical Publishing Division, 2002).

FIG. 21 shows a diagrammatic representation of gene expression profiles of blood samples from individuals who were identified as having depression as described herein as compared with gene expression profiles from non-depression individuals. Expression profiles were generated using GeneSpring™ software analysis as described herein. Each column represents the hybridization pattern resulting from a single individual. Normal individuals have no known medical conditions and were not taking any known medication. Non depression individuals presented without depression, but may have presented with other medical conditions and may be under various treatment regimes. Hybridizations to create said gene expression profiles were done using Chondro-Chip™. A dendogram analysis is shown above. Samples are clustered and marked as representing patients who have depression, having non-depression or normal. The "*" indicates those patients who abnormally clustered despite actual presentation. The number of hybridizations profiles determined for patients with depression, non-depression and normal are shown. 941 genes were identified as being differentially expressed with a p value of <0.05 as between the patients with depression and a combination of those individuals without depression and normal is noted. The identity of the differentially expressed genes is shown in Table 3N.

Classification or class prediction of a test sample of an individual to determine whether said individuals has depression or does not having depression can be done using the differentially expressed genes as shown in Table 3N as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 24

ChondroChip™ Microarray Data Analysis of gene expression profiles of blood samples from individuals having osteoarthritis as compared with gene expression profiles from normal individuals.

This example demonstrates the use of the claimed invention to detect differential gene expression in blood samples taken from patients who were identified as having various stages of osteoarthritis as compared to blood samples taken from healthy patients.

Osteoarthritis (OA), as used herein also known as "degenerative joint disease", represents failure of a diarthrodial (movable, synovial-lined) joint. It is a condition, which affects joint cartilage, and or subsequently underlying bone and supporting tissues leading to pain, stiffness, movement problems and activity limitations. It most often affects the hip, knee, foot, and hand, but can affect other joints as well.

OA severity can be graded according to the system described by Marshall (Marshall, K. W., J. Rheumatol., 1996, 23(4):582-85). Briefly, each of the six knee articular surfaces was assigned a cartilage grade with points based on the worst lesion seen on each particular surface. Grade 0 is normal (0 points), Grade I cartilage is soft or swollen but the articular surface is intact (1 point). In Grade II lesions, the cartilage surface is not intact but the lesion does not extend down to subchondral bone (2 points). Grade III damage extends to subchondral bone but the bone is neither eroded nor eburnated (3 points). In Grade IV lesions, there is eburnation of or erosion into bone (4 points). A global OA score is calculated by summing the points from all six cartilage surfaces. If there is any associated pathology, such as meniscus tear, an extra point will be added to the global score. Based on the total score, each patient is then categorized into one of four OA groups: mild (1-6), moderate (7-12), marked (13-18), and severe (>18). As used herein, patients identified with OA may be categorized in any of the four OA groupings as described above.

Blood samples were taken from patients who were diagnosed with osteoarthritis and a specific stage of osteoarthritis as defined herein. Gene expression profiles were then analysed and compared to profiles from patients unaffected by any disease. In each case, the diagnosis of osteoarthritis and the stage of osteoarthritis was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a 15K Chondrogene Microarray Chip (ChondroChip™) as described herein. Identification of genes differentially expressed in blood samples from patients with disease as compared to healthy patients was determined by statistical analysis using the Wilcox Mann Whitney rank sum test (Glantz S A., Primer of Biostatistics, 5th ed., New York, USA: McGraw-Hill Medical Publishing Division, 2002).

FIG. 22 shows a diagrammatic representation of gene expression profiles of blood samples from individuals having osteoarthritis as compared with gene expression profiles from normal individuals. Expression profiles were generated using GeneSpring™ software analysis as described herein. Each column represents the hybridization pattern resulting from a single individual. Normal individuals have no known medical conditions and were not taking any known medication. Hybridizations to create said gene expression profiles were done using the ChondroChip™. A dendogram analysis is shown above. Samples are clustered and marked as representing patients who presented with different stages of osteoarthritis or normal. The "*" indicates those patients who abnormally clustered despite actual presentation. The number of hybridizations profiles determined for either osteoarthritis patients or normal individuals are shown. 300 differentially expressed genes were identified as being differentially expressed with a p value of <0.05 as between the osteoarthritis patients and normal individuals. The identity of the differentially expressed genes is shown in Table 3O.

Classification or class prediction of a test sample of an individual as having OA, having mild OA, having marked OA, having moderate OA, having severe OA or not having OA can be done using the differentially expressed genes as shown in Table 3O as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 25

Microarray Data Analysis of gene expression profiles of blood samples from individuals having a condition as compared with gene expression profiles from individuals not having said condition, and wherein said individual is undergoing therapeutic treatment in light of said condition.

This example demonstrates the use of the claimed invention to detect differential gene expression in blood samples taken from individuals undergoing therapeutic treatment of a condition as compared with gene expression profiles from individuals not undergoing treatment.

Blood samples are taken from patients who are undergoing therapeutic treatment. Gene expression profiles are then analysed and compared to profiles from patients not undergoing treatment.

Total mRNA from a drop of peripheral whole blood taken from each patient is isolated using TRIzol® reagent (GIBCO) and fluorescently labelled probes for each blood sample are generated as described above. Each probe is denatured and hybridized to a microarray for example the 15K Chondrogene Microarray Chip (ChondroChip™), Affymetrix Genechip or Blood chip as described herein. Identification of genes differentially expressed in blood samples from patients undergoing therapeutic treatment as compared to patients not undergoing treatment is determined by statistical analysis using the Wilcox Mann Whitney rank sum test (Glantz S A., Primer of Biostatistics. 5th ed., New York, USA: McGraw-Hill Medical Publishing Division, 2002). Expression profiles are generated using GeneSpring™ software analysis as described herein. The number of differentially expressed genes are then identified as being differentially expressed with a p value of <0.05.

EXAMPLE 26

Affymetrix U133A Chip Microarray Data Analysis of gene expression profiles of blood samples from individuals having liver cancer as compared with gene expression profiles from normal individuals.

This example demonstrates the use of the claimed invention to detect differential gene expression in blood samples taken from patients with liver cancer as compared to blood samples taken from healthy patients.

As used herein, "liver cancer" means primary liver cancer wherein the cancer initiates in the liver. Primary liver cancer includes both hepatomas or hepatocellular carcinomas (HCC) which start in the liver and chonalgiomas where cancers develop in the bile ducts of the liver.

Blood samples were taken from patients who were diagnosed with liver cancer as defined herein. Gene expression profiles were then analysed and compared to profiles from patients unaffected by any disease. In each case, the diagnosis of liver cancer was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with liver cancer as compared to healthy patients was determined by statistical analysis using the Weltch t-Test.

FIG. 25 shows a diagrammatic representation of gene expression profiles of blood samples from individuals who were identified as having liver cancer as described herein as compared with gene expression profiles from non-liver cancer disease individuals. Expression profiles were generated using GeneSpring™ software analysis as described herein. Each column represents the hybridization pattern resulting from a single individual. Control samples presented without liver cancer but may have presented with other medical conditions and may be under various treatment regimes.

Hybridizations to create said gene expression profiles were done using the Affymetrix™ U133A chip. A dendogram analysis is shown above. Samples are clustered and marked as representing patients who have liver cancer or control. The number of hybridizations profiles determined for patients with liver cancer or who are controls are shown. 1,475 genes were identified as being differentially expressed with a p value of <0.05 as between the liver cancer patients and those control individuals. The identity of the differentially expressed genes is shown in Table 3X.

Classification or class prediction of a test sample of an individual to determine whether said individual has liver cancer or does not have liver cancer can be done using the differentially expressed genes as shown in Table 3X as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 27

Affymetrix U133A Chip Microarray Data Analysis of gene expression profiles of blood samples from individuals having schizophrenia as compared with gene expression profiles from normal individuals.

This example demonstrates the use of the claimed invention to detect differential gene expression in blood samples taken from patients with schizophrenia as compared to blood samples taken from healthy patients.

As used herein, "schizophrenia" is defined as a psychotic disorders characterized by distortions of reality and disturbances of thought and language and withdrawal from social contact. Patients diagnosed with "schizophrenia" can include patients having any of the following diagnosis: an acute schizophrenic episode, borderline schizophrenia, catatonia, catatonic schizophrenia, catatonic type schizophrenia, disorganized schizophrenia, disorganized type schizophrenia, hebephrenia, hebephrenic schizophrenia, latent schizophrenia, paranoic type schizophrenia, paranoid schizophrenia, paraphrenia, paraphrenic schizophrenia, psychosis, reactive schizophrenia or the like.

Blood samples were taken from patients who were diagnosed with schizophrenia as defined herein. Gene expression profiles were then analysed and compared to profiles from patients unaffected by any disease. In each case, the diagnosis of schizophrenia was corroborated by a skilled Board certified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with schizophrenia as compared to healthy patients was determined by statistical analysis using the Wilcox Mann Whitney rank sum test (Glantz S A., Primer of Biostatistics, 5th ed., New York, USA: McGraw-Hill Medical Publishing Division).

FIG. 26 shows a diagrammatic representation of gene expression profiles of blood samples from individuals who were identified as having schizophrenia as described herein as compared with gene expression profiles from non schizophrenic individuals. Expression profiles were generated using GeneSpring™ software analysis as described herein. Each column represents the hybridization pattern resulting from a single individual. Control samples presented without schizophrenia but may have presented with other medical conditions and may be under various treatment regimes. Hybridizations to create said gene expression profiles were done using the Affymetrix™ U133A chip. A dendogram analysis is shown above. Samples are clustered and marked as representing patients who have schizophrenia or control individuals. The number of hybridizations profiles determined for patients with liver cancer or who are controls are shown. 1,952 genes were identified as being differentially expressed with a p value of <0.05 as between the schizophrenic patients and those control individuals. The identity of the differentially expressed genes is shown in Table 3Y.

Classification or class prediction of a test sample of an individual to determine whether said individual has schizophrenia or does not having schizophrenia can be done using the differentially expressed genes as shown in Table 3Y as the predictor genes in combination with well known statistical algorithms as would be understood by a person skilled in the art and described herein. Commercially available programs such as those provided by Silicon Genetics (e.g. Gene-Spring™) for Class Predication are also available.

EXAMPLE 28

Affymetrix U133A Chip Microarray Data Analysis of gene expression profiles of blood samples from individuals having Chagas disease as compared with gene expression profiles from normal individuals.

This example demonstrates the use of the claimed invention to detect differential gene expression in blood samples taken from patients with symptomatic Chagas disease, asymptomatic Chagas disease or control individuals wherein said control individuals were confirmed as not having Chagas disease.

As used herein, "Chagas disease" is defined as a condition wherein an individual is infected with the protozoan parasite *Trypanosoma cruzi* and includes both acute and chronic infection. Acute infection with *T. cruzi* can be diagnosed by detection of parasites by either microscopic examination of fresh anticoagulated blood or the buffy coat, giemsa-stained thin and thick blood smears and/or mouse inoculation and culturing of the blood of a potentially infected individual. Even in the absence of a positive result from the above, an accurate determination of infection can be made by xenodiagnosis wherein reduviid bugs are allowed to feed on the patient's blood and subsequently the bugs are examined for infection. Chronic infection can be determined by detection of antibodies specific to the *T. cruzi* antigens and/or immunoprecipitation and electrophoresis of the *T. cruzi* antigens.

As used herein "Symptomatic Chagas disease" includes symptomatic acute chagas and symptomatic chronic chagas disease. Acute symptomatic chagas disease can be characterized by one or more of the following: area of erythema and swelling (a chagoma); local lymphadenopathy; generalized lymphadenopathy; mild hepatosplenomegaly; unilateral painless edema of the palpebrae and periocular tissues; malaise; fever; anorexia and/or edema of the face and lower extremities. Symptomatic chronic Chagas' disease includes one or more of the following symptoms: heart rhythm disturbances, cardiomyopathy, thromboembolism, electrocardiographic abnormalities including right bundle-branch blockage; atrioventricular block; premature ventricular contractions and tachy- and bradyarrhythmias; dysphagia; odynophagia, chest pain; regurgitation; weight loss, cachexia and pulmonary infections.

As used herein "Asymptomatic Chagas disease" is meant to refer to individuals who are infected with *T. cruzi* but who do not show either acute or chronic symptoms of the disease.

Blood samples were taken from patients who were diagnosed symptomatic or asymptomatic Chagas disease as defined herein. Gene expression profiles were then analysed and compared to profiles from patients unaffected by any disease. In each case, the diagnosis of Chagas disease was corroborated by a qualified physician.

Total mRNA from a drop of peripheral whole blood taken from each patient was isolated using TRIzol® reagent (GIBCO) and fluorescently labelled probes for each blood sample were generated as described above. Each probe was denatured and hybridized to an Affymetrix U133A Chip as described herein. Identification of genes differentially expressed in blood samples from patients with Chagas disease as compared to healthy patients was determined by statistical analysis using the Weltch ANOVA test (Michelson and Schofield, 1996).

FIG. 27 shows a diagrammatic representation of gene expression profiles of blood samples from individuals who were identified as having symptomatic Chagas disease; asymptomatic Chagas disease or who were control individuals as described herein. Expression profiles were generated using GeneSpring™ software analysis as described herein. Each column represents the hybridization pattern resulting from a single individual. Control samples presented without Chagas disease but may have presented with other medical conditions and may be under various treatment regimes.

Hybridizations to create said gene expression profiles were done using the Affymetrix™ U133A chip. A dendrogram analysis is shown above. Samples are clustered and marked as representing patients who have symptomatic Chagas disease; asymptomatic Chagas disease or control. The number of hybridizations profiles determined for patients with Chagas disease; asymptomatic Chagas disease or who are controls are shown. 668 genes were identified as being differentially expressed with a p value of <0.05 as between the symptomatic, asymptomatic Chagas patients and those control individuals. The identity of the differentially expressed genes is shown in Table 3Z.

Classification or class prediction of a test sample of an individual to determine whether said individual has symptomatic Chagas disease, asymptomatic Chagas disease or does not have Chagas disease can be done using the differentially expressed genes as shown in Table 3Z as the predictor genes in combination with well known statistical algorithms as would be understood by a person skilled in the art and described herein. Commercially available programs such as those provided by Silicon Genetics (e.g. GeneSpring™ for Class Predication are also available.

EXAMPLE 29

Identification of Genes Specific for OA Only by Removing Genes Relevant to Co-Morbidities and Other Disease States.

This example demonstrates the use of the claimed invention to detect differential gene expression in blood unique to Osteoarthritis as compared with other disease states.

Blood samples were taken from patients who were diagnosed with mild OA or severe OA and compared with individuals who were identified as normal individuals as defined herein. Gene expression profiles were then analysed to identify genes which are differentially expressed in OA as compared with normal. In each case, the diagnosis of OA was corroborated by a qualified physician.

Total mRNA from a drop of peripheral whole blood taken from each patient was isolated using TRIzol® reagent (GIBCO) and fluorescently labelled probes for each blood sample were generated as described above. Each probe was denatured and hybridized to a ChondroChip™ as described herein. Identification of genes differentially expressed in blood samples from patients with mild or severe OA as compared to healthy patients was determined by statistical analysis using the Weltch ANOVA test (Michelson and Schofield, 1996). (Dendogram analysis not shown).

In order to identify genes differentially expressed in blood unique to OA but not differentially expressed as a result of possible co-morbidities including hypertension, obesity, asthma, taking systemic steroids, or allergies, genes identified as differentially expressed in both OA and any of the genes identified as differentially expressed as a result of co-morbidity, e.g., Table 3A (co-morbidity of OA and hypertension v.

normal), Table 3B (co-morbidity of OA and obesity v. normal), Table 3C (co-morbidity of OA and allergy v. normal), Table 3D (co-morbidity of OA and taking systemic steroids v. normal), and genes in common with people identified as having asthma and OA (Table 3AA) were removed. Similarly any genes and unique to obesity (Table 3R), hypertension (Table 3P), allergies (Table 3T), systemic steroids (Table 3V) were also removed. As a result of these comparisons, a list of genes unique to individuals with OA was identified. The identity of the differentially expressed genes is shown in Table 3AB.

It would be clear to a person skilled in the art that rather than simply remove those genes which are relevant to other disease states, one could use a more refined analysis and remove those genes which show the same trend in gene expression, e.g. remove those genes which show up regulation in a co-morbid state and also show up-regulation in the single disease state, but retain those genes which show a different trend in gene expression e.g. retain those genes which show up regulation in a co-morbid state as compared to down regulation in a single disease state.

Classification or class prediction of a test sample of an individual to determine whether said individual has OA or does not have OA can be done using the differentially expressed genes as shown in Table 3AB, irrespective of whether the individual presents with co-morbidity using well known statistical algorithms as would be understood by a person skilled in the art and described herein. Commercially available programs such as those provided by Silicon Genetics (e.g. GeneSpring™) for Class Predication are also available.

EXAMPLE 30

Analysis of gene expression profiles of blood samples from individuals having brain cancer as compared with gene expression profiles from normal individuals.

This example demonstrates the use of the claimed invention to detect differential gene expression in blood samples taken from patients diagnosed with brain cancer as compared to blood samples taken from healthy patients.

As used herein "brain cancer" refers to all forms of primary brain tumours, both intracranial and extracranial and includes one or more of the following: Glioblastoma, Ependymoma, Gliomas, Astrocytoma, Medulloblastoma, Neuroglioma, Oligodendroglioma, Meningioma, Retinoblastoma, and Craniopharyngioma.

Blood samples are taken from patients diagnosed with brain cancer as defined herein. Gene expression profiles are then analysed and compared to profiles from patients unaffected by any disease. Preferably healthy patients are chosen who are age and sex matched to said patients diagnosed with disease. In each case, the diagnosis of brain cancer is corroborated by a skilled Board certified physician.

Total mRNA from a drop of peripheral whole blood is taken from each patient and isolated using TRIzol® reagent (GIBCO) and fluorescently labelled probes for each blood sample are generated as described above. Each probe is denatured and hybridized to an Affymetrix U133A Chip and/or a ChondroChip™ as described herein. Identification of genes differentially expressed in blood samples from patients with brain cancer as compared to healthy patients is determined by statistical analysis using the Wilcox Mann Whitney rank sum test (Glantz S A., Primer of Biostatistics, 5th ed., New York, USA: McGraw-Hill Medical Publishing Division, 2002).

Classification or class prediction of a test sample of an individual to determine whether said individuals has brain cancer or does not having brain cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 31

Analysis of gene expression profiles of blood samples from individuals having ankylosing spondylitis as compared with gene expression profiles from normal individuals.

This example demonstrates the use of the claimed invention to detect differential gene expression in blood samples taken from patients diagnosed with ankylosing spondylitis as compared to blood samples taken from healthy patients.

As used herein "ankylosing spondylitis" refers to a chronic inflammatory disease that affects the joints between the vertebrae of the spine, and/or the joints between the spine and the pelvis and can eventually cause the affected vertebrae to fuse or grow together.

Blood samples are taken from patients diagnosed with ankylosing spondylitis as defined herein. Gene expression profiles are then analysed and compared to profiles from patients unaffected by any disease. Preferably healthy patients are chosen who are age and sex matched to said patients diagnosed with disease. In each case, the diagnosis of ankylosing spondylitis is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with ankylosing spondylitis as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has ankylosing spondylitis or does not having ankylosing spondylitis can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 32

Analysis of gene expression profiles of blood samples from individuals having prostate cancer as compared with gene expression profiles from normal individuals.

This example demonstrates the use of the claimed invention to detect differential gene expression in blood samples taken from patients diagnosed with prostate cancer as compared to blood samples taken from healthy patients As used herein "prostate cancer" refers to a malignant cancer originating within the prostate gland. Patients identified as having prostate cancer can have any stage of prostate cancer, as determined clinically (by digital rectal exam or PSA testing) and or pathologically. Staging of prostate cancer can done in accordance with TNM or the Staging System of the American Joint Committee on Cancer (AJCC). In addition to the TNM system, other systems may be used to stage prostate cancer, for example, the Whitmore-Jewett system.

Blood samples are taken from patients diagnosed with prostate cancer as defined herein. Gene expression profiles are then analysed and compared to profiles from patients unaffected by any disease to identify genes which differentiate as between the two groups. Similarly gene expression profiles can be analysed so as to differentiate as between the severity of the prostate cancer. Preferably healthy patients are chosen who are age and sex matched to said patients diagnosed with disease or with a specific stage of said disease. In each case, the diagnosis of prostate cancer is corroborated by a skilled Board certified physician. Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with prostate cancer as compared to healthy patients is determined by statistical analysis using the Wilcox Mann Whitney rank sum test (Glantz S A., Primer of Biostatistics, 5th ed., New York, USA: McGraw-Hill Medical Publishing Division, 2002).

Classification or class prediction of a test sample of an individual to determine whether said individuals has prostate cancer, has a specific stage of prostate cancer, or does not having prostate cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 33

Analysis of gene expression profiles of blood samples from individuals having ovarian cancer as compared with gene expression profiles from normal individuals.

This example demonstrates the use of the claimed invention to detect differential gene expression in blood samples taken from patients diagnosed with ovarian cancer as compared to blood samples taken from healthy patients.

As used herein "ovarian cancer" refers to a malignant cancerous growth originating within the ovaries. Patients identified as having ovarian cancer can have any stage of ovarian cancer. Staging is done by combining information from imaging tests with the results of a surgical examination done during a laprotomy. Numbered stages I to IV are used to describe the extent of the cancer and whether it has spread (metastasized) to more distant organs.

Blood samples are taken from patients diagnosed with ovarian cancer, or with a specific stage of ovarian cancer as defined herein. Gene expression profiles are then analysed and compared to profiles from patients unaffected by any disease. Preferably healthy patients are chosen who are age and sex matched to said patients diagnosed with disease or with a specific stage of said disease. In each case, the diagnosis of ovarian cancer is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with ovarian cancer and or a specific stage of ovarian cancer as compared to healthy patients is determined by statistical analysis using the Wilcox Mann Whitney rank sum test (Glantz S A., Primer of Biostatistics, 5th ed., New York, USA: McGraw-Hill Medical Publishing Division, 2002).

Classification or class prediction of a test sample of an individual to determine whether said individuals has ovarian cancer, has a specific stage of ovarian cancer or does not having ovarian cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 34

Analysis of gene expression profiles of blood samples from individuals having kidney cancer as compared with gene expression profiles from normal individuals.

This example demonstrates the use of the claimed invention to detect differential gene expression in blood samples taken from patients diagnosed with kidney cancer as compared to blood samples taken from healthy patients.

As used herein "kidney cancer" refers to a malignant cancerous growth originating within the kidneys. Kidney cancer includes renal cell carcinoma, transitional cell carcinoma, and Wilms' tumor. Patients identified as having renal cell carcinoma can also be categorized by stage of said cancer as determined by the System of the American Joint Committee on Cancer (AJCC). Numbered stages I to IV are used to describe the extent of the carcinoma and whether it has spread (metastased) to more distant organs.

Blood samples are taken from patients diagnosed with kidney cancer, or with a specific stage of renal cell carcinoma as defined herein. Gene expression profiles are then analysed and compared to profiles from patients unaffected by any disease. Preferably healthy patients are chosen who are age and sex matched to said patients diagnosed with disease or with a specific stage of said disease. In each case, the diagnosis of kidney cancer is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with kidney cancer and or a specific stage of kidney cancer as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has kidney cancer, has a specific stage of kidney cancer or does not having kidney cancer can be done using the differentially expressed genes identified as described above as the predictor genes in combination with well known statistical algorithms as would be understood by a person skilled in the art and described herein. Commercially available programs such as

EXAMPLE 35

Analysis of gene expression profiles of blood samples from individuals having gastric cancer as compared with gene expression profiles from normal individuals.

This example demonstrates the use of the claimed invention to detect differential gene expression in blood samples taken from patients diagnosed with gastric cancer as compared to blood samples taken from healthy patients.

As used herein "gastric or stomach cancer" refers to a cancerous growth originating within the stomach and includes gastric adenocarcinoma, primary gastric lymphoma and gastric nonlymphoid sarcoma. Patients identified as having stomac can also be categorized by stage of said cancer as determined by the System of the American Joint Committee on Cancer (AJCC).

Blood samples are taken from patients diagnosed with stomach cancer, or with a specific stage of stomach cancer as defined herein. Gene expression profiles are then analysed and compared to profiles from patients unaffected by any disease. Preferably healthy patients are chosen who are age and sex matched to said patients diagnosed with disease or with a specific stage of said disease. In each case, the diagnosis of stomach cancer is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with stomach cancer and or a specific stage of stomach cancer as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has stomach cancer, has a specific stage of stomach cancer or does not having stomach cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 36

Analysis of gene expression profiles of blood samples from individuals having lung cancer as compared with gene expression profiles from normal individuals.

This example demonstrates the use of the claimed invention to detect differential gene expression in blood samples taken from patients diagnosed with lung cancer as compared to blood samples taken from healthy patients.

As used herein "lung cancer" refers to a cancerous growth originating within the lung and includes adenocarcinoma, alveolar cell carcinoma, squamous cell carcinoma, large cell and small cell carcinomas. Patients identified as having lung cancer can also be categorized by stage of said cancer as determined by the System of the American Joint Committee on Cancer (AJCC).

Blood samples are taken from patients diagnosed with lung cancer, or with a specific stage of lung cancer as defined herein. Gene expression profiles are then analysed and compared to profiles from patients unaffected by any disease. Preferably healthy patients are chosen who are age and sex matched to said patients diagnosed with disease or with a specific stage of said disease. In each case, the diagnosis of lung cancer is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with lung cancer and or a specific stage of lung cancer as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has lung cancer, has a specific stage of lung cancer or does not having lung cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 37

Analysis of gene expression profiles of blood samples from individuals having breast cancer as compared with gene expression profiles from normal individuals.

This example demonstrates the use of the claimed invention to detect differential gene expression in blood samples taken from patients diagnosed with breast cancer as compared to blood samples taken from healthy patients.

As used herein "breast cancer" refers to a cancerous growth originating within the breast and includes invasive and non invasive breast cancer such as ductal carcinoma in situ (DCIS), lobular carcinoma in situ (LCIS), infiltrating ductal carcinoma, and infiltrating lobular carcinoma. Patients identified as having breast cancer can also be categorized by stage of said cancer as determined by the System of the American Joint Committee on Cancer (AJCC) or TNM classification.

Blood samples are taken from patients diagnosed with breast cancer, or with a specific stage of breast cancer as defined herein. Gene expression profiles are then analysed and compared to profiles from patients unaffected by any disease. Preferably healthy patients are chosen who are age and sex matched to said patients diagnosed with disease or with a specific stage of said disease. In each case, the diagnosis of breast cancer is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with breast cancer and or a specific stage of breast cancer as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has breast cancer, has a specific stage of breast cancer or does not have breast cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 38

Analysis of gene expression profiles of blood samples from individuals having nasopharyngeal cancer as compared with gene expression profiles from normal individuals.

This example demonstrates the use of the claimed invention to detect differential gene expression in blood samples taken from patients diagnosed with nasopharyngeal cancer as compared to blood samples taken from healthy patients.

As used herein "nasopharyngeal cancer" refers to a cancerous growth arising from the epithelial cells that cover the surface and line the nasopharynx. Patients identified as having nasopharyngeal cancer can also be categorized by stage of said cancer as determined by the System of the American Joint Committee on Cancer (AJCC) or TNM classification.

Blood samples are taken from patients diagnosed with nasopharyngeal cancer, or with a specific stage of nasopharyngeal cancer as defined herein. Gene expression profiles are then analysed and compared to profiles from patients unaffected by any disease. Preferably healthy patients are chosen who are age and sex matched to said patients diagnosed with disease or with a specific stage of said disease. In each case, the diagnosis of nasopharyngeal cancer is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to a Affymetrix U133A Chip and/or a ChondroChip™ as described herein. Identification of genes differentially expressed in blood samples from patients with nasopharyngeal cancer and or a specific stage of breast cancer as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has nasopharyngeal cancer, has a specific stage of nasopharyngeal cancer or does not have nasopharyngeal cancer can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 39

Analysis of gene expression profiles of blood samples from individuals having Guillain Barre syndrome as compared with gene expression profiles from normal individuals.

This example demonstrates the use of the claimed invention to detect differential gene expression in blood samples taken from patients diagnosed with Guillain Barre syndrome as compared to blood samples taken from healthy patients.

As used herein "Guillain Barre syndrome" refers to an acute, usually rapidly progressive form of inflammatory polyneuropathy characterized by muscular weakness and mild distal sensory loss.

Blood samples are taken from patients diagnosed with Guillain Barre syndrome as defined herein. Gene expression profiles are then analysed and compared to profiles from patients unaffected by any disease. Preferably healthy patients are chosen who are age and sex matched to said patients diagnosed with disease. In each case, the diagnosis of Guillain Barre syndrome is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Guillain Barre syndrome as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has Guillain Barre syndrome, or does not have Guillain Barre syndrome can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 40

Analysis of gene expression profiles of blood samples from individuals having Fibromyalgia as compared with gene expression profiles from normal individuals.

This example demonstrates the use of the claimed invention to detect differential gene expression in blood samples taken from patients diagnosed with Fibromyalgia as compared to blood samples taken from healthy patients.

As used herein "Fibromyalgia" refers to widespread chronic musculoskeletal pain and fatigue. The pain comes from the connective tissues, such as the muscles, tendons, and ligaments and does not involve the joints. Blood samples are taken from patients diagnosed with Fibromyalgia as defined herein. Gene expression profiles are then analysed and compared to profiles from patients unaffected by any disease. Preferably healthy patients are chosen who are age and sex matched to said patients diagnosed with disease. In each case, the diagnosis of Fibromyalgia is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Fibromyalgia as compared to healthy patients is determined by statistical analysis using the Wilcox Mann Whitney rank sum test (Glantz S A., Primer of Biostatistics, 5th ed., New York, USA: McGraw-Hill Medical Publishing Division, 2002).

Classification or class prediction of a test sample of an individual to determine whether said individuals has Fibromyalgia, or does not have Fibromyalgia can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 41

Analysis of gene expression profiles of blood samples from individuals having Multiple Sclerosis as compared with gene expression profiles from normal individuals.

This example demonstrates the use of the claimed invention to detect differential gene expression in blood samples taken from patients diagnosed with Multiple Sclerosis as compared to blood samples taken from healthy patients.

As used herein "Multiple Sclerosis" refers to chronic progressive nervous disorder involving the loss of myelin sheath surrounding certain nerve fibres. Blood samples are taken from patients diagnosed with Multiple Sclerosis as defined herein. Gene expression profiles are then analysed and compared to profiles from patients unaffected by any disease. Preferably healthy patients are chosen who are age and sex matched to said patients diagnosed with disease. In each case, the diagnosis of Multiple Sclerosis is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Multiple Sclerosis as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has Multiple Sclerosis, or does not have Multiple Sclerosis can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 42

Analysis of gene expression profiles of blood samples from individuals having Muscular Dystrophy as compared with gene expression profiles from normal individuals.

This example demonstrates the use of the claimed invention to detect differential gene expression in blood samples taken from patients diagnosed with Muscular Dystrophy as compared to blood samples taken from healthy patients.

As used herein "Muscular Dystrophy" refers to a hereditary disease of the muscular system characterized by weakness and wasting of the skeletal muscles. Muscular Dystrophy includes Duchennes' Muscular Dystrophy, limb-girdle muscular dystrophy, myotonia atrophica, myotonic muscular dystrophy, pseudohypertrophic muscular dystrophy, and Steinhardt's disease.

Blood samples are taken from patients diagnosed with Muscular Dystrophy as defined herein. Gene expression profiles are then analysed and compared to profiles from patients unaffected by any disease. Preferably healthy patients are chosen who are age and sex matched to said patients diagnosed with disease. In each case, the diagnosis of Muscular Dystrophy is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Muscular Dystrophy as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has Muscular Dystrophy, or does not have Muscular Dystrophy can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 43

Analysis of gene expression profiles of blood samples from individuals having septic joint arthroplasty as compared with gene expression profiles from normal individuals.

This example demonstrates the use of the claimed invention to detect differential gene expression in blood samples taken from patients diagnosed with septic joint arthroplasty as compared to blood samples taken from healthy patients.

As used herein "septic joint arthroplasty" refers to an inflammation of the joint caused by a bacterial infection.

Blood samples are taken from patients diagnosed with septic joint arthroplasty as defined herein. Gene expression profiles are then analysed and compared to profiles from patients unaffected by any disease. Preferably healthy patients are chosen who are age and sex matched to said patients diagnosed with disease. In each case, the diagnosis of septic joint arthroplasty is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with septic joint arthroplasty as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has septic joint arthroplasty, or does not have septic joint arthroplasty can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 44

Analysis of gene expression profiles of blood samples from individuals having Alzheimers Disease as compared with gene expression profiles from normal individuals.

This example demonstrates the use of the claimed invention to detect differential gene expression in blood samples taken from patients diagnosed with Alzheimers as compared to blood samples taken from healthy patients.

As used herein "Alzheimers" refers to a degenerative disease of the central nervous system characterized especially by premature senile mental deterioration.

Blood samples are taken from patients diagnosed with Alzheimers as defined herein. Gene expression profiles are then analysed and compared to profiles from patients unaffected by any disease. Preferably healthy patients are chosen who are age and sex matched to said patients diagnosed with disease. In each case, the diagnosis of Alzheimers is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Alzheimers as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has Alzheimers, or does not have Alzheimers can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 45

Analysis of gene expression profiles of blood samples from individuals having hepatitis as compared with gene expression profiles from normal individuals.

This example demonstrates the use of the claimed invention to detect gene expression in blood samples taken from patients diagnosed with hepatitis as compared to blood samples taken from healthy patients.

As used herein "hepatitis" refers to an inflammation of the liver caused by a virus or toxin and can include hepatitis A, hepatitis B, hepatitis C, hepatitis D, hepatitis E, and hepatitis F.

Blood samples are taken from patients diagnosed with hepatitis as defined herein. Gene expression profiles are then analysed and compared to profiles from patients unaffected by any disease. Preferably healthy patients are chosen who are age and sex matched to said patients diagnosed with disease. In each case, the diagnosis of hepatitis is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with hepatitis as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has hepatitis, or does not have hepatitis can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 46

Analysis of gene expression profiles of blood samples from individuals having Manic Depression Syndrome (MDS) as compared with gene expression profiles from normal individuals.

This example demonstrates the use of the claimed invention to detect differential gene expression in blood samples taken from patients diagnosed with MDS as compared to blood samples taken from healthy patients.

As used herein "Manic Depression Syndrome (MDS)" refers to a mood disorder characterized by alternating mania and depression.

Blood samples are taken from patients diagnosed with MDS as defined herein. Gene expression profiles are then analysed and compared to profiles from patients unaffected by any disease. Preferably healthy patients are chosen who are age and sex matched to said patients diagnosed with disease. In each case, the diagnosis of MDS is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with MDS as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has MDS, or does not have MDS can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 47

Analysis of gene expression profiles of blood samples from individuals having Crohn's Disease and/or Colitis as compared with gene expression profiles from normal individuals.

This example demonstrates the use of the claimed invention to detect differential gene expression in blood samples taken from patients diagnosed with Crohn's Disease and/or Colitis as compared to blood samples taken from healthy patients.

As used herein "Crohn's Disease" refers to a chronic inflammation of the ileum which is often progressive. As used herein "Colitis" or "Inflammatory Bowel Disease" refers to inflammation of the colon.

Blood samples are taken from patients diagnosed with Crohn's and or Colitis as defined herein. Gene expression profiles are then analysed and compared to profiles from patients unaffected by any disease. Preferably healthy patients are chosen who are age and sex matched to said patients diagnosed with disease. In each case, the diagnosis of Crohn's and or Colitis is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Crohn's and or Colitis as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has Crohn's and or Colitis, or does not have Crohn's and or Colitis can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 48

Analysis of gene expression profiles of blood samples from individuals having Malignant Hyperthermia Susceptibility as compared with gene expression profiles from normal individuals.

This example demonstrates the use of the claimed invention to detect differential gene expression in blood samples taken from patients diagnosed with Malignant Hyperthermia Susceptibility as compared to blood samples taken from healthy patients.

As used herein "Malignant Hyperthermia Susceptibility" refers to a pharmacogenetic disorder of skeletal muscle calcium regulation often developing during or after a general anaesthesia.

Blood samples are taken from patients diagnosed with Malignant Hyperthermia Susceptibility as defined herein. Gene expression profiles are then analysed and compared to profiles from patients unaffected by any disease. Preferably healthy patients are chosen who are age and sex matched to said patients diagnosed with disease. In each case, the diagnosis of Malignant Hyperthermia Susceptibility is corroborated by a skilled Board certified physician.

Total mRNA from a drop of peripheral whole blood is taken from each patient and isolated using TRIzol® reagent (GIBCO) and fluorescently labelled probes for each blood sample is generated as described above. Each probe is denatured and hybridized to an Affymetrix U133A Chip and/or a ChondroChip™ as described herein. Identification of genes differentially expressed in blood samples from patients with Malignant Hyperthermia Susceptibility as compared to healthy patients is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of an individual to determine whether said individuals has Malignant Hyperthermia Susceptibility, or does not have Malignant Hyperthermia Susceptibility can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 49

Analysis of gene expression profiles of blood samples from horses having osteoarthritis as compared with gene expression profiles from normal or non-osteoarthritic horses.

This example demonstrates the use of the claimed invention to detect differential gene expression in blood samples taken from horses so as to diagnose equine arthritis as compared to blood samples taken from healthy horses.

As used herein "arthritis" in reference to horses refers to a degenerative joint disease that affects horses by causing lameness. Although it can appear in any joint, most common areas are the upper knee joint, front fetlocks, hocks, or coffin joints in the front feet. The condition can be caused by trauma, mineral or dietary deficiency, old age, poor conformation, over exertion or infection. The different structures that can be damaged in arthritis are the cartilage inside joints, the bone in the joints, the joint capsule, the synovial membranes, the ligaments around the joints and lastly the fluid that lubricates the insides of 'synovial joints'. In severe cases all of these structures are affected. In for example osteochondrosis only the cartilage may be affected.

Regardless of the cause, the disease begins when the synovial fluid that lubricates healthy joints begins to thin. The decrease in lubrication causes the cartilage cushion to break down, and eventually the bones begin to grind painfully against each other. Diagnostic tests used to confirm arthritis include X-rays, joint fluid analysis, and ultrasound.

Blood samples are taken from horses diagnosed with arthritis as defined herein. Gene expression profiles are then analysed and compared to profiles from horses unaffected by any disease. Preferably healthy horses are chosen who are age and sex matched to said horses diagnosed with disease. In each case, the diagnosis of arthritis is corroborated by a certified veterinarian.

Total mRNA from a drop of peripheral whole blood is taken from each horse and isolated using TRIzol® reagent (GIBCO) and fluorescently labelled probes for each blood sample is generated as described above. Each probe is denatured and hybridized to an Affymetrix U133A Chip and/or a ChondroChip™ as described herein. An equine specific microarray representing the equine genome can also be used. Identification of genes differentially expressed in blood samples from horses with arthritis as compared to healthy horses is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of a horse to determine whether said horse has arthritis or does not have arthritis can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 50

Analysis of gene expression profiles of blood samples from dogs having osteoarthritis as compared with gene expression profiles from normal or non-osteoarthritic dogs.

This example demonstrates the use of the claimed invention to detect differential gene expression in blood samples taken from dogs so as to diagnose equine arthritis as compared to blood samples taken from healthy horses.

As used herein "osteoarthritis" in reference to dogs is a form of degenerative joint disease which involves the deterioration of and changes to the cartilage and bone. In response to inflammation in and about the joint, the body responds with bony remodelling around the joint structure. This process can be slow and gradual with minimal outward symptoms, or more rapidly progressive with significant pain and discomfort. Osteoarthritic changes can occur in response to infection and injury of the joint as well.

Blood samples are taken from dogs diagnosed with osteoarthritis as defined herein. Gene expression profiles are then analysed and compared to profiles from dogs unaffected by any disease. Preferably healthy dogs are chosen who are age, sex and breed matched to said dogs diagnosed with disease. In each case, the diagnosis of osteoarthritis is corroborated by a certified veterinarian.

Total mRNA from a drop of peripheral whole blood is taken from each dog and isolated using TRIzol® reagent (GIBCO) and fluorescently labelled probes for each blood sample is generated as described above. Each probe is denatured and hybridized to an Affymetrix U133A Chip and/or a ChondroChip™ as described herein. A canine specific microarray representing the canine genome can also be used. Identification of genes differentially expressed in blood samples from dogs with osteoarthritis as compared to healthy horses is determined by statistical analysis using the Wilcox Mann Whitney rank sum test (Glantz S A, Primer of Biostatistics, 5th ed., New York, USA: McGraw-Hill Medical Publishing Division, 2002).

Classification or class prediction of a test sample of a dog to determine whether said dog has osteoarthritis or does not have osteoarthritis can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

EXAMPLE 51

Analysis of gene expression profiles of blood samples from individuals having Manic Depression Syndrome (MDS) as compared with gene expression profiles from individuals having Schizophrenia.

This example demonstrates the use of the claimed invention to detect differential gene expression in blood samples taken from patients diagnosed with MDS as compared to blood samples taken from schizophrenic patients.

As used herein "Manic Depression Syndrome (MDS)" refers to a mood disorder characterized by alternating mania and depression. As used herein, "schizophrenia" is defined as a psychotic disorders characterized by distortions of reality and disturbances of thought and language and withdrawal from social contact. Patients diagnosed with "schizophrenia" can include patients having any of the following diagnosis: an acute schizophrenic episode, borderline schizophrenia, catatonia, catatonic schizophrenia, catatonic type schizophrenia, disorganized schizophrenia, disorganized type schizophrenia, hebephrenia, hebephrenic schizophrenia, latent schizophrenia, paranoic type schizophrenia, paranoid schizophrenia, paraphrenia, paraphrenic schizophrenia, psychosis, reactive schizophrenia or the like.

Blood samples are taken from patients diagnosed with MDS or Schizophrenia as defined herein. Gene expression profiles are then analyzed and compared to profiles from patients unaffected by any disease. Preferably healthy patients are chosen who are age and sex matched to said patients diagnosed with disease. In each case, the diagnosis of MDS and Schizophrenia is corroborated by a skilled Board certified physician. Total mRNA from a drop of peripheral whole blood is taken from each patient and isolated using TRIzol® reagent (GIBCO) and fluorescently labelled probes for each blood sample is generated as described above.

Each probe is denatured and hybridized to an Affymetrix U133A Chip and/or a ChondroChip™ as described herein. Identification of genes differentially expressed in blood samples from patients with MDS as compared to Schizophrenic patients as compared to normal individuals is determined by statistical analysis using the Wilcox Mann Whitney rank sum test (Glantz S A, Primer of Biostatistics, 5th ed., New York, USA: McGraw-Hill Medical Publishing Division, 2002) (data not shown). 294 genes were identified as being differentially expressed with a p value of <0.05 as between the schizophrenic patients, the MDS patients and those control individuals. The identity of the differentially expressed genes is shown in Table 3AC.

Classification or class prediction of a test sample of an individual to determine whether said individuals has MDS, has Schizophrenia or is normal can be done using the differentially expressed genes identified as described above as the predictor genes in combination with well known statistical algorithms as would be understood by a person skilled in the art and described herein. Commercially available programs such as those provided by Silicon Genetics (e.g. GeneSpring™) for Class Predication are also available.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for indicating Chagas disease in a human test subject, said method comprising:
   a) quantifying a level of RNA encoded by a CDC14 cell division cycle 14 homolog A (*S. cerevisiae*) (CDC14A) gene in a blood sample of said test subject;
   b) comparing said level of RNA in said sample of said test subject with a quantified level of control RNA encoded by said gene in blood samples of control subjects which are classified as healthy control subjects; and
   c) comparing said level of RNA in said sample of said test subject with a quantified level of control RNA encoded by said gene in blood samples of control subjects which are classified as having Chagas disease;
   wherein a statistically significant determination with a p value less than 0.05 resulting from steps (b) and (c) that expression of said gene in said sample of said test subject is higher with a fold-change of at least 1.5 relative to said samples of said control subjects classified as healthy control subjects, and is similar relative to said samples of said control subjects classified as having Chagas disease, is indicative of Chagas disease in said human test subject.

2. The method of claim 1, wherein said blood sample of said test subject and said blood samples of said control subjects are selected from the group consisting of whole blood samples and blood samples which have not been fractionated into cell types.

3. The method of claim 1, wherein said quantifying of said level of RNA encoded by said gene in said sample of said test subject is effected relative to a housekeeping gene.

4. The method of claim 1, wherein said quantifying of said level of RNA encoded by said gene in said sample of said test subject is effected by quantification of cDNA complementary to RNA encoded by said gene.

5. The method of claim 1, wherein said quantifying of said level of RNA encoded by said gene is effected using quantitative PCR.

6. The method of claim 1, wherein said quantifying of said level of RNA encoded by said gene is effected using an array.

7. A method for detecting expression of a CDC14 cell division cycle 14 homolog A (*S. cerevisiae*) (CDC14A) gene in a human test subject, said method comprising detecting RNA encoded by said gene in a blood sample of said test subject, using an oligonucleotide of predetermined sequence which is specific only for RNA encoded by said gene in said sample, and/or for cDNA complementary to RNA encoded by said gene in said sample; quantifying a level of RNA encoded by said gene in said sample; comparing said level of RNA to a quantified level of control RNA encoded by said gene in blood samples of control subjects, wherein said control subjects are classified as healthy subjects; and classifying said test subject as being a candidate for having Chagas disease if said level of RNA encoded by said gene in said blood sample of said human test subject is statistically higher with a fold-change of at least 1.5 and with a p value less than 0.05 relative to that of said control subjects classified as healthy subjects.

8. A method of screening a human test subject for being a candidate for having Chagas disease, said method comprising:
   (a) detecting RNA encoded by a CDC14 cell division cycle 14 homolog A (*S. cerevisiae*) (CDC14A) gene in a blood sample of said test subject, using an oligonucleotide of predetermined sequence which is specific only for RNA encoded by said gene in said sample, and/or for cDNA complementary to RNA encoded by said gene in said sample; and
   (b) quantifying a level of RNA encoded by said gene in said sample of said test subject; and
   (c) comparing said level of RNA in said sample of said test subject to a quantified level of control RNA encoded by said gene in blood samples of control subjects classified as healthy subjects;
   wherein said test subject is a candidate for having Chagas disease if said level of RNA encoded by said gene in said blood sample of said test subject is statistically higher with a fold change of at least 1.5 and with a p value less than 0.05 relative to said level of RNA encoded by said gene in said samples of said control subjects classified as healthy subjects.

9. The method of claim 1, 7 or 8, wherein said human test subject is suspected of having Chagas disease.

10. The method of claim 7 or 8, wherein said blood sample of said test subject and said blood samples of said control subjects are selected from the group consisting of whole blood samples and blood samples which have not been fractionated into cell types.

11. The method of claim 7 or 8, wherein said quantifying of said level of RNA encoded by said gene in said sample of said test subject is effected relative to a housekeeping gene.

12. The method of claim 7 or 8, wherein said quantifying of said level of RNA encoded by said gene in said sample of said test subject is effected by quantification of cDNA complementary to RNA encoded by said gene.

13. The method of claim 7 or 8, wherein said quantifying of said level of RNA encoded by said gene is effected using quantitative PCR.

14. The method of claim 7 or 8, wherein said quantifying of said level of RNA encoded by said gene is effected using an array.

15. The method of claim 1, further wherein a statistically significant determination with a p value less than 0.05 resulting from steps (b) and (c) that expression of said gene in said sample of said test subject is lower with a fold-change of at least 1.5 relative to said samples of said control subjects classified as having Chagas disease, and is similar relative to said samples of said control subjects classified as healthy control subjects, is indicative of an absence of Chagas disease in said human test subject.

16. The method of claim 8, further wherein said test subject is a candidate for not having Chagas disease if said level of RNA encoded by said gene in said blood sample of said test subject is statistically similar with a p value less than 0.05 relative to said level of RNA encoded by said gene in said samples of said control subjects classified as healthy subjects.

17. The method of claim 15 or 16, wherein said blood sample of said test subject and said blood samples of said control subjects are selected from the group consisting of whole blood samples and blood samples which have not been fractionated into cell types.

18. The method of claim 15 or 16, wherein said quantifying of said level of RNA encoded by said gene in said sample of said test subject is effected relative to a housekeeping gene.

19. The method of claim 15 or 16, wherein said quantifying of said level of RNA encoded by said gene in said sample of said test subject is effected by quantification of cDNA complementary to RNA encoded by said gene.

20. The method of claim 15 or 16, wherein said quantifying of said level of RNA encoded by said gene is effected using quantitative PCR.

21. The method of claim 15 or 16, wherein said quantifying of said level of RNA encoded by said gene is effected using an array.

22. A method for indicating Chagas disease in a human test subject, said method comprising:
   a) quantifying a level of RNA encoded by a CDC14 cell division cycle 14 homolog A (*S. cerevisiae*) (CDC14A) gene in a blood sample of said test subject; and
   b) comparing said level of RNA in said sample of said test subject with a quantified level of control RNA encoded by said gene in blood samples of control subjects which are classified as healthy control subjects;
   wherein a statistically significant determination with a p value less than 0.05 resulting from step (b) that expression of said gene in said sample of said test subject is higher with a fold-change of at least 1.5 relative to said samples of said control subjects classified as healthy control subjects is indicative of Chagas disease in said human test subject.

23. A method for indicating Chagas disease in a human test subject, said method comprising:
   a) quantifying a level of RNA encoded by a CDC14 cell division cycle 14 homolog A (*S. cerevisiae*) (CDC14A) gene in a blood sample of said test subject; and
   b) comparing said level of RNA in said sample of said test subject with a quantified level of control RNA encoded by said gene in blood samples of control subjects which are classified as subjects having Chagas disease;
   wherein a statistically significant determination with a p value less than 0.05 resulting from step (b) that expression of said gene in said sample of said test subject is similar relative to said samples of said control subjects classified as subjects having Chagas disease is indicative of Chagas disease in said human test subject.

24. A method of screening a human test subject for being a candidate for having Chagas disease, said method comprising:
   (a) detecting RNA encoded by a CDC14 cell division cycle 14 homolog A (*S. cerevisiae*) (CDC14A) gene in a blood sample of said test subject, using an oligonucleotide of predetermined sequence which is specific only for RNA encoded by said gene in said sample, and/or for cDNA complementary to RNA encoded by said gene in said sample; and
   (b) quantifying a level of RNA encoded by said gene in said sample of said test subject; and
   (c) comparing said level of RNA in said sample of said test subject to a quantified level of control RNA encoded by said gene in blood samples of control subjects classified as subjects having Chagas disease;
   wherein said test subject is a candidate for having Chagas disease if said level of RNA encoded by said gene in said blood sample of said test subject is statistically similar with a p value less than 0.05 relative to said level of RNA encoded by said gene in said samples of said control subjects classified as subjects having Chagas disease.

25. A method of screening a human test subject for being a candidate for having Chagas disease, said method comprising:

(a) detecting RNA encoded by a CDC14 cell division cycle 14 homolog A (*S. cerevisiae*) (CDC14A) gene in a blood sample of said test subject, using an oligonucleotide of predetermined sequence which is specific only for RNA encoded by said gene in said sample, and/or for cDNA complementary to RNA encoded by said gene in said sample; and (b) quantifying a level of RNA encoded by said gene in said sample of said test subject; and (c) comparing said level of RNA in said sample of said test subject to a quantified level of control RNA encoded by said gene in blood samples of control subjects classified as healthy subjects; and (d) comparing said level of RNA in said sample of said test subject to a quantified level of control RNA encoded by said gene in blood samples of control subjects classified as having Chagas disease;

wherein said test subject is a candidate for having Chagas disease if said level of RNA encoded by said gene in said blood sample of said test subject is statistically higher with a fold change of at least 1.5 and with a p value less than 0.05 relative to said level of RNA encoded by said gene in said samples of said control subjects classified as healthy subjects and is statistically similar with a p value less than 0.05 relative to said level of RNA encoded by said gene in said samples of said control subjects classified as having Chagas disease.

26. The method of claim 22, 23, 24 or 25, wherein said blood sample of said test subject and said blood samples of said control subjects are selected from the group consisting of whole blood samples and blood samples which have not been fractionated into cell types.

27. The method of claim 22, 23, 24 or 25, wherein said quantifying of said level of RNA encoded by said gene in said sample of said test subject is effected relative to a housekeeping gene.

28. The method of claim 22, 23, 24 or 25, wherein said quantifying of said level of RNA encoded by said gene in said sample of said test subject is effected by quantification of cDNA complementary to RNA encoded by said gene.

29. The method of claim 22, 23, 24 or 25, wherein said quantifying of said level of RNA encoded by said gene is effected using quantitative PCR.

30. The method of claim 22, 23, 24 or 25, wherein said quantifying of said level of RNA encoded by said gene is effected using an array.

31. The method of claim 22, 23, 24 or 25, wherein said human test subject is suspected of having Chagas disease.

32. The method of claim 22, further wherein a statistically significant determination with a p value less than 0.05 resulting from step (b) that expression of said gene in said sample of said test subject is similar relative to said samples of said control subjects classified as healthy control subjects is indicative of an absence of Chagas disease in said human test subject.

33. The method of claim 23, further wherein a statistically significant determination with a p value less than 0.05 resulting from step (b) that expression of said gene in said sample of said test subject is lower with a fold-change of at least 1.5 relative to said samples of said control subjects classified as subjects having Chagas disease is indicative of an absence of Chagas disease in said human test subject.

34. The method of claim 24, further wherein said test subject is a candidate for not having Chagas disease if said level of RNA encoded by said gene in said blood sample of said test subject is statistically lower with a fold change of at least 1.5 and with a p value less than 0.05 relative to said level of RNA encoded by said gene in said samples of said control subjects classified as subjects having Chagas disease.

35. The method of claim 25 further wherein said test subject is a candidate for not having Chagas disease if said level of RNA encoded by said gene in said blood sample of said test subject is statistically lower with a fold change of at least 1.5 and with a p value less than 0.05 relative to said level of RNA encoded by said gene in said samples of said control subjects classified as having Chagas disease and is statistically similar with a p value less than 0.05 relative to said level of RNA encoded by said gene in said samples of said control subjects classified as healthy subjects.

36. The method of claim 32, 33, 34 or 35, wherein said blood sample of said test subject and said blood samples of said control subjects are selected from the group consisting of whole blood samples and blood samples which have not been fractionated into cell types.

37. The method of claim 32, 33, 34 or 35, wherein said quantifying of said level of RNA encoded by said gene in said sample of said test subject is effected relative to a housekeeping gene.

38. The method of claim 32, 33, 34 or 35, wherein said quantifying of said level of RNA encoded by said gene in said sample of said test subject is effected by quantification of cDNA complementary to RNA encoded by said gene.

39. The method of claim 32, 33, 34 or 35, wherein said quantifying of said level of RNA encoded by said gene is effected using quantitative PCR.

40. The method of claim 32, 33, 34 or 35, wherein said quantifying of said level of RNA encoded by said gene is effected using an array.

41. The method of claim 32, 33, 34 or 35, wherein said human test subject is suspected of having Chagas disease.

* * * * *